(12) United States Patent
Bezwada

(10) Patent No.: US 8,048,980 B2
(45) Date of Patent: Nov. 1, 2011

(54) HYDROLYSABLE LINKERS AND CROSS-LINKERS FOR ABSORBABLE POLYMERS

(75) Inventor: Rao S. Bezwada, Hillsborough, NJ (US)

(73) Assignee: Bezwada Biomedical, LLC, Hillsborough, NJ (US)

( * ) Notice: Subject to any disclaimer, the term of this patent is extended or adjusted under 35 U.S.C. 154(b) by 181 days.

(21) Appl. No.: 12/212,293

(22) Filed: Sep. 17, 2008

(65) Prior Publication Data

US 2009/0082540 A1 Mar. 26, 2009

Related U.S. Application Data

(60) Provisional application No. 60/972,855, filed on Sep. 17, 2007.

(51) Int. Cl.
*C08G 63/02* (2006.01)
(52) U.S. Cl. .................................. 528/272; 528/302
(58) Field of Classification Search .................. 528/272, 528/302
See application file for complete search history.

(56) References Cited

U.S. PATENT DOCUMENTS

| | | | |
|---|---|---|---|
| 3,044,942 A | 7/1962 | Baptist |
| 3,297,033 A | 1/1967 | Schmitt |
| 3,371,069 A | 2/1968 | Miyamae |
| 3,531,561 A | 9/1970 | Trehu |
| 3,636,956 A | 1/1972 | Schneider |
| 3,903,007 A | 9/1975 | Ernst |
| 3,987,797 A | 10/1976 | Stephenson |
| 4,020,100 A | 4/1977 | Evans |
| 4,024,871 A | 5/1977 | Stephenson |
| 4,052,988 A | 10/1977 | Doddi |
| 4,130,639 A | 12/1978 | Shalaby |
| 4,532,928 A | 8/1985 | Bezwada |
| 4,605,730 A | 8/1986 | Shalaby |
| 4,653,497 A | 3/1987 | Bezwada |
| 4,689,424 A | 8/1987 | Shalaby |
| 4,826,945 A | 5/1989 | Cohn |
| 4,829,099 A | 5/1989 | Fuller |
| 4,886,870 A | 12/1989 | D'Amore |
| 4,938,949 A | 7/1990 | Borch |
| 5,082,925 A | 1/1992 | Shalaby |
| 5,264,540 A | 11/1993 | Cooper |
| 5,378,540 A | 1/1995 | Olson |
| 5,521,431 A | 5/1996 | Tahara |
| 5,759,830 A | 6/1998 | Vacanti |
| 5,801,033 A | 9/1998 | Hubbell |
| 5,834,274 A | 11/1998 | Hubbell |
| 5,834,513 A | 11/1998 | Ptchelintsev |
| 5,843,743 A | 12/1998 | Hubbell |
| 5,895,150 A | 4/1999 | Watabe |
| 5,902,599 A | 5/1999 | Anseth |
| 5,932,229 A | 8/1999 | Ptchelintsev |
| 5,942,252 A | 8/1999 | Tice |
| 5,951,997 A | 9/1999 | Bezwada |
| 6,045,813 A | 4/2000 | Ferguson |
| 6,083,208 A | 7/2000 | Modak |
| 6,106,505 A | 8/2000 | Modak |
| 6,207,139 B1 | 3/2001 | Lee |
| 6,221,997 B1 | 4/2001 | Woodhouse |
| 6,224,579 B1 | 5/2001 | Modak |
| 6,468,519 B1 | 10/2002 | Uhrich |
| 6,596,657 B1 | 7/2003 | Shalaby |
| 6,689,350 B2 | 2/2004 | Uhrich |
| 6,773,721 B1 | 8/2004 | Wong |
| 6,780,799 B2 | 8/2004 | Shalaby |
| 6,861,068 B2 | 3/2005 | Ng |
| 6,869,615 B2 | 3/2005 | Chen |
| 6,887,974 B2 | 5/2005 | Pathak |
| 6,890,561 B1 | 5/2005 | Blatt |
| 6,955,827 B2 | 10/2005 | Barabolak |
| 2002/0028229 A1 | 3/2002 | Lezdey |
| 2002/0169275 A1 | 11/2002 | Matsuda |
| 2003/0158598 A1 | 8/2003 | Ashton |
| 2003/0216307 A1 | 11/2003 | Kohn |
| 2003/0232091 A1 | 12/2003 | Shefer |
| 2004/0096476 A1 | 5/2004 | Uhrich |
| 2004/0117007 A1 | 6/2004 | Whitbourne |
| 2004/0170597 A1 | 9/2004 | Beckman |
| 2004/0185250 A1 | 9/2004 | John |
| 2005/0013793 A1 | 1/2005 | Beckman |
| 2005/0048123 A1 | 3/2005 | East |
| 2005/0074493 A1 | 4/2005 | Mehta |
| 2005/0095300 A1 | 5/2005 | Wynn |
| 2005/0112171 A1 | 5/2005 | Tang |
| 2005/0152958 A1 | 7/2005 | Cordes |
| 2005/0238689 A1 | 10/2005 | Carpenter |
| 2006/0013851 A1 | 1/2006 | Giroux |
| 2006/0091034 A1 | 5/2006 | Scalzo |

(Continued)

FOREIGN PATENT DOCUMENTS

EP 0099177 1/1984

(Continued)

OTHER PUBLICATIONS

J. Org. Chem, 1959, 24, 523-526.
Gutowska et al, J. Biomater, Res., 29, 811-21 (1995).
Hoffman, J. Controlled Release, 6, 297-305 (1987).
Mikos et al, Biomaterials, 14, 323-329 (1993).
Shugens et al, J. Biomed. Mater. Res., 30, 449-462 (1996).
Langer, R., Science 249: 1527-1533 (1990).
van Dijk-Wolthuis, W.N.W.; Hoogeboom, J.; van Steenbergen, M.; Tsang, S.; and Hennick, W. "Degradation and Release Behavior of Dextran-Based Hydrogels", Macromolecules, 30; (1997) 4639-4645.
van Dijk-Wolthuis, W.N.E.; Tsang, S.; Kettenes-van den Bosch, J.; and Hennick, W. "A new class of polymerizable dextrans with hydrolysable groups: hydroxyethyl methacrylated dextran with and without oligolactate spacer", Polymer, 38 (25); (1997) 6235-6242.

(Continued)

*Primary Examiner* — Milton I Cano
*Assistant Examiner* — Gennadiy Mesh
(74) *Attorney, Agent, or Firm* — Vance Intellectual Property, PC

(57) ABSTRACT

The present invention relates to the discovery of new class of linear and multiarmed hydrolysable linkers and cross linkers for use in the synthesis of biodegradable polymers as, polyesters, polyurethanes, polyamides, polyureas and degradable epoxy amine resin. The linear and multiarmed hydrolysable linkers of the present invention include symmetrical and/or unsymmetrical ether carboxylic acids, amines, amide diols, amine polyols and isocyanates.

9 Claims, No Drawings

U.S. PATENT DOCUMENTS

| | | |
|---|---|---|
| 2006/0172983 A1 | 8/2006 | Bezwada |
| 2006/0188547 A1 | 8/2006 | Bezwada |
| 2007/0014755 A1 | 1/2007 | Beckman |
| 2007/0251831 A1 | 11/2007 | Kaczur |

FOREIGN PATENT DOCUMENTS

| | | |
|---|---|---|
| EP | 295055 | 12/1988 |
| EP | 1460089 | 9/2004 |
| WO | WO 95/26762 | 10/1995 |
| WO | WO 9638528 | 12/1996 |
| WO | WO 97/39738 | 10/1997 |
| WO | WO 98/36013 | 4/1998 |
| WO | WO 99/12990 | 3/1999 |
| WO | WO 99/29885 | 6/1999 |
| WO | WO 01/41753 | 6/2001 |
| WO | WO 02/09767 | 2/2002 |
| WO | WO 02/09768 | 2/2002 |
| WO | WO 2004/008101 | 1/2004 |
| WO | WO 2006/052790 | 5/2006 |

OTHER PUBLICATIONS

Kurisawa et al, Macromol. Chem. Phys. 199, 705-709 (1998).

Heller, J.; Helwing, R.F.; Baker, R.W.; and Tuttle, M.E. "Controlled release of water-soluble macromolecules from bioerodible hydrogels" Biomaterials, 4; (1983) 262-266.

Brondsted (Brondsted, H.; and Kopccek, J. "Hydrogels for site-specific oral drug deliver: synthesis and characterization" Biomaterials, 12; (1991) 584-592.

Ulbrich, K.; Subr, V.; Seymour, L.W.; and Duncan, R. "Novel biodegradable hydrogels prepared using the divinylic crosslinking agent N, O-dimethacryloylhydroxylamine 1. Synthesis and characterization of rates of gel degradation, and rate of release of model drugs, in vitro and in vivo" Journal of Controlled Release, 24; (1993) 181-190.

Kang, Tae-Gon; Han, Yang-Kyoo; New aliphatic diol/dicarboxylic acid based biodegradable polyesters and their in-vitro degradations, Polymer (Korea) 2005, 29(3), 314-319. Abstract Only.

Lee, Soo-Hong; Han, Yang-Kyoo; Kim, Eng Ryul; Im, Seung Soon; Synthesis and polymerization of new sequentially ordered aliphatic ester diols, Pollimo 1997, 21(6), 926-936. Abstract Only.

HYDROLYSABLE LINKERS AND CROSS-LINKERS FOR ABSORBABLE POLYMERS

CROSS REFERENCE TO RELATED APPLICATIONS

This application claims the benefit of U.S. Application No. 60/972,855, filed Sep. 17, 2007, the disclosure of which is hereby incorporated herein by reference in its entirety.

FIELD OF THE INVENTION

The present invention relates a new class of linear and multiarmed hydrolysable linkers and cross linkers and their synthetic intermediates for applications that include the synthesis of biodegradable polymers such as, polyesters, polyurethanes, polyamides, polyureas, and degradable epoxy amine resin. The linear and multiarmed hydrolysable linkers of the present invention include symmetrical and/or unsymmetrical ether carboxylic acids, amines, amide diols, amine polyols, and isocyanates.

BACKGROUND OF THE INVENTION

Much work has been accomplished in the last 20 years in the area of hydrophobic biodegradable polymers, wherein the biodegradable moieties include esters, lactones, orthoesters, carbonates, phosphazines, and anhydrides. Generally the polymers made of these biodegradable linkages are not water-soluble and therefore in themselves are not amenable for use in systems where water is required, such as in hydrogels.

Since the mechanism of biodegradation in these polymers is generally through the hydrolytically-active components of water (hydronium and hydroxide ions), the rate of hydrolytic scission of the bonds holding a polymer network together is generally pH sensitive, with these moieties being susceptible to both specific-acid catalyzed hydrolysis and base hydrolysis. Other factors affecting the degradation of materials made of these polymers are the degree of polymer crystallinity, the polymer volume fraction, the polymer molecular weight, the cross-link density, and the steric and electronic effects at the site of degradation.

Biodegradable network structures are prepared by placing covalent or non-covalent bonds within the network structure that may be broken under biologically relevant conditions. This involves the use of two separate structural motifs. The degradable structure is either placed into (i) the polymer backbone or (ii) into the cross-linker structure. In 1983, a system of degradable hydrogels was disclosed that reportedly included a water-soluble linear copolymer containing PEG, glycolylglycolic acid, and fumaric acid linkages (Heller, J.; Helwing, R. F.; Baker, R. W.; and Tuttle, M. E. "Controlled release of water-soluble macromolecules from bioerodible hydrogels." Biomaterials, 4; (1983) 262-266). The fumaric acid reportedly allowed the linear polymer to be cross-linked through free radical polymerization in a second network forming polymerization step, thus creating a polymer network that could degrade through hydrolysis of the glycolic ester linkages. This is an example of creating degradable linkages in the polymer backbone.

Biodegradable Cross-linkers: The first truly degradable cross-linking agents were reportedly made from aryl diazo compounds for delivery of drugs in the digestive tract. According to Brondsted (Brondsted, H.; and Kopccek, J. "Hydrogels for site-specific oral drug deliver: synthesis and characterization." Biomaterials, 12; (1991) 584-592), the diazo moiety may be cleaved by a bacterial azoreductase that is present in the colon. These agents are reportedly useful in the creation of colon specific delivery systems. A bis-vinylic compound based on hydroxylamine has been disclosed as a biodegradable cross-linking agent by Ulbrich and Duncan (Ulbrich, K.; Subr, V.; Seymour, L. W.; and Duncan, R. "Novel biodegradable hydrogels prepared using the divinylic crosslinking agent N,O-dimethacryloylhydroxylamine. 1. Synthesis and characterisation of rates of gel degradation, and rate of release of model drugs, in vitro and in vivo." Journal of Controlled Release, 24; (1993) 181-190.). Hydrogels made from this degradable cross-linker were said to undergo hydroxide-induced hydrolysis of the nitrogen-oxygen bond.

Hubbell et al. (U.S. Pat. Nos. 5,801,033; 5,834,274; and 5,843,743) have disclosed hydrogels composed of macro monomers derived in a multi step synthetic process. According to Hubbell, the macromonomers are composed of a central PEG diol which was transesterified using tin octanoate catalyzed ring opening polymerization of lactide to give a bis-oligolactate PEG. Following this step, the resultant bis-oligolactate PEG was then reportedly reacted with acryloyl chloride to give a macromolecular cross-linker. Hubbell disclosed that the macromolecular cross-linker could be converted into a homo-polymer interpenetrating network of PEG and oligolacetylacrylate through free radical polymerization (Pathak et al, U.S. Pat. No. 6,887,974). Hubbell (U.S. Pat. Nos. 5,801,033; 5,834,274; and 5,843,743) disclosed these compounds as photopolymerizable homo-polymers reportedly useful in preventing surgical adhesion.

Van Dijk-Wolthius et al. (van Dijk-Wolthuis, W. N. W.; Hoogeboom, J.; van Steenbergen, M.; Tsang, S.; and Hennick, W. "Degradation and Release Behavior of Dextran-Based Hydrogels." Macromolecules, 30; (1997) 4639-4645; .van Dijk-Wolthuis, W. N. E.; Tsang, S.; Kettenes-van den Bosch, J.; and Hennick, W. "A new class of polymerizable dextrans with hydrolyzable groups: hydroxyethyl methacrylated dextran with and without oligolactate spacer." Polymer, 38(25); (1997) 6235-6242) has recently reported a second solution to this problem, using a biodegradable cross-linking macromonomer composed of alpha-hydroxy esters This work reportedly combines natural polymers with synthetic polymers in an interpenetrating network. This group disclosed functionalized dextran with oligo-alpha-hydroxy acid domains, which were end capped with vinyl regions that were polymerized into biodegradable networks via free radical polymerization.

The most recent report of a biodegradable cross-linking agent involved an agent designed to undergo enzymatic degradation. This cross-linker is indicated to include a centrosymmetric peptide terminated by acrylamide moieties with a central diamine linking the two ends (Kurisawa et al, Macromol. Chem. Phys. 199, 705-709 (1998).

Pathak (U.S. Pat. No. 6,887,974) described polymeric cross-linking agents reportedly having an inert water-soluble polymeric component, a biodegradable component, and functional components that are reactive with chemical groups on a protein such as amine or thiol. According to Pathak, the inert polymeric component may be flanked at each end with a biodegradable component, which is flanked at each end with a protein reactive functional component. Pathak also disclosed a polymeric crosslinking agent having a biodegradable component, polyalkylene oxide, and at least three reactive functional groups, each of them reportedly capable of forming a covalent bond in water with at least one functional group such as an amine, thiol, or carboxylic acid.

Ashton et al. (US Patent Application Ser. No. 20030158598) disclosed medical devices having a coating disposed on at least one surface, wherein the coating reportedly includes a polymer matrix and a low solubility anti-inflammatory corticosteroid formulation or low solubility codrug or prodrug of an anti-inflammatory corticosteroid formulation.

Uhrich et al (US Patent Application Ser. No. 20040096476) described therapeutic devices including a polymeric anti-inflammatory agent that reportedly biodegrades to release anti-inflammatory agents. The therapeutic devices are disclosed as being useful for repair and regeneration of a variety of injured tissues.

Carpenter, et al, (US Patent Application Ser. No. 20050238689) disclosed a bioactive implantable stent including a stent structure with a surface coating of a biodegradable, bioactive polymer, wherein the polymer is said to include at least one bioligand covalently bound to the polymer and wherein the bioligand are said to specifically bind to integrin receptors on progenitors of endothelial cells (PECs) in circulating blood.

Giroux (US Patent Application Ser. No. 20060013851) described polyanhydrides which link low molecular weight drugs containing a carboxylic acid group and an amine, thiol, alcohol, or phenol group within their structure into polymeric drug delivery systems. Also reported are methods of producing polymeric drug delivery systems via these polyanhydride linkers as well as methods of administering low molecular weight drug to a host via the polymeric drug delivery systems. Medical implants based on the polymeric drug delivery system of the invention are also disclosed.

The use of isocyanate linkers to make hydrolysable active agent biopolymer conjugates was described in WO2004008101.

Biodegradable linkers for molecular therapies were described in WO2006052790.

Ptchelintsev et al. described the use of oxa acids and related compounds for treatment of skin conditions in U.S. Pat. Nos. 5,932,229 and 5,834,513 respectively.

Kiser et al. (U.S. Pat. No. 5,521,431) disclosed biodegradable cross-linkers having a polyacid core with at least two acidic groups covalently connected to reactive groups reportedly usable to cross-link polymer filaments. A biodegradable region is disclosed by Kiser between at least one reactive group and an acidic group of the polyacid preferably consisting of a hydroxyalkyl acid ester sequence having 1 to 6 hydroxyalkyl acid ester groups.

According to Kiser, the polyacid may be attached to a water-soluble region that is attached to the biodegradable region having attached reactive groups. Lactate or glycolate is reportedly preferred as the hydroxyalkyl acid ester group. Polyacids include diacids; triacids, tetraacids, pentaacids and the reactive group may contain a carbon-carbon double bond. A network of cross-linked polymer filaments having a defined biodegradation rate is said to be formed using the cross-linkers. Kiser discloses that the network may contain biologically active molecules, and may be in the form of a microparticle or nanoparticle, or hydrogel. The polymer filaments are reportedly derived from polymer filaments of polynucleic acids, polypeptides, proteins or carbohydrates. Reportedly, the cross-linkers may be copolymerized with charged monomers such as acrylic monomers containing charged groups. Applications of the cross-linkers and network are said to include controlled release of drugs and cosmetics, tissue engineering, wound healing, hazardous waste remediation, metal chelation, swellable devices for absorbing liquids and prevention of surgical adhesions.

In U.S. Pat. No. 4,829,099, Fuller disclosed metabolically acceptable polyisocyanate or polyisothiocyanate monomers as tissue adhesives. More particularly, this invention discloses surgical adhesive polymers derived from these polyisocyanate monomers, wherein the surgical polymers do not metabolize to toxic products. Amine precursors of these polyisocyanates were not isolated or identified and were not described for any applications.

The majority of biodegradable polymers are not soluble in water. As a consequence, a hydrophilic drug must be formulated in these polymers by, for example, a dispersion method using a two-phase system of water (containing drug) and organic solvent (containing the polymer). The solvent is removed by evaporation resulting in a solid polymer containing aqueous droplets. This type of system suffers from the need to use organic solvents. The use of these solvents is undesirable for protein delivery and may lead to denaturation of the protein, among other things.

Several problems associated with prior art biodegradable polymers have limited their commercial use. Biodegradable polymers typically have a polydispersed molecular architecture, which at least in part, is a function of their standard mode of preparation, i.e., stepwise condensation. As an undesirable consequence of this stepwise condensation, the resultant material will contain cross-links with a variety of degradation rates, in contrast to a more preferred tunable degradation profile, because the rate of degradation is related to the polydispersed molecular architecture. Synthetic biodegradable polymers are generally water insoluble as are a significant number of their precursors. The water insolubility of these materials adversely affects their biodegradability. Thus, there is a need for enhancing water solubility to improve biodegradability of certain polymers.

Thus, there is still an unfulfilled need for new materials (e.g., linkers and polymers derived therefrom) that are easily synthesized, composed of biocompatible components, and/or have improved water compatibility, that avoid the use of during their use in drug formulation, and/or have a well defined and/or controllable molecular structure leading to defined biodegradation rates. The present invention is directed to these, as well as other important ends.

SUMMARY OF THE INVENTION

In one aspect, the present invention provides biologically-acceptable and biodegradable linear and multiarmed linkers and cross-linkers with tunable degradation profiles.

In other aspects, the present invention provides linear and multiarmed hydrolysable monomeric and/or oligomeric linkers, or pharmaceutically acceptable salts thereof of formulas I, II, III, or IV:

$$R[-C(=O)-(Y)_a-O-R^1]_w \qquad \text{I}$$

$$R[-(X)_a-OC(=O)-R^2]_w \qquad \text{II}$$

$$R[-(Y)_a-O-R^3]_w \qquad \text{III}$$

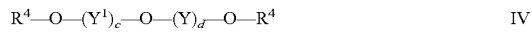

$$R^4-O-(Y^1)_c-O-(Y)_d-O-R^4 \qquad \text{IV}$$

wherein:

each $-O-R^1$, $-O-R^3$, $-O-R^4$, and $R^4-O-$ is independently:

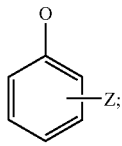

each —OC(=O)—R² is independently:

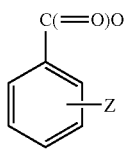

each Z is independently: $NH_2$, $NH(Y^1)_bH$, $N((X^1)_bH)_2$, NCO, $CH_2CO_2H$, or $CH=CHCO_2H$;

each X is independently:
—OC(=O)CH₂— (inverse glycolic acid moiety), —OC(=O)CH(CH₃)— (inverse lactic acid moiety), —OC(=O)CH₂OCH₂CH₂— (inverse dioxanone acid moiety), —OC(=O)CH₂CH₂CH₂CH₂CH₂— (inverse caprolactone acid moiety), —OC(=O)(CH₂)$_y$—, or —OC(=O)CH₂(OCH₂CH₂)$_z$—.

each X¹ is independently:
—CH₂C(=O)O— (glycolic acid moiety), —CH(CH₃)C(=O)O— (lactic acid moiety), —CH₂CH₂OCH₂C(=O)O— (dioxanone acid moiety), —CH₂CH₂CH₂CH₂CH₂C(=O)O— (caprolactone acid moiety), —(CH₂)$_y$C(=O)O—, or —(CH₂CH₂O)$_n$CH₂C(=O)O—;

each Y is independently:
—OCH₂C(=O)— (inverse glycolic ester moiety), —OCH(CH₃)C(=O)— (inverse lactic ester moiety), —OCH₂CH₂OCH₂C(=O)— (inverse dioxanone ester moiety), —OCH₂CH₂CH₂CH₂CH₂C(=O)— (inverse caprolactone ester moiety), —O(CH₂)$_m$C(=O)—, or —O(CH₂CH₂O)$_n$OCH₂C(=O)—;

each Y¹ is independently:
—C(=O)CH₂O— (glycolic ester moiety), —C(=O)CH(CH₃)O— (lactic ester moiety), —C(=O)CH₂OCH₂CH₂O— (dioxanone ester moiety), —C(=O)CH₂CH₂CH₂CH₂CH₂O— (caprolactone ester moiety), C(=O)(CH₂)$_m$O—, or —C(=O)CH₂—O—(CH₂CH₂O)$_n$—;

R is a di-, tri, tetra-, penta- or hexaradical derived from C₁₋₂₅ alkyl, aryl, or aryl-(C₁₋₆alkyl)₁₋₃-, wherein from 1-4 of the CH₂ groups, preferably 1-3 of the CH₂ groups, within the alkyl chain are optionally independently replaced by O or S atoms, preferably by O atoms, such that each of said O or S atoms is attached only to carbon atoms in the alkyl chain, with the proviso that the O or S atoms are separated from the di-, tri, tetra-, penta- or hexaradical chain ends by at least one carbon atom and that multiple O or S atoms in the di-, tri, tetra-, penta- or hexaradical chain must be separated from each other by at least two carbon atoms; or R is —[CH₂CH₂O—]$_p$—, wherein p is an integer from about 10 to about 50;

each a and b is independently an integer from about 0 to about 6;

each m, n, y, and z is independently an integer from about 2 to about 24;

w is an integer from about 2 to about 6; and c and d are each an integer from 1 to 5, with the proviso that the sum of c+d is an integer from about 2 to about 6.

In another aspect, the present invention provides absorbable polymers. In certain aspects, these polymers are useful for wound closure devices and application such as sutures, staples, clips, adhesion prevention barriers, and tissue adhesives with controlled degradation profiles, as well as other biomedical devices.

In another aspect, the present invention provides cross-linked hydrogels for drug delivery with controlled degradation profiles.

In another aspect, the present invention is directed to compounds of formula Iva:

$$R^{4a}-O-(Y^{1a})_c-O-(Y^a)_d-O-R^{4a} \qquad \text{IVa}$$

wherein:

each $Y^{1a}$ is independently:
—C(=O)CH₂O—, —C(=O)CH(CH₃)O—, —C(=O)CH₂OCH₂CH₂O—, —C(=O)CH₂CH₂CH₂CH₂CH₂O—, —C(=O)(CH₂)$_m$O—, or —C(=O)CH₂—O—(CH₂CH₂O)$_n$—;

each $Y^a$ is independently:
—OCH₂C(=O)—, —OCH(CH₃)C(=O)—, —OCH₂CH₂OCH₂C(=O)—, —OCH₂CH₂CH₂CH₂CH₂C(=O)—, —O(CH₂)$_m$C(=O)—, or —O(CH₂CH₂O)$_n$OCH₂C(=O)—;

each $R^{4a}$ is independently H, alkyl, or aralkyl;

each m and n is independently an integer from about 2 to about 24; and c and d are each an integer from 1 to 5, with the proviso that the sum of c+d is an integer from about 2 to about 6.

In some other aspects, the present invention is directed to linkers or pharmaceutically acceptable salts thereof of formula Iz, IIz, IIIz, IVz, or Vz:

$$R[-C(=O)-(Y)_a-O-R^{1b}]_w \qquad \text{Iz}$$

$$R[-(X)_a-OC(=O)-R^{2b}]_w \qquad \text{Iz}$$

$$R[-(Y)_a-O-R^{3b}]_w \qquad \text{IIIz}$$

$$R^4-O-(Y^1)_c-O-(Y)_d-O-R^{4b} \qquad \text{IVz}$$

$$R[-(X)_a-O-R^{5b}]_w \qquad \text{Vz}$$

wherein:

each —O—$R^{1b}$, —O—$R^{3b}$, —O—$R^{4b}$, $R^{4b}$—O—, and —O—$R^{5b}$ is independently:

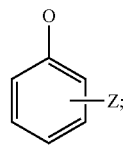

each —OC(=O)—$R^{2b}$ is independently:

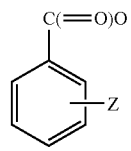

each Z is independently: $NH_2$, $NH(Y^1)_bH$, $N((X^1)_bH)_2$, NCO, $CH_2CO_2H$, or $CH=CHCO_2H$;

each X is independently:
—OC(=O)CH$_2$— (inverse glycolic acid moiety),
—OC(=O)CH(CH$_3$)— (inverse lactic acid moiety),
—OC(=O)CH$_2$OCH$_2$CH$_2$— (inverse dioxanone acid moiety), —OC(=O)CH$_2$CH$_2$CH$_2$CH$_2$CH$_2$— (inverse caprolactone acid moiety), —OC(=O)(CH$_2$)$_y$—, or —OC(=O)CH$_2$(OCH$_2$CH$_2$)$_z$—.

each X$^1$ is independently:
—CH$_2$C(=O)O— (glycolic acid moiety), —CH(CH$_3$)C(=O)O— (lactic acid moiety), —CH$_2$CH$_2$OCH$_2$C(=O)O— (dioxanone acid moiety), —CH$_2$CH$_2$CH$_2$CH$_2$CH$_2$C(=O)O— (caprolactone acid moiety), —(CH$_2$)$_y$C(=O)O—, or —(CH$_2$CH$_2$O)$_n$CH$_2$C(=O)O—;

each Y is independently:
—OCH$_2$C(=O)— (inverse glycolic ester moiety), —OCH(CH$_3$)C(=O)— (inverse lactic ester moiety), —OCH$_2$CH$_2$OCH$_2$C(=O)— (inverse dioxanone ester moiety), —OCH$_2$CH$_2$CH$_2$CH$_2$CH$_2$C(=O)— (inverse caprolactone ester moiety), —O(CH$_2$)$_m$C(=O)—, or —O(CH$_2$CH$_2$O)$_n$OCH$_2$C(=O)—;

each Y$^1$ is independently:
—C(=O)CH$_2$O— (glycolic ester moiety), —C(=O)CH(CH$_3$)—O— (lactic ester moiety), —C(=O)CH$_2$OCH$_2$CH$_2$O— (dioxanone ester moiety), —C(=O)CH$_2$CH$_2$CH$_2$CH$_2$CH$_2$O— (caprolactone ester moiety), C(=O)(CH$_2$)$_m$O—, or —C(=O)CH$_2$—O—(CH$_2$CH$_2$O)$_n$—;

R is a di-, tri, tetra-, penta- or hexaradical derived from C$_{1-25}$ alkyl, aryl, or aryl-(C$_{1-6}$alkyl)$_{1-3}$-, wherein from 1-3 of the CH$_2$ groups within the alkyl chain are optionally independently replaced by O or S atoms, such that each of said O or S atoms is attached only to carbon atoms in the alkyl chain, with the proviso that multiple heteroatoms must be separated from each other and from the di-, tri, tetra-, penta- or hexaradical chain ends by at least one carbon atom; or R is —[CH$_2$CH$_2$O—]$_p$—, wherein p is an integer from about 10 to about 50;

each a and b is independently an integer from about 1 to about 6;

each m, n, y, and z is independently an integer from about 2 to about 24;

w is an integer from about 2 to about 6; and c and d are each an integer from 1 to 5, with the proviso that the sum of c+d is an integer from about 2 to about 6.

In certain other aspects, the present invention is directed to compounds of formula Iz, IIz, IIIz, IVz, or Vz:

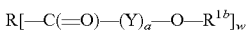   Iz

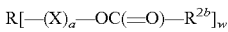   Iz

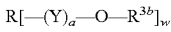   IIIz

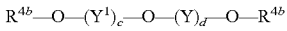   IVz

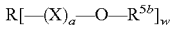   Vz wherein:
each R$^{1b}$, R$^{2b}$, R$^{3b}$, R$^{4b}$, and R$^{5b}$ is independently H, alkyl, or aralkyl;
each Z is independently: NH$_2$, NH(Y$^1$)$_b$H, N((X$^1$)$_b$H)$_2$, NCO, CH$_2$CO$_2$H, or CH=CHCO$_2$H;

each X is independently:
—OC(=O)CH$_2$— (inverse glycolic acid moiety),
—OC(=O)CH(CH$_3$)— (inverse lactic acid moiety),
—OC(=O)CH$_2$OCH$_2$CH$_2$— (inverse dioxanone acid moiety), —OC(=O)CH$_2$CH$_2$CH$_2$CH$_2$CH$_2$— (inverse caprolactone acid moiety), —OC(=O)(CH$_2$)$_y$—, or —OC(=O)CH$_2$(OCH$_2$CH$_2$)$_z$—.

each X$^1$ is independently:
—CH$_2$C(=O)O— (glycolic acid moiety), —CH(CH$_3$)C(=O)O— (lactic acid moiety), —CH$_2$CH$_2$OCH$_2$C(=O)O— (dioxanone acid moiety), —CH$_2$CH$_2$CH$_2$CH$_2$CH$_2$C(=O)O— (caprolactone acid moiety), —(CH$_2$)$_y$C(=O)O—, or —(CH$_2$CH$_2$O)$_n$CH$_2$C(=O)O—;

each Y is independently:
—OCH$_2$C(=O)— (inverse glycolic ester moiety), —OCH(CH$_3$)C(=O)— (inverse lactic ester moiety), —OCH$_2$CH$_2$OCH$_2$C(=O)— (inverse dioxanone ester moiety), —OCH$_2$CH$_2$CH$_2$CH$_2$CH$_2$C(=O)— (inverse caprolactone ester moiety), —O(CH$_2$)$_m$C(=O)—, or —O(CH$_2$CH$_2$O)$_n$OCH$_2$C(=O)—;

each Y$^1$ is independently:
—C(=O)CH$_2$O— (glycolic ester moiety), —C(=O)CH(CH$_3$)O— (lactic ester moiety), —C(=O)CH$_2$OCH$_2$CH$_2$O— (dioxanone ester moiety), —C(=O)CH$_2$CH$_2$CH$_2$CH$_2$CH$_2$O— (caprolactone ester moiety), C(=O)(CH$_2$)$_m$O—, or —C(=O)CH$_2$—O—(CH$_2$CH$_2$O)$_n$—;

R is a di-, tri, tetra-, penta- or hexaradical derived from C$_{1-25}$ alkyl, aryl, or aryl-(C$_{1-6}$alkyl)$_{1-3}$-, wherein from 1-3 of the CH$_2$ groups within the alkyl chain are optionally independently replaced by O or S atoms, such that each of said O or S atoms is attached only to carbon atoms in the alkyl chain, with the proviso that multiple heteroatoms must be separated from each other and from the di-, tri, tetra-, penta- or hexaradical chain ends by at least one carbon atom; or R is —[CH$_2$CH$_2$O—]$_p$—, wherein p is an integer from about 10 to about 50;

each a and b is independently an integer from about 1 to about 6;

each m, n, y, and z is independently an integer from about 2 to about 24;

w is an integer from about 2 to about 6; and c and d are each an integer from 1 to 5, with the proviso that the sum of c+d is an integer from about 2 to about 6.

In certain aspects of the invention, these compounds are useful as intermediates in the preparation of the linkers of the present invention, and/or polymers derived therefrom.

These and other objects, which will become apparent during the following detailed description, have been achieved by the inventors' discovery that the presently claimed linkers are useful for forming tunable biodegradable polymers.

DETAILED DESCRIPTION OF THE INVENTION

The present invention relates to the discovery of new class of linear and multiarmed hydrolysable linkers and cross linkers respectively for applications including the synthesis of biodegradable polymers such as polyesters, polyurethanes, polyamides, polyureas, and degradable epoxy amine resin. The linear and multiarmed hydrolysable linkers of the present invention include symmetrical and/or unsymmetrical ether carboxylic acids, amines, amide diols, amine polyols, and isocyanates. In certain embodiments of the present invention, the application of these linkers and crosslinkers during synthesis may result in biodegradable polymers with controlled degradation profiles.

More particularly, the present invention described herein provides biologically-acceptable and biodegradable linear and multiarmed linkers and cross-linkers with tunable degradation profiles, preferably using methods of stepwise synthesis of the degradable region, which results in purer compounds at the end of the synthetic sequence. The synthetic sequence, in many instances, and the resulting purity of the linkers leads to reaction products that are also readily purifiable.

While not wishing to be bound by theory, Applicants believe that the length of the degradable region is a major structural determinant of the degradation rate. Thus, in certain embodiments, the present invention provides a controlled degradation rate. By varying the functionalizing moiety or combination of moieties, the rate of biodegradation may be varied over a period of time, for example, from about one month to about four years, and may be selected as desired, depending on the end-use.

Applicants have discovered that the invention described herein is applicable to hydrophobic networks as well as hydrophilic networks. In some embodiments, rapid degradation rate and water solubility through the incorporation of oligomeric cross-linking compounds of the present invention are among the useful physical and/or chemical properties that are attainable without resorting to polymeric cross-linking compounds.

Accordingly, in some embodiments, the present invention provides novel linear and multiarmed hydrolysable monomeric and/or oligomeric linkers, or pharmaceutically acceptable salts thereof of formulas I, II, III, or IV:

$$R[-C(=O)-(Y)_a-O-R^1]_w \qquad \text{I}$$

$$R[-(X)_a-OC(=O)-R^2]_w \qquad \text{II}$$

$$R[-(Y)_a-O-R^3]_w \qquad \text{III}$$

$$R^4-O-(Y^1)_n-O-(Y)_d-O-R^4 \qquad \text{IV}$$

wherein:
each $-O-R^1$, $-O-R^3$, $-O-R^4$, and $R^4-O-$ is independently:

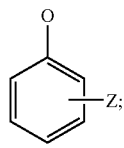

each $-OC(=O)-R^2$ is independently:

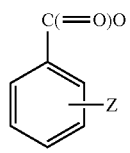

each Z is independently: $NH_2$, $NH(Y^1)_bH$, $N((X^1)_bH)_2$, NCO, $CH_2CO_2H$, or $CH=CHCO_2H$;
each X is independently:
  $-OC(=O)CH_2-$ (inverse glycolic acid moiety),
  $-OC(=O)CH(CH_3)-$ (inverse lactic acid moiety),
  $-OC(=O)CH_2OCH_2CH_2-$ (inverse dioxanone acid moiety), $-OC(=O)CH_2CH_2CH_2CH_2-$ (inverse caprolactone acid moiety), $-OC(=O)(CH_2)_y-$, or $-OC(=O)CH_2(OCH_2CH_2)_z-$.
each $X^1$ is independently:
  $-CH_2C(=O)O-$ (glycolic acid moiety), $-CH(CH_3)C(=O)O-$ (lactic acid moiety), $-CH_2CH_2OCH_2C(=O)O-$ (dioxanone acid moiety), $-CH_2CH_2CH_2CH_2CH_2C(=O)O-$ (caprolactone acid moiety), $-(CH_2)_yC(=O)O-$, or $-(CH_2CH_2O)_nCH_2C(=O)O-$;

each Y is independently:
  $-OCH_2C(=O)-$ (inverse glycolic ester moiety), $-OCH(CH_3)C(=O)-$ (inverse lactic ester moiety), $-OCH_2CH_2OCH_2C(=O)-$ (inverse dioxanone ester moiety), $-OCH_2CH_2CH_2CH_2CH_2C(=O)-$ (inverse caprolactone ester moiety), $-O(CH_2)_mC(=O)-$, or $-O(CH_2CH_2O)_nOCH_2C(=O)-$;

each $Y^1$ is independently:
  $-C(=O)CH_2O-$ (glycolic ester moiety), $-C(=O)CH(CH_3)O-$ (lactic ester moiety), $-C(=O)CH_2OCH_2CH_2O-$ (dioxanone ester moiety), $-C(=O)CH_2CH_2CH_2CH_2O-$ (caprolactone ester moiety), $C(=O)(CH_2)_mO-$, or $-C(=O)CH_2-O-(CH_2CH_2O)_n-$;

R is a di-, tri, tetra-, penta- or hexaradical derived from $C_{1-25}$ alkyl, aryl, or aryl-$(C_{1-6}alkyl)_{1-3}$-, wherein from 1-4 of the $CH_2$ groups, preferably 1-3 of the $CH_2$ groups, within the alkyl chain are optionally independently replaced by O or S atoms, preferably by O atoms, such that each of said O or S atoms is attached only to carbon atoms in the alkyl chain, with the proviso that the O or S atoms are separated from the di-, tri, tetra-, penta- or hexaradical chain ends by at least one carbon atom and that multiple O or S atoms in the di-, tri, tetra-, penta- or hexaradical chain must be separated from each other by at least two carbon atoms; or R is $-[CH_2CH_2O-]_p-$, wherein p is an integer from about 10 to about 50;

each a and b is independently an integer from about 0 to about 6;

each m, n, y, and z is independently an integer from about 2 to about 24;

w is an integer from about 2 to about 6; and c and d are each an integer from 1 to 5, with the proviso that the sum of c+d is an integer from about 2 to about 6.

In some other embodiments, the present invention is directed to linkers or pharmaceutically acceptable salts thereof of formula Iz, IIz, IIIz, IVz, or Vz:

$$R[-C(=O)-(Y)_a-O-R^{1b}]_w \qquad \text{Iz}$$

$$R[-(X)_a-OC(=O)-R^{2b}]_w \qquad \text{Iz}$$

$$R[-(Y)_a-O-R^{3b}]_w \qquad \text{IIIz}$$

$$R^4-O-(Y)_d-O-R^{4b} \qquad \text{IVz}$$

$$R[-(X)_a-O-R^{5b}]_w \qquad \text{Vz}$$

wherein:
each $-O-R^{1b}$, $-O-R^{3b}$, $-O-R^{4b}$, $R^{4b}-O-$, and $-O-R^{5b}$ is independently:

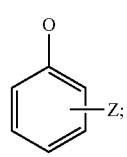

each —OC(=O)—$R^{2b}$ is independently:

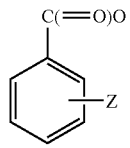

each Z is independently: $NH_2$, $NH(Y^1)_bH$, $N((X^1)_bH)_2$, NCO, $CH_2CO_2H$, or $CH=CHCO_2H$;
each X is independently:
—OC(=O)$CH_2$— (inverse glycolic acid moiety), —OC(=O)CH($CH_3$)— (inverse lactic acid moiety), —OC(=O)$CH_2OCH_2CH_2$— (inverse dioxanone acid moiety), —OC(=O)$CH_2CH_2CH_2CH_2CH_2$— (inverse caprolactone acid moiety), —OC(=O)$(CH_2)_y$—, or —OC(=O)$CH_2(OCH_2CH_2)_z$—.
each $X^1$ is independently:
—$CH_2$C(=O)O— (glycolic acid moiety), —CH($CH_3$)C(=O)O— (lactic acid moiety), —$CH_2CH_2OCH_2$C(=O)O— (dioxanone acid moiety), —$CH_2CH_2CH_2CH_2CH_2$C(=O)O— (caprolactone acid moiety), —$(CH_2)_y$C(=O)O—, or —$(CH_2CH_2O)_nCH_2$C(=O)O—;
each Y is independently:
—$OCH_2$C(=O)— (inverse glycolic ester moiety), —OCH($CH_3$)C(=O)— (inverse lactic ester moiety), —$OCH_2CH_2OCH_2$C(=O)— (inverse dioxanone ester moiety), —$OCH_2CH_2CH_2CH_2CH_2$C(=O)— (inverse caprolactone ester moiety), —O$(CH_2)_m$C(=O)—, or —O$(CH_2CH_2O)_nOCH_2$C(=O)—;
each $Y^1$ is independently:
—C(=O)$CH_2$O— (glycolic ester moiety), —C(=O)CH($CH_3$)O— (lactic ester moiety), —C(=O)$CH_2OCH_2CH_2$O— (dioxanone ester moiety), —C(=O)$CH_2CH_2CH_2CH_2CH_2$O— (caprolactone ester moiety), C(=O)$(CH_2)_m$O—, or —C(=O)$CH_2$—O—$(CH_2CH_2O)_n$—;
R is a di-, tri, tetra-, penta- or hexaradical derived from $C_{1-25}$ alkyl, aryl, or aryl-$(C_{1-6}alkyl)^{1-3}$—, wherein from 1-3 of the $CH_2$ groups within the alkyl chain are optionally independently replaced by O or S atoms, such that each of said O or S atoms is attached only to carbon atoms in the alkyl chain, with the proviso that multiple heteroatoms must be separated from each other and from the di-, tri-, tetra-, penta- or hexaradical chain ends by at least one carbon atom; or R is —[$CH_2CH_2$O—]$_p$—, wherein p is an integer from about 10 to about 50;
each a and b is independently an integer from about 1 to about 6;
each m, n, y, and z is independently an integer from about 2 to about 24;
w is an integer from about 2 to about 6; and
c and d are each an integer from 1 to 5, with the proviso that the sum of c+d is an integer from about 2 to about 6.
In certain other embodiments, the present invention is directed to compounds of formula Iz, IIz, IIIz, IVz, or Vz:

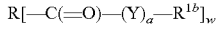 Iz

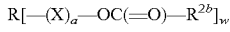 Iz

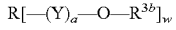 IIIz

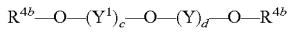 IVz

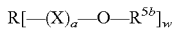 Vz wherein:
each $R^{1b}$, $R^{2b}$, $R^{3b}$, $R^{4b}$, and $R^{5b}$ is independently H, alkyl, or aralkyl;
each Z is independently: $NH_2$, $NH(Y^1)_bH$, $N((X^1)_bH)_2$, NCO, $CH_2CO_2H$, or $CH=CHCO_2H$;
each X is independently:
—OC(=O)$CH_2$— (inverse glycolic acid moiety), —OC(=O)CH($CH_3$)— (inverse lactic acid moiety), —OC(=O)$CH_2OCH_2CH_2$— (inverse dioxanone acid moiety), —OC(=O)$CH_2CH_2CH_2CH_2CH_2$— (inverse caprolactone acid moiety), —OC(=O)$(CH_2)_y$—, or —OC(=O)$CH_2(OCH_2CH_2)_z$—.
each $X^1$ is independently:
—$CH_2$C(=O)O— (glycolic acid moiety), —CH($CH_3$)C(=O)O— (lactic acid moiety), —$CH_2CH_2OCH_2$C(=O)O— (dioxanone acid moiety), —$CH_2CH_2CH_2CH_2CH_2$C(=O)O— (caprolactone acid moiety), —$(CH_2)_y$C(=O)O—, or —$(CH_2CH_2O)_nCH_2$C(=O)O—;
each Y is independently:
—$OCH_2$C(=O)— (inverse glycolic ester moiety), —OCH($CH_3$)C(=O)— (inverse lactic ester moiety), —$OCH_2CH_2OCH_2$C(=O)— (inverse dioxanone ester moiety), —$OCH_2CH_2CH_2CH_2CH_2$C(=O)— (inverse caprolactone ester moiety), —O$(CH_2)_m$C(=O)—, or —O$(CH_2CH_2O)_nOCH_2$C(=O)—;
each $Y^1$ is independently:
—C(=O)$CH_2$O— (glycolic ester moiety), —C(=O)CH($CH_3$)O— (lactic ester moiety), —C(=O)$CH_2OCH_2CH_2$O— (dioxanone ester moiety), —C(=O)$CH_2CH_2CH_2CH_2CH_2$O— (caprolactone ester moiety), C(=O)$(CH_2)_m$O—, or —C(=O)$CH_2$—O—$(CH_2CH_2O)_n$—;
R is a di-, tri, tetra-, penta- or hexaradical derived from $C_{1-25}$ alkyl, aryl, or aryl-$(C_{1-6}alkyl)_{1-3}$-, wherein from 1-3 of the $CH_2$ groups within the alkyl chain are optionally independently replaced by O or S atoms, such that each of said O or S atoms is attached only to carbon atoms in the alkyl chain, with the proviso that multiple heteroatoms must be separated from each other and from the di-, tri-, tetra-, penta- or hexaradical chain ends by at least one carbon atom; or R is —[$CH_2CH_2$O—]$_p$—, wherein p is an integer from about 10 to about 50;
each a and b is independently an integer from about 1 to about 6;
each m, n, y, and z is independently an integer from about 2 to about 24;
w is an integer from about 2 to about 6; and
c and d are each an integer from 1 to 5, with the proviso that the sum of c+d is an integer from about 2 to about 6.
In some preferred embodiments of linkers or pharmaceutically acceptable salts thereof of the present invention, the linkers or pharmaceutically acceptable salts thereof have formula II or IIz. In alternatively preferred embodiments, the linkers or pharmaceutically acceptable salts thereof have formula IV or IVz.
In certain preferred embodiments, the linkers or pharmaceutically acceptable salts thereof of formulas I, II, or III, have formulas Ia-f, IIa-h, and IIa-f respectively:

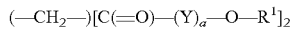 Ia;

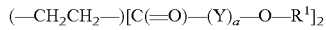 Ib;

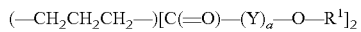 Ic;

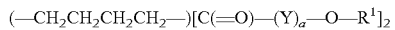 Id $(-CH_2CH_2-O-CH_2CH_2-)[C(=O)-(Y)_a-O-R^1]_2$     Ie;

$[-O(-CH_2CH_2-O-)_p][C(=O)-(Y)_a-O-R^1]_2$     If;

$(-CH_2-)[(X)_a-OC(=O)-R^2]_2$     IIa;

$(-CH_2CH_2-)[(X)_a-OC(=O)-R^2]_2$     IIb;

$(-CH_2CH_2CH_2-)[(X)_a-OC(=O)-R^2]_2$     IIc;

$(-CH_2CH_2CH_2CH_2-)[(X)_a-OC(=O)-R^2]_2$     IId;

$(-CH_2CH_2-O-CH_2CH_2-)[(X)_a-OC(=O)-R^2]_2$     IIe;

$(>C(H)-)[(X)_a-OC(=O)-R^2]_3$     IIf;

$(>C(CH_2CH_3)-)[(X)_a-OC(=O)-R^2]_3$     IIg;

$(>C<)[(X)_a-OC(=O)-R^2]_4$     IIh;

$(-CH_2-)[-(Y)_a-O-R^3]_2$     IIIa;

$(-CH_2CH_2-)[-(Y)_a-O-R^3]_2$     IIIb;

$(-CH_2CH_2CH_2-)[-(Y)_a-O-R^3]_2$     IIIc;

$(-CH_2CH_2CH_2CH_2-)[-(Y)_a-OR^3]_2$     IIId;

$(-CH_2CH_2-O-CH_2CH_2-)[-(Y)_a-O-R^3]_2$     IIIe; or $[-O(-CH_2CH_2-O-)_p][-(Y)_a-OR^3]_2$     IIIf.

In certain other preferred embodiments, the linkers or pharmaceutically acceptable salts thereof of formulas Iz, IIz, or IIIz, have formulas $Ia_1$-$f_1$, $IIa_1$-$h_1$, and $IIIa_1$-$f_1$ respectively:

$(-CH_2-)[C(=O)-(Y)_a-O-R^1]_2$     $Ia_1$;

$(-CH_2CH_2-)[C(=O)-(Y)_a-O-R^1]_2$     $Ib_1$;

$(-CH_2CH_2CH_2-)[C(=O)-(Y)_a-O-R^1]_2$     $Ic_1$;

$(-CH_2CH_2CH_2CH_2-)[C(=O)-(Y)_a-O-R^1]_2$     $Id_1$ $(-CH_2CH_2-O-CH_2CH_2-)[C(=O)-(Y)_a-O-R^1]_2$     $Ie_1$;

$[-O(-CH_2CH_2-O-)_p][C(=O)-(Y)_a-O-R^1]_2$     $If_1$;

$(-CH_2-)[(X)_a-OC(=O)-R^2]_2$     $IIa_1$;

$(-CH_2CH_2-)[(X)_a-OC(=O)-R^2]_2$     $IIb_1$;

$(-CH_2CH_2CH_2-)[(X)_a-OC(=O)-R^2]_2$     $IIc_1$;

$(-CH_2CH_2CH_2CH_2-)[(X)_a-OC(=O)-R^{2b}]_2$     $IId_1$;

$(-CH_2CH_2-O-CH_2CH_2-)[(X)_a-OC(=O)-R^{2b}]_2$     $IIe_1$;

$(>C(H)-)[(X)_a-OC(=O)-R^{2b}]_3$     $IIf_1$;

$(>C(CH_2CH_3)-)[(X)_a-OC(=O)-R^{2b}]_3$     $IIg_1$;

$(>C\leq)[(X)_a-OC(=O)-R^{2b}]_4$     $IIh_1$;

$(-CH_2-)[-(Y)_a-O-R^{3b}]_2$     $IIIa_1$;

$(-CH_2CH_2-)[-(Y)_a-O-R^{3b}]_2$     $IIIb_1$;

$(-CH_2CH_2CH_2-)[(Y)_a-O-R^{3b}]_2$     $IIIc_1$;

$(-CH_2CH_2CH_2CH_2-)[-(Y)_a-O-R^{3b}]_2$     $IIId_1$;

$(-CH_2CH_2-O-CH_2CH_2-)[-(Y)_a-O-R^{3b}]_2$     $IIIe_1$; or $[-O(-CH_2CH_2-O-)_p][-(Y)_a-O-R^{3b}]_2$     $IIIf_1$.

In certain preferred aspects of compounds, linkers or pharmaceutically acceptable salts thereof of formulas I, Iz, $Ia_1$-$f_1$, Ia-f, II, IIz, $IIa_1$-$h_1$, IIa-h, III, IIIz, $IIIa_1$-$f_1$, IIIa-f, IV, IVz, or Vz, the moieties X, $X^1$, Y, and/or $Y^1$ are each independently attached in the linkers by ester and/or ether linkages.

In compounds, linkers or pharmaceutically acceptable salts thereof of formula IV, the O between the two Y groups depicted as $(Y^1)-O-(Y)$ represents an ether linkage between the Y and $Y^1$ groups such that there is only one —O— ether moiety in the chain $(Y)-O(Y^1)$. By way of example, when $Y^1$ is corresponds to $-C(=O)CH_2O-$ (glycolic ester moiety), and Y corresponds to $-OCH(CH_3)C(=O)-$ (inverse lactic ester moiety), the resultant $(Y^1)-O-(Y)$ is $-C(=O)CH_2O-CH(CH_3)C(=O)-$. Similarly, when R is $-[CH_2CH_2O-]_p-$ and is connected to (Y), the resultant $R-(Y)$ is $-[CH_2CH_2O-]_p-CH(CH_3)C(=O)-$, when for example, $(Y^1)$ is $-OCH(CH_3)C(=O)-$.

In some preferred embodiments of compounds, linkers or pharmaceutically acceptable salts thereof of formula I, Iz, $Ia_1$-$f_1$, Ia-f, III, IIIz, $IIIa_1$-$f_1$, IIIa-f, IV, or IVz, Y and $Y^1$ are derived from different hydroxyacid or lactone precursors. As non-limiting examples, Y may be $-OCH(CH_3)C(=O)-$ (derived from lactic acid) and $Y^1$ may be $-C(=O)CH_2O-$ (derived from glycolic acid), or Y may be derived from glycolic acid and $Y^1$ may be derived from caprolactone.

In some preferred embodiments of compounds, linkers or pharmaceutically acceptable salts thereof of formula II, IIz, $IIa_1$-$h_1$, IIa-h, or Vz, X and $X^1$ are derived from different hydroxyacid or lactone precursors. As non-limiting examples, X may be $-OC(=O)CH(CH_3)-$ (derived from lactic acid) and $X^1$ may be $-CH_2C(=O)O-$ (derived from glycolic acid), or X may be derived from glycolic acid and $X^1$ may be derived from caprolactone.

In other preferred embodiments of compounds, linkers or pharmaceutically acceptable salts thereof of formulas I, Iz, $Ia_1$-$f_1$, Ia-f, II, IIz, $IIa_1$-$h_1$, IIa-h, III, IIIz, $IIIa_1$-$f_1$, IIIa-f, IV, IVz, or Vz, R is a di-, tri, tetra-, penta- or hexaradical derived from $C_{1-25}$ alkyl, aryl, preferably phenyl, or aryl-$(C_{1-6}$ alkyl$)_{1-3}$-, preferably phenyl-$(C_{1-6}$ alkyl$)_{1-3}$-. Whether R is a di-, tri, tetra-, penta- or hexaradical is determined by w. For example, when w is 2, R is a diradical; when w is 4, R is a tetraradical, and so forth. In certain preferred embodiments wherein R is derived from $C_{1-25}$ alkyl or aryl-$(C_{1-6}$ alkyl$)_{1-3}$-, 1-4 of the $CH_2$ groups, preferably 1-3 of the $CH_2$ groups, within the alkyl chain are optionally independently replaced by O or S atoms, preferably by O atoms, such that each of said O or S atoms is attached only to carbon atoms in the alkyl chain, preferably with the proviso that the O or S atoms are separated from the di-, tri, tetra-, penta- or hexaradical chain ends by at least one carbon atom and that multiple O or S atoms in the diradical chain must be separated from each other by at least two carbon atoms. Alternatively in some preferred embodiments, when R is alkyl, it is more preferably $(CH_2)$, $(CH_2)_3$, $CH(CH_2)_3$, $C(CH_2)_4$, or $C(CH_2CH_3)(CH_2)_3$. In still other preferred embodiments, R is $(CH_2)_3$, and wherein the C-2 $CH_2$ group within the $(CH_2)_3$ chain is optionally replaced by an O atom. In yet other preferred embodiments, R is $(CH_2)_2$, $(CH_2)_3$, $(CH_2)_4$, $(CH_2OCH_2)$, or $(CH_2CH_2OCH_2CH_2)$. In still other preferred embodiments, R is $(CH_2CHCH_2)$ when w is 3, or $(C(CH_2)_4)$ when w is 4.

Alternatively, R is $-[CH_2CH_2O-]_p-$, wherein p is an integer from about 10 to about 50, preferably from about 10 to about 30, more preferably from about 10 to about 20. As used herein for linear and multiarmed hydrolysable linkers and cross linkers of formulas I, II, or III, when R is —[CH$_2$CH$_2$O—]$_p$—, the two oxygen atoms in the moiety "O—R—O" are implicit in the R moiety. For example, the terminal oxygen atoms in the diradical —O—CH$_2$CH$_2$—O—CH$_2$CH$_2$—O— (that is, wherein R is —[CH$_2$CH$_2$O—]$_p$— and p is 2) form part of both the R and the two "O" atom functions. Thus when R is —[CH$_2$CH$_2$O—]$_p$— and p is 2) the hydrolysable linkers of formula II have the formula:

R$^2$—C(=O)O—(X$^1$)$_a$—O—CH$_2$CH$_2$—O—CH$_2$CH$_2$—O—(X)$_a$—OC(=O)—R$^2$.

As used herein, the term "aryl-(C$_{1-6}$ alkyl)$_{1-3}$-" refers to a aryl ring, preferably a benzene ring, having 1 to 3 pendant alkyl groups, wherein the aryl-(C$_{1-6}$ alkyl)$_{1-3}$-, preferably phenyl-(C$_{1-6}$ alkyl)$_{1-3}$-moiety, is attached to the remainder of the structure in a given formula through its pendant alkyl group(s).

In certain embodiments of compounds, linkers or pharmaceutically acceptable salts thereof of the invention, such as for example formulas I, Iz, Ia$_1$-f$_1$, Ia-f, II, IIz, IIa$_1$-h$_1$, IIa-h, III, IIIz, IIIa$_1$-f$_1$, IIIa-f, or Vz, each a is independently an integer from about 0 to about 6, preferably wherein at least one a is an integer from 1 to about 6, more preferably from 1 to about 3. Alternatively preferred, each a is independently an integer from about 1 to about 6, preferably from 1 to about 3, with from 1 to about 2 being even more preferred.

In some other embodiments of compounds, linkers or pharmaceutically acceptable salts thereof of the invention, such as for example formulas I, Iz, Ia$_1$-f$_1$, Ia-f, II, IIz, IIa$_1$-h$_1$, IIa-h, III, IIIz, IIIa$_1$-f$_1$, IIIa-f, IV, IVz, or Vz, each b is independently an integer from about 0 to about 6, preferably wherein at least one b is an integer from 1 to about 6, more preferably from 1 to about 3. Alternatively preferred, each b is independently an integer from about 1 to about 6, preferably from 1 to about 3, with from 1 to about 2 being even more preferred.

In certain other preferred embodiments of compounds, linkers or pharmaceutically acceptable salts thereof of formulas I, Iz, Ia$_1$-f$_1$, Ia-f, II, IIz, IIIa$_1$-h$_1$, IIa-h, III, IIIz, IIIa$_1$-f$_1$, IIIa-f, or Vz, w is an integer from about 2 to about 4.

In certain preferred embodiments of compounds, linkers or pharmaceutically acceptable salts thereof of the invention, c and d are each 1, 2, or 3; more preferably both c and d are 1, or they are both 2, or they are both 3.

In still other preferred embodiments of compounds, linkers or pharmaceutically acceptable salts thereof of formula II, IIz, IIa$_1$-h$_1$, or IIa-h, each X is independently —OC(=O)CH$_2$—, —OC(=O)CH(CH$_3$)—, —OC(=O)CH$_2$OCH$_2$CH$_2$—, or —OC(=O)CH$_2$CH$_2$CH$_2$CH$_2$CH$_2$—; more preferably —OC(=O)CH$_2$— or —OC(=O)CH(CH$_3$)—.

In some other preferred embodiments of compounds, linkers or pharmaceutically acceptable salts thereof of formulas II, IIz, IIa$_1$-h$_1$, or IIa-h, each X$^1$ is independently —CH$_2$C(=O)O—, —CH(CH$_3$)C(=O)O—, —CH$_2$CH$_2$OCH$_2$C(=O)O—, or —CH$_2$CH$_2$CH$_2$CH$_2$CH$_2$C(=O)O—, more preferably —CH$_2$C(=O)O— or —CH(CH$_3$)C(=O)O—.

In some preferred embodiments of compounds, linkers or pharmaceutically acceptable salts thereof of formulas I, Iz, Ia$_1$-f$_1$, Ia-f, III, IIIz, IIIa$_1$-f$_1$, IIIa-f, IV, or IVz, each Y is independently —OCH$_2$C(=O)—, —OCH(CH$_3$)C(=O)—, —OCH$_2$CH$_2$OCH$_2$C(=O)—, or —OCH$_2$CH$_2$CH$_2$CH$_2$CH$_2$C(=O)—, more preferably —OCH$_2$C(=O)— or —OCH(CH$_3$)C(=O)—.

In certain preferred embodiments of compounds, linkers or pharmaceutically acceptable salts thereof of formula I, Iz, Ia$_1$-f$_1$, Ia-f, II, IIz, IIIa$_1$-h$_1$, IIa-h, III, IIIz, IIIa$_1$-f$_1$, IIIa-f, IV, or IVz, each Y$^1$ is independently —C(=O)CH$_2$O—, —C(=O)CH(CH$_3$)O—, —C(=O)CH$_2$OCH$_2$CH$_2$O—, or —C(=O)CH$_2$CH$_2$CH$_2$CH$_2$CH$_2$O—; more preferably —C(=O)CH$_2$O— or —C(=O)CH(CH$_3$)O—.

Certain embodiments of the invention are directed to linkers or pharmaceutically acceptable salts thereof of formula I, Iz, II, IIz, III, IIIz, IV, IVz, or Vz having a Z-substituted phenyl ring, wherein the Z moiety is present as a substituent on the phenyl ring of R$^1$, R$^2$, R$^3$, or R$^4$. The ring position of the Z moiety in relation to the oxy or carboxy group also attached to the phenyl ring is not critical, and may be located ortho, meta, or para to the carboxy group of R$^2$ or the oxy group of R$^1$, R$^3$, or R$^4$. Preferably, Z is positioned meta or para, more preferably para to said carboxy or oxy group.

Other embodiments of the present invention are directed to polyesters of the formula:

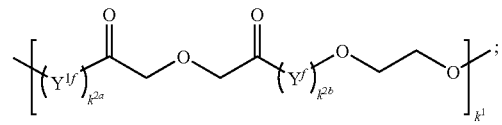

wherein:
each Y$^{1f}$ is independently —C(=O)CH$_2$O—, —C(=O)CH(CH$_3$)O—, —C(=O)CH$_2$OCH$_2$CH$_2$O—, —C(=O)CH$_2$CH$_2$CH$_2$CH$_2$CH$_2$O—, —C(=O)(CH$_2$)$_m$O—, or —C(=O)CH$_2$—O—(CH$_2$CH$_2$O)$_n$—;
each Y$^f$ is independently —OCH$_2$C(=O)—, —OCH(CH$_3$)C(=O)—, —OCH$_2$CH$_2$OCH$_2$C(=O)—, —OCH$_2$CH$_2$CH$_2$CH$_2$CH$_2$C(=O)—, —O(CH$_2$)$_m$C(=O)—, or —O(CH$_2$CH$_2$O)$_n$OCH$_2$C(=O)—;
each m and n is independently an integer from about 2 to about 24;
k$^1$ is an integer from about 100 to about 5000; and
each k$^{2a}$ and k$^{2b}$ is independently 1 to about 5.

In some preferred embodiments of the polyesters of the present invention, Y$^f$ and Y$^{1f}$ are derived from different hydroxyacid or lactone precursors. As non-limiting examples, Y$^f$ may be —OCH(CH$_3$)C(=O)— (derived from lactic acid) and Y$^{1f}$ may be —C(=O)CH$_2$O— (derived from glycolic acid), or Y$^f$ may be derived from glycolic acid and Y$^{1f}$ may be derived from caprolactone.

In certain preferred embodiments of the polyesters of the present invention, each k$^{2a}$ is independently an integer from about 1 to about 5, preferably wherein at least one a is an integer from 1 to about 5, more preferably from 1 to about 3. Alternatively preferred, each k$^{2a}$ is independently an integer from about 1 to about 5, preferably from 1 to about 3, with from 1 to about 2 being even more preferred.

In certain other preferred embodiments of the polyesters of the present invention, each k$^{2b}$ is independently an integer from about 1 to about 5, preferably wherein at least one a is an integer from 1 to about 5, more preferably from 1 to about 3. Alternatively preferred, each k$^{2b}$ is independently an integer from about 1 to about 5, preferably from 1 to about 3, with from 1 to about 2 being even more preferred.

In some other preferred embodiments of the polyesters of the present invention, each Y$^f$ is independently —OCH$_2$C(=O)—, —OCH(CH$_3$)C(=O)—, —OCH$_2$CH$_2$OCH$_2$C(=O)—, or —OCH$_2$CH$_2$CH$_2$CH$_2$CH$_2$C(=O)—, more preferably —OCH$_2$C(=O)— or —OCH(CH$_3$)C(=O)—.

In yet other preferred embodiments of the polyesters of the present invention, each Y$^{1f}$ is independently —C(=O)CH$_2$O—, —C(=O)CH(CH$_3$)O—, —C(=O)CH$_2$OCH$_2$CH$_2$O—, or —C(=O)

$CH_2CH_2CH_2CH_2CH_2O$—; more preferably —$C(=O)$ $CH_2O$— or —$C(=O)CH(CH_3)O$—.

In other embodiments, the present invention is directed to compounds of formula Iva:

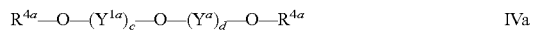

wherein:
each $Y^{1a}$ is independently:
—$C(=O)CH_2O$—, —$C(=O)CH(CH_3)O$—, —$C(=O)CH_2OCH_2CH_2O$—, —$C(=O)$ $CH_2CH_2CH_2CH_2CH_2O$—, —$C(=O)(CH_2)_mO$—, or —$C(=O)CH_2$—O—$(CH_2CH_2O)_n$—;

each $Y^a$ is independently:
—$OCH_2C(=O)$—, —$OCH(CH_3)C(=O)$—, —$OCH_2CH_2OCH_2C(=O)$—, —$OCH_2CH_2CH_2CH_2CH_2C(=O)$—, —$O(CH_2)_m$ $C(=O)$—, or —$O(CH_2CH_2O)_nOCH_2C(=O)$—;

each $R^{4a}$ is independently H, alkyl, or aralkyl;
each m and n is independently an integer from about 2 to about 24; and
c and d are each an integer from 1 to 5, with the proviso that the sum of c+d is an integer from about 2 to about 6.

In some preferred embodiments of compounds of formula IVa, the O between the two Y groups depicted as $(Y^{1a})$—O—$(Y^a)$ represents an ether linkage between the $Y^{1a}$ and $Y^a$ groups such that there is only one —O— ether moiety between the two groups. By way of example, when $Y^{1a}$ is corresponds to —$C(=O)CH_2O$— (glycolic ester moiety), and $Y^a$ corresponds to —$OCH(CH_3)C(=O)$— (inverse lactic ester moiety), the resultant $(Y^{1a})$—O—$(Y^a)$ is —$COCH_2O$—$CH(CH_3)C(=O)$—.

In other preferred embodiments of compounds of formula IVa, $Y^{1a}$ and $Y^a$ are derived from different hydroxyacid or lactone precursors. As non-limiting examples, $Y^{1a}$ may be —$C(=O)CH_2O$— (derived from glycolic acid) is and $Y^a$ may be —$OCH(CH_3)C(=O)$— (derived from lactic acid), or $Y^{1a}$ may be derived from lactic acid and $Y^a$ may be derived from caprolactone.

In certain preferred embodiments of compounds of formula IVa, each $Y^{1a}$ is independently —$C(=O)CH_2O$—, —$C(=O)CH(CH_3)O$—, —$C(=O)CH_2OCH_2CH_2O$—, or —$C(=O)CH_2CH_2CH_2CH_2CH_2O$—; more preferably —$C(=O)CH_2O$— or —$C(=O)CH(CH_3)O$—

In certain other preferred embodiments of compounds of formula IVa, each $Y^a$ is independently —$OCH_2C(=O)$—, —$OCH(CH_3)C(=O)$—, —$OCH_2CH_2OCH_2C(=O)$—, or —$OCH_2CH_2CH_2CH_2CH_2C(=O)$—, more preferably —$OCH_2C(=O)$— or —$OCH(CH_3)C(=O)$—.

In some preferred embodiments of compounds of formula Iva, when $R^{4a}$ is alkyl, it is preferably $C_{1-12}$ alkyl, more preferably $C_{1-6}$, still more preferably $C_{1-3}$, with $C_1$ being even more preferred. When $R^{4a}$ is aralkyl, it is preferably phenyl-$(C_{1-6}$ alkyl), more preferably phenyl-)$(C_{1-3}$alkyl), with benzyl being even more preferred.

The present invention also provides linear and multiarmed hydrolysable monomeric and oligomeric linkers of formulas V, VI, VII, VIII, or IX as shown below derived from symmetrical or unsymmetrical diacids of formula A.

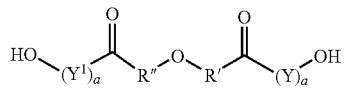

A

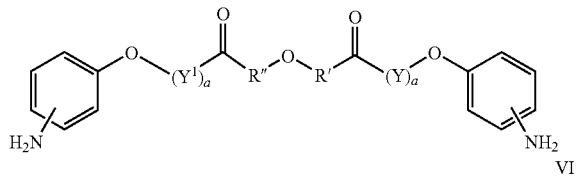

V

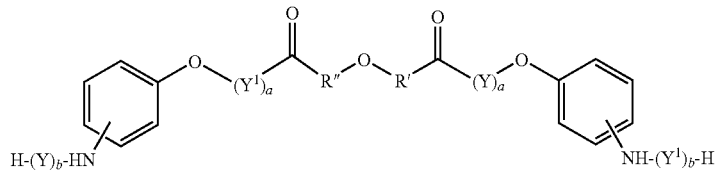

VI

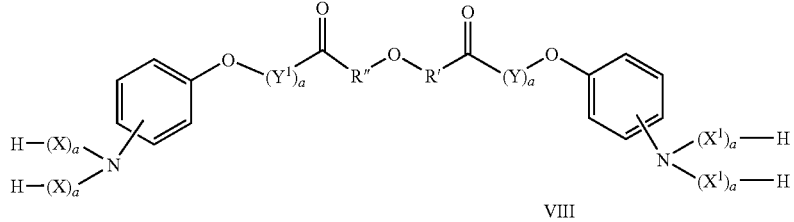

VII

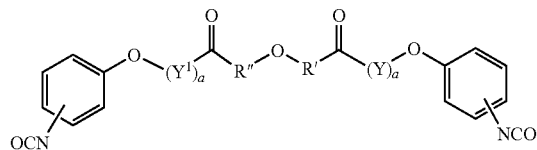

VIII

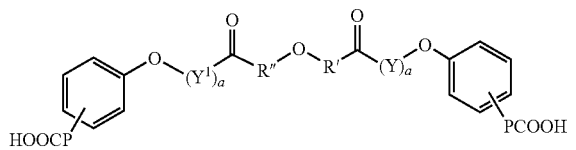

IX wherein:
R' and R" are each independently a $C_{1-24}$alkylene diradical, wherein from 1-4 of the $CH_2$ groups, preferably 1-3 of the $CH_2$ groups, within the alkyl chain are optionally independently replaced by O or S atoms, such that each of said O or S atoms is attached only to carbon atoms in the alkyl chain, with the proviso that multiple heteroatoms must be separated from each other and from the diradical chain ends by at least one carbon atom;

P is a —CH$_2$— or —CH=CH— group;

each a is independently an integer from about 0 to about 6;

each b is independently an integer from about 1 to about 6;

each X is independently:
- —OC(=O)CH$_2$— (inverse glycolic acid moiety), —OC(=O)CH(CH$_3$)— (inverse lactic acid moiety), —OC(=O)CH$_2$OCH$_2$CH$_2$— (inverse dioxanone acid moiety), —OC(=O)CH$_2$CH$_2$CH$_2$CH$_2$CH$_2$— (inverse caprolactone acid moiety), —OC(=O)(CH$_2$)$_y$—, or —OC(=O)CH$_2$(OCH$_2$CH$_2$)$_n$—; preferably —OC(=O)CH$_2$—, —OC(=O)CH(CH$_3$)—, —OC(=O)CH$_2$OCH$_2$CH$_2$—, or —OC(=O)CH$_2$CH$_2$CH$_2$CH$_2$CH$_2$—; more preferably —OC(=O)CH$_2$— or —OC(=O)CH(CH$_3$)—;

each X$^1$ is independently:
- —CH$_2$C(=O)O— (glycolic acid moiety), —CH(CH$_3$)C(=O)O— (lactic acid moiety), —CH$_2$CH$_2$OCH$_2$C(=O)O— (dioxanone acid moiety), —CH$_2$CH$_2$CH$_2$CH$_2$CH$_2$C(=O)O— (caprolactone acid moiety), —(CH$_2$)$_y$C(=O)O—, or —(CH$_2$CH$_2$O)$_n$CH$_2$C(=O)O—; preferably —CH$_2$C(=O)O—, —CH(CH$_3$)C(=O)O—, —CH$_2$CH$_2$OCH$_2$C(=O)O—, or —CH$_2$CH$_2$CH$_2$CH$_2$CH$_2$C(=O)O—, more preferably —CH$_2$C(=O)O— or —CH(CH$_3$)C(=O)O—;

each Y is independently:
- —OCH$_2$C(=O)— (inverse glycolic ester moiety), —OCH(CH$_3$)C(=O)— (inverse lactic ester moiety), —OCH$_2$CH$_2$OCH$_2$C(=O)— (inverse dioxanone ester moiety), —OCH$_2$CH$_2$CH$_2$CH$_2$CH$_2$C(=O)— (inverse caprolactone ester moiety), —O(CH$_2$)$_m$C(=O)—, or —O(CH$_2$CH$_2$O)$_n$OCH$_2$C(=O)—; preferably —OCH$_2$C(=O)—, —OCH(CH$_3$)C(=O)—, —OCH$_2$CH$_2$OCH$_2$C(=O)—, or —OCH$_2$CH$_2$CH$_2$CH$_2$CH$_2$C(=O)—, more preferably —OCH$_2$C(=O)— or —OCH(CH$_3$)C(=O)—;

each Y$^1$ is independently:
- —C(=O)CH$_2$O— (glycolic ester moiety), —C(=O)CH(CH$_3$)O— (lactic ester moiety), —C(=O)CH$_2$OCH$_2$CH$_2$O— (dioxanone ester moiety), —C(=O)CH$_2$CH$_2$CH$_2$CH$_2$CH$_2$O— (caprolactone ester moiety), —C(=O)(CH$_2$)$_m$O—, or —C(=O)CH$_2$—O—(CH$_2$CH$_2$O)$_n$—; preferably —C(=O)CH$_2$O—, —C(=O)CH(CH$_3$)O—, —C(=O)CH$_2$OCH$_2$CH$_2$O—, or —C(=O)CH$_2$CH$_2$CH$_2$CH$_2$CH$_2$O—; more preferably —C(=O)CH$_2$O— or —C(=O)CH(CH$_3$)O—; and each m, n, y, and z is independently an integer from about 2 to about 24.

The symmetrical or unsymmetrical diacid linker of formula A of the present invention can be derived from the symmetrical or unsymmetrical diacid linker precursor of formula L, wherein R' and R" are as herein defined.

HOOC—R"—O—R'—COOH

The linear and multiarmed hydrolysable monomeric and oligomeric linkers of the general formula V, VI, VII, VIII, or IX of the present invention can be derived from symmetrical or unsymmetrical diacid of formula A of the present invention according to Scheme 1 as shown below:

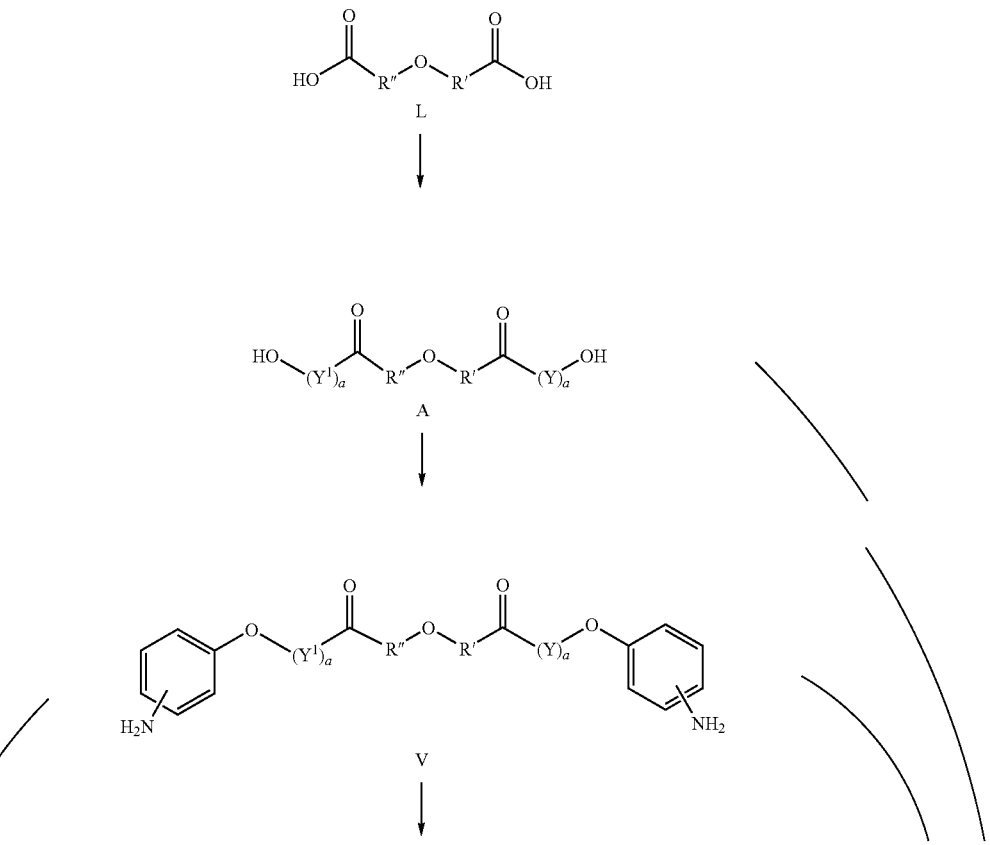

-continued

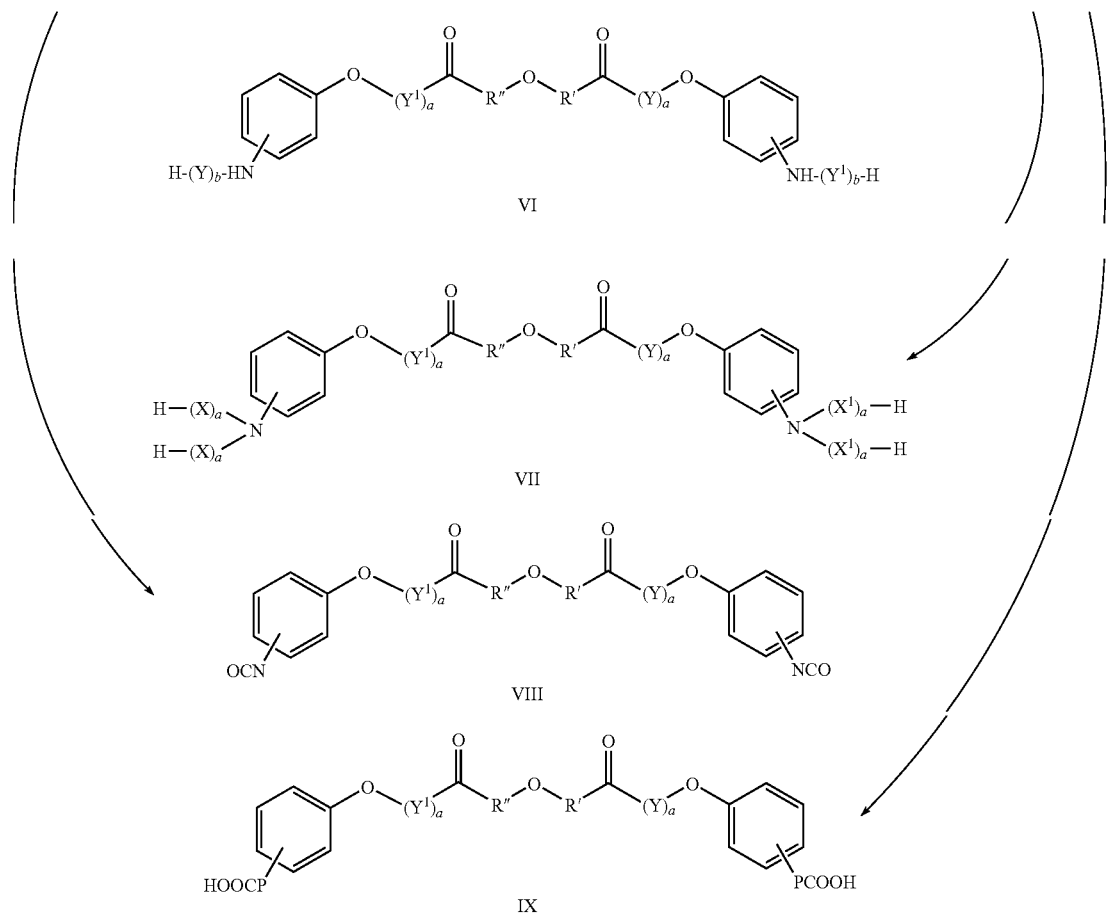

A few examples of structures of symmetrical or unsymmetrical diacid linker precursor of formula L are given below.

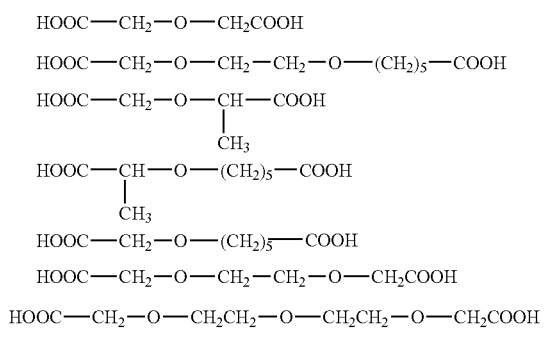

n = 10-50

Structures of Symmetrical and Unsymmetrical Diacid Linker Precursors

A few examples of structures of symmetrical or unsymmetrical hydrolysable diacid linkers of formula A of the present invention are given below

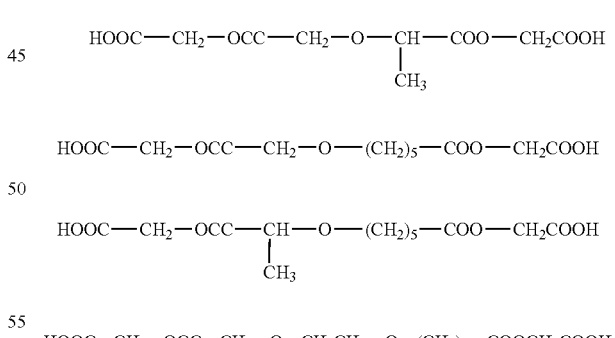

Structures of Symmetrical and Unsymmetrical Diacid Linkers

A few examples of structures of hydrolysable linker and crosslinker amines derived from symmetrical or unsymmetrical ether diacids of formula A of the present invention are given below.

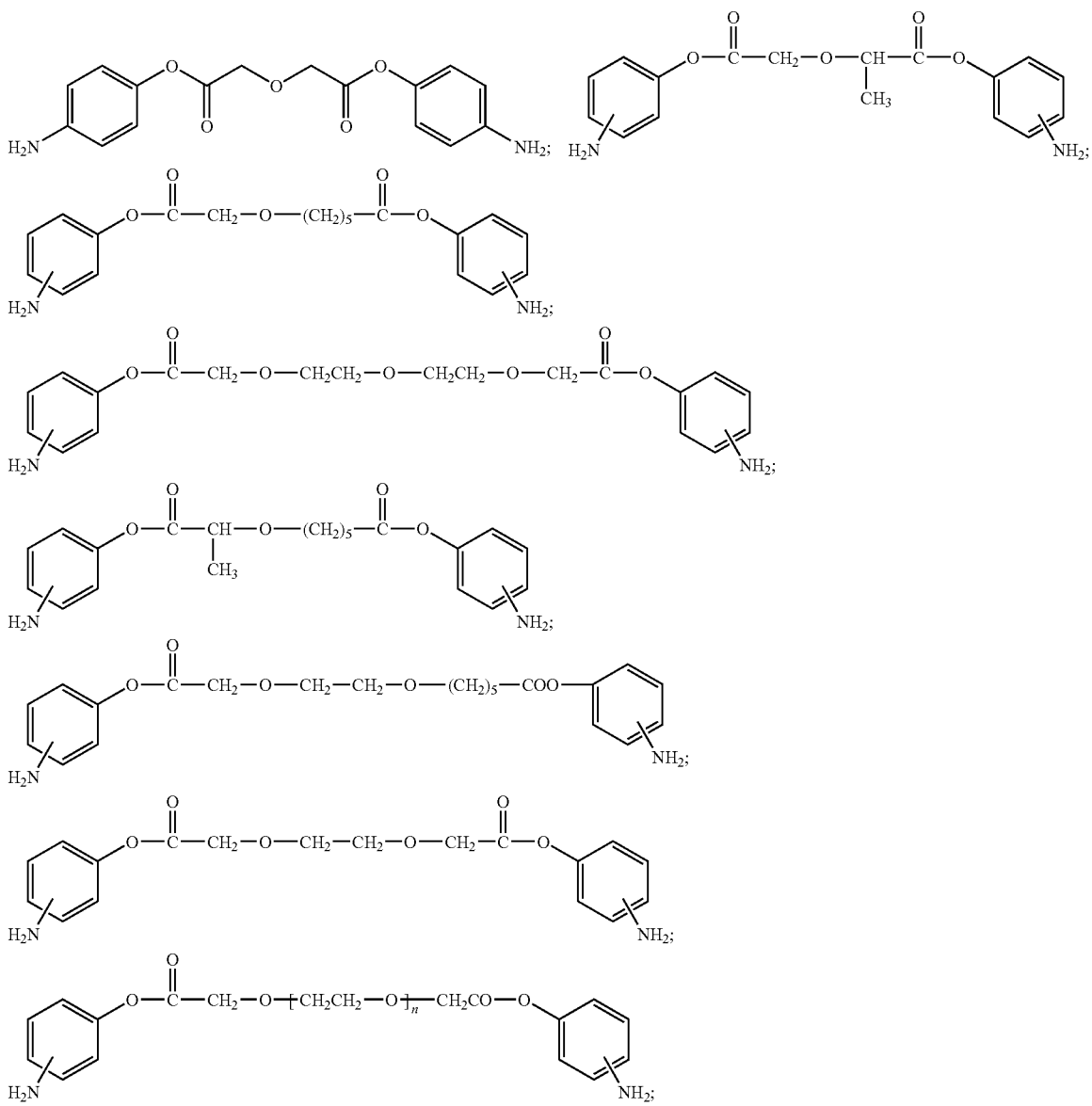
wherein n is an integer from about 10 to about 50
Hydrolysable Linker and Crosslinker Amines of Formula V of the Present Invention Derived From Symmetrical/Unsymmetrical Ether Diacids
A few examples of structures of hydrolysable symmetrical and unsymmetrical linker amide diols are shown below.
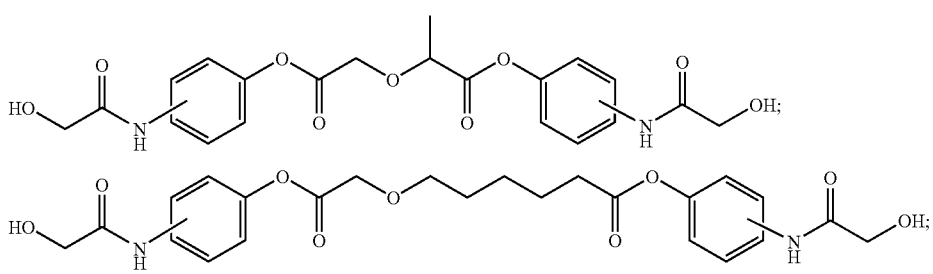

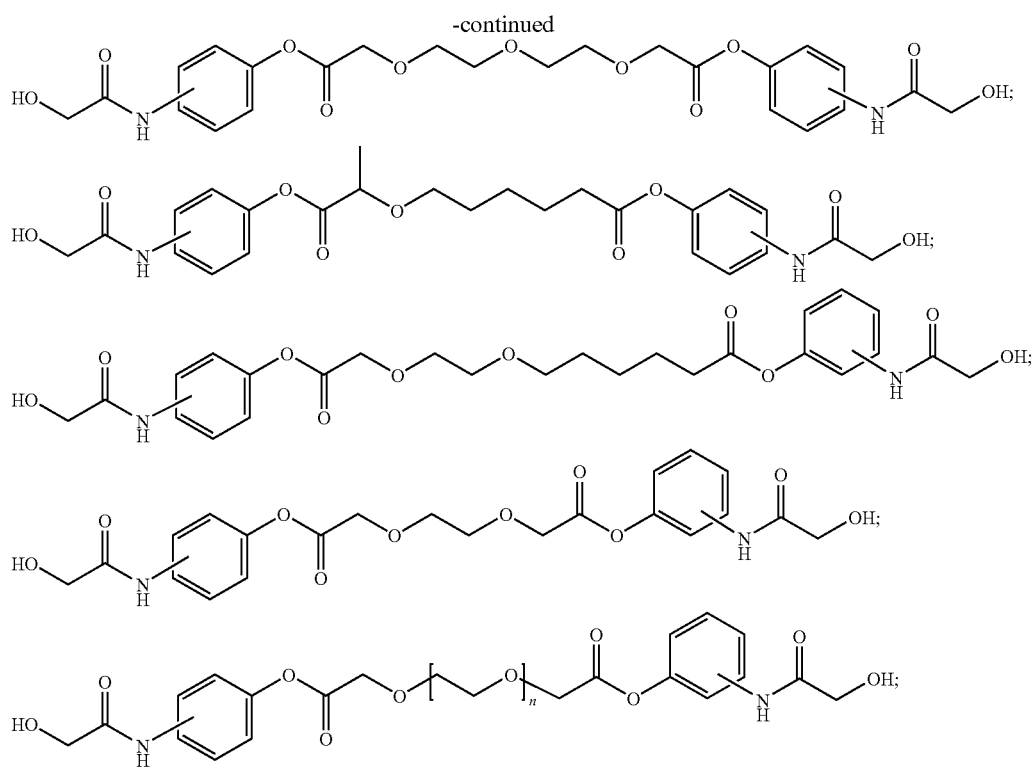

wherein n is an integer from about 10 to about 50, preferably about 10 to about 30; more preferably about 10 to about 20; still more preferably about 10 to about 12.

Hydrolysable Linker Amide Alcohols of Formula VI of the Present Invention Derived from Symmetrical/Unsymmetrical Ether Diacids A few examples of structures of hydrolysable symmetrical and unsymmetrical linker and crosslinker amine acids are shown below.

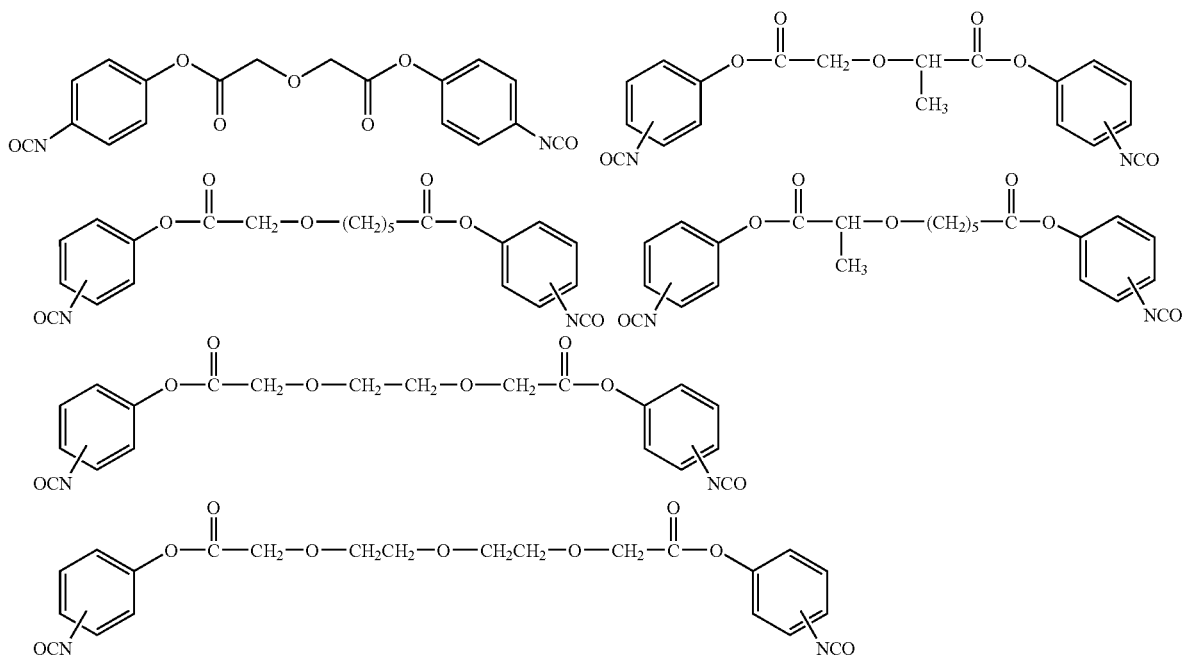

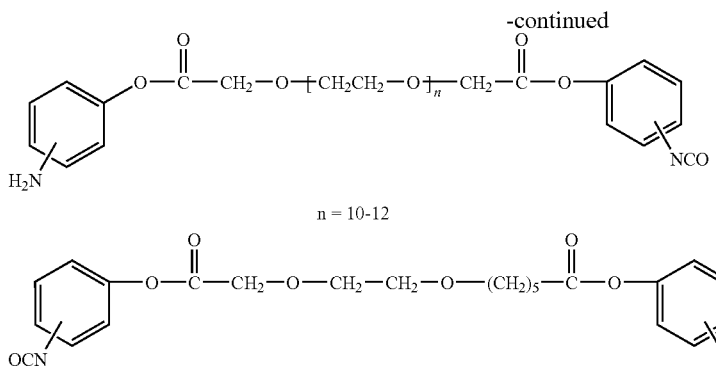
n = 10-12
Hydrolysable Linker and Crosslinker Isocyanates of Formula VII of the Present Invention Derived from Symmetrical/Unsymmetrical Ether Diacids
A few examples of structures of hydrolysable linker and crosslinker amine acids derived from symmetrical and unsymmetrical ether diacids are shown below.
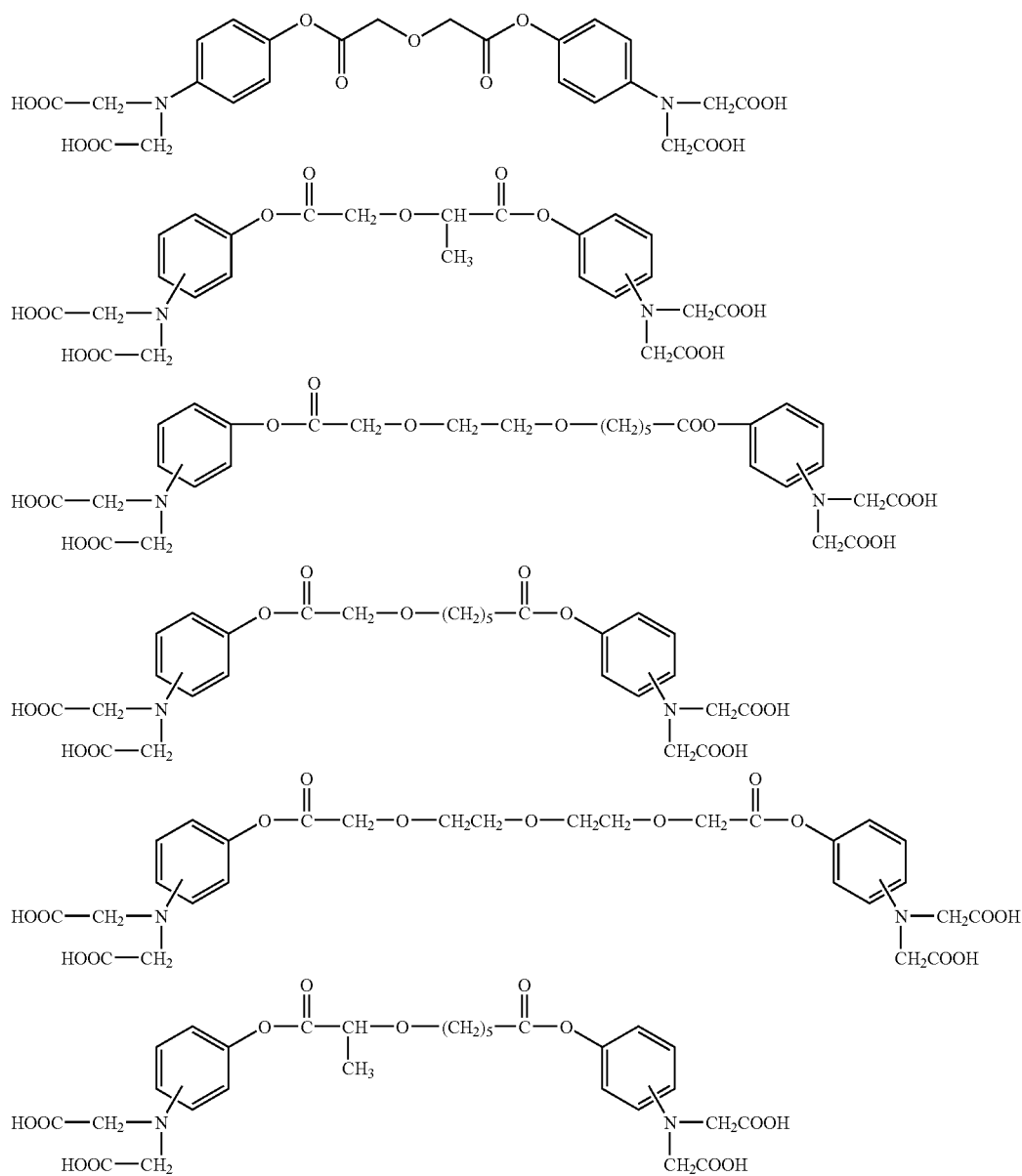

-continued

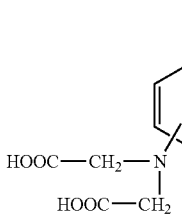 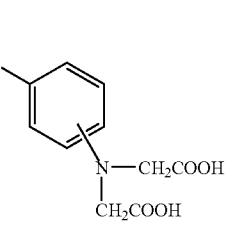

Hydrolysable Linker and Crosslinker Amine Acids of Formula VIII of the Present Invention Derived from Symmetrical/Unsymmetrical Ether Diacids The present invention also provides linear and multiarmed hydrolysable monomeric and oligomeric linkers of formulas X, XI, and XII, as shown below derived from linear or branched precursor of formula B.

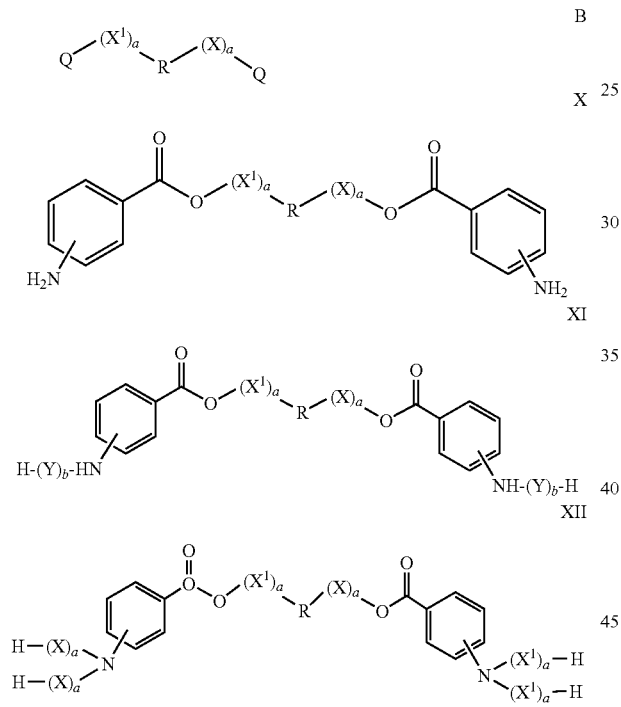

wherein:
R is a di-, tri, tetra-, penta- or hexaradical derived from $C_{1-25}$ alkyl, aryl, or aryl-$(C_{1-6}alkyl)_{1-3}$-, wherein from 1-4 of the $CH_2$ groups, preferably from 1-3 of the $CH_2$ groups, within the alkyl chain are optionally independently replaced by O or S atoms, preferably by O atoms, such that each of said O or S atoms is attached only to carbon atoms in the alkyl chain, with the proviso that the O or S atoms are separated from the di-, tri, tetra-, penta- or hexaradical chain ends by at least one carbon atom and that multiple O or S atoms in the di-, tri, tetra-, penta- or hexaradical chain must be separated from each other by at least two carbon atoms;

Q is a halogen (e.g., F, Cl, Br and I);
each a and b is independently an integer from about 1 to about 6;
each X is independently:
—OC(=O)$CH_2$— (inverse glycolic acid moiety),
—OC(=O)CH($CH_3$)— (inverse lactic acid moiety),
—OC(=O)$CH_2OCH_2CH_2$— (inverse dioxanone acid moiety), —OC(=O)$CH_2CH_2CH_2CH_2CH_2$— (inverse caprolactone acid moiety), —OC(=O)$(CH_2)_y$—, or —OC(=O)$CH_2(OCH_2CH_2)_n$—; preferably —OC(=O)$CH_2$—, —OC(=O)CH($CH_3$)—, —OC(=O)$CH_2OCH_2CH_2$—, or —OC(=O)$CH_2CH_2CH_2CH_2CH_2$—; more preferably —OC(=O)$CH_2$— or —OC(=O)CH($CH_3$)—;

each $X^1$ is independently:
—$CH_2$C(=O)O— (glycolic acid moiety), —CH($CH_3$)C(=O)O— (lactic acid moiety), —$CH_2CH_2OCH_2$C(=O)O— (dioxanone acid moiety), —$CH_2CH_2CH_2CH_2CH_2$C(=O)O— (caprolactone acid moiety), —$(CH_2)_y$C(=O)O—, or —$(CH_2CH_2O)_nCH_2$C(=O)O—; preferably —$CH_2$C(=O)O—, —CH($CH_3$)C(=O)O—, —$CH_2CH_2OCH_2$C(=O)O—, or —$CH_2CH_2CH_2CH_2CH_2$C(=O)O—, more preferably —$CH_2$C(=O)O— or —CH($CH_3$)C(=O)O—;

each Y is independently:
—$OCH_2$C(=O)— (inverse glycolic ester moiety), —OCH($CH_3$)C(=O)— (inverse lactic ester moiety), —$OCH_2CH_2OCH_2$C(=O)— (inverse dioxanone ester moiety), —$OCH_2CH_2CH_2CH_2CH_2$C(=O)— (inverse caprolactone ester moiety), —O$(CH_2)_m$C(=O)—, or —O$(CH_2CH_2O)_nOCH_2$C(=O)—; preferably —$OCH_2$C(=O)—, —OCH($CH_3$)C(=O)—, —$OCH_2CH_2OCH_2$C(=O)—, or —$OCH_2CH_2CH_2CH_2CH_2$C(=O)—, more preferably —$OCH_2$C(=O)— or —OCH($CH_3$)C(=O)—;

each $Y^1$ is independently:
—C(=O)$CH_2$O— (glycolic ester moiety), —C(=O)CH($CH_3$)O— (lactic ester moiety), —C(=O)$CH_2OCH_2CH_2$O— (dioxanone ester moiety), —C(=O)$CH_2CH_2CH_2CH_2CH_2$O— (caprolactone ester moiety), —C(=O)$(CH_2)_m$O—, or —C(=O)$CH_2$—O—$(CH_2CH_2O)_n$—; preferably —C(=O)$CH_2$O—, —C(=O)CH($CH_3$)O—, —C(=O)$CH_2OCH_2CH_2$O—, or —C(=O)$CH_2CH_2CH_2CH_2CH_2$O—; more preferably —C(=O)$CH_2$O— or —C(=O)CH($CH_3$)O—; and each m, n, y, and z is independently an integer from about 2 to about 24.

The linear or branched precursor of formula B of the present invention is derived from diol of formula M, wherein R is as defined herein.

$$HO—R—OH \qquad M$$

The linear and multiarmed hydrolysable monomeric and oligomeric linkers of the general formula X, XI, or XII of the present invention are derived from symmetrical or unsymmetrical diols of formula B of the present invention as shown below in Scheme 2, wherein Q, $X^1$, X, Y, $Y^1$, a, b, and R are as previously defined.

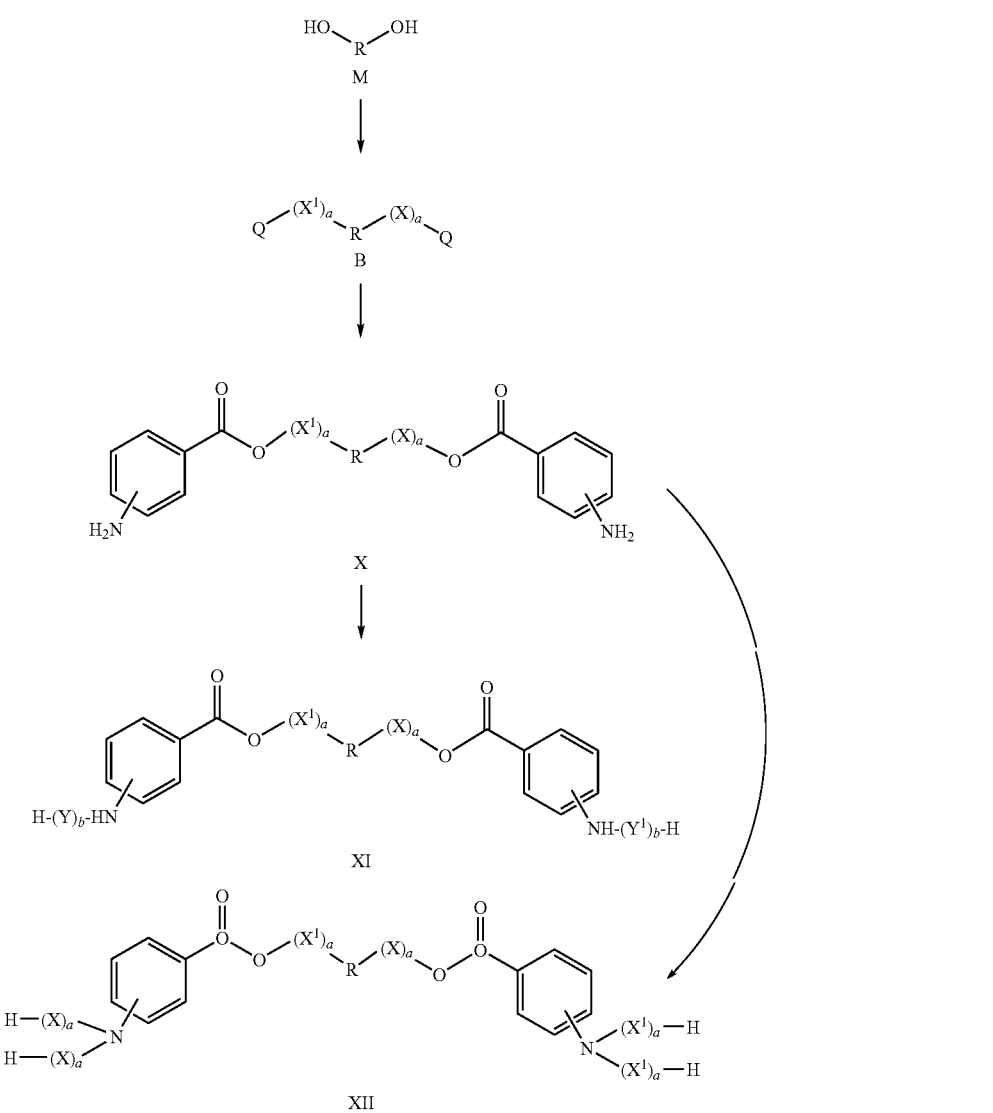
A few examples of structures of hydrolysable linkers of formula B of the present invention are given below.
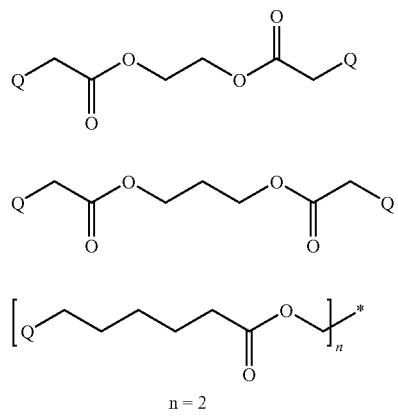

Hydrolysable Linkers of Formula B of the Present Invention where Q is a Halogen Atom Such as F, Cl, Br or I.

A few examples of structures of linear or branched hydrolysable linker and crosslinker amines of formula X of the present invention derived from p-amino benzoic acid are shown below.

Hydrolysable Linker and Crosslinker Amines of Formula X of the Present Invention Derived From Symmetrical/Unsymmetrical Ether Diacids A few examples of structures of hydrolysable linker and crosslinker amide alcohols of formula XI of the present invention are shown below.

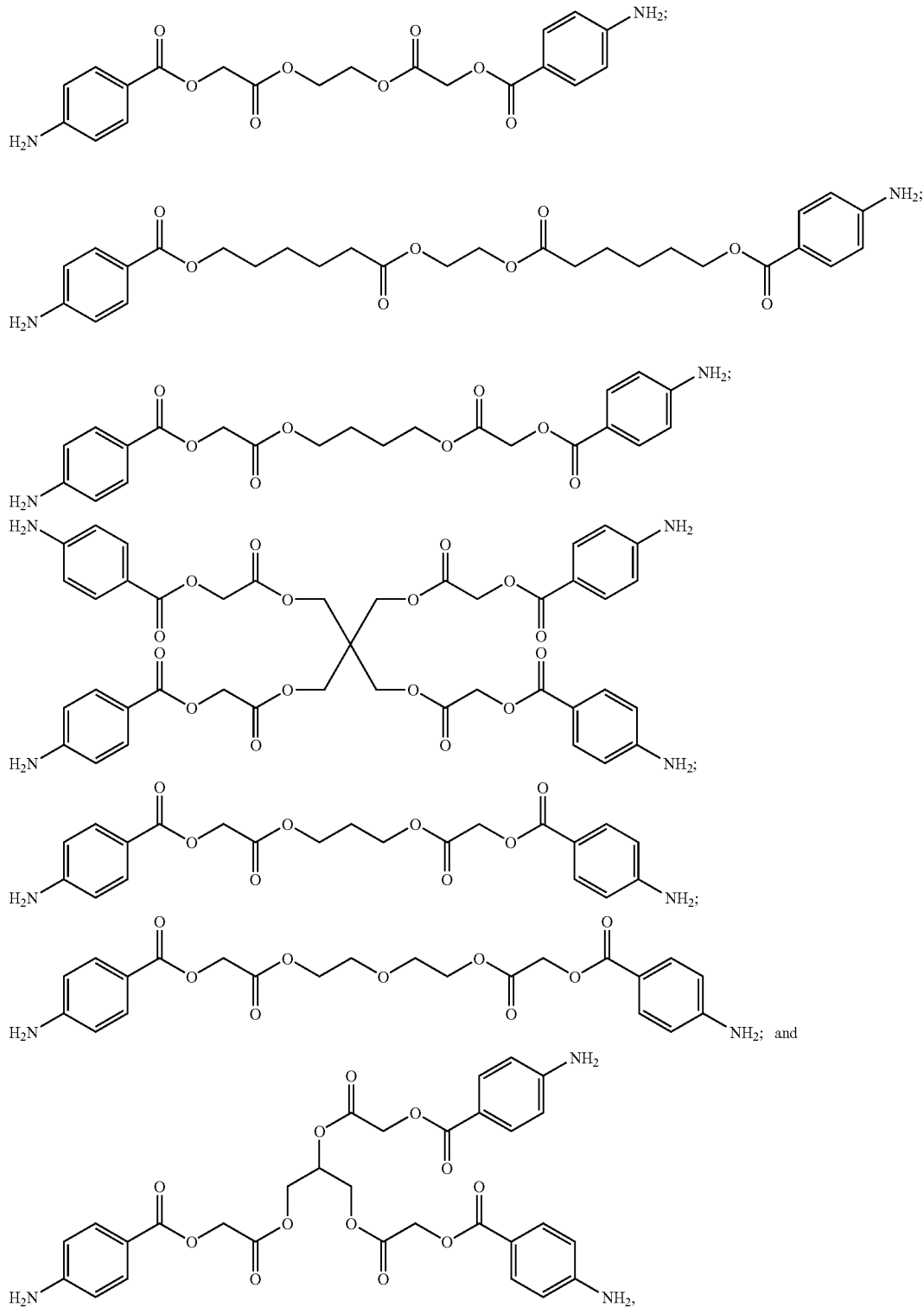

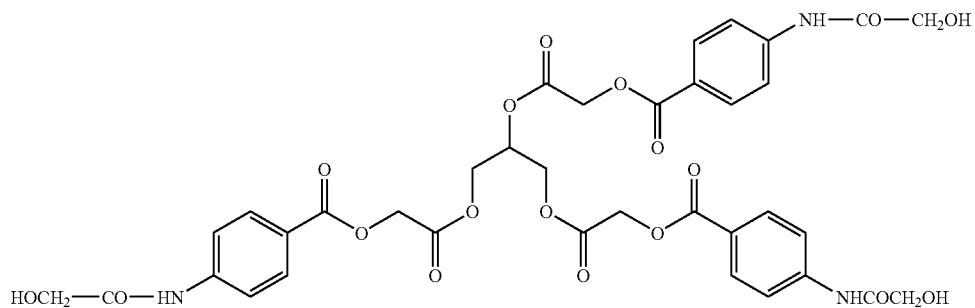
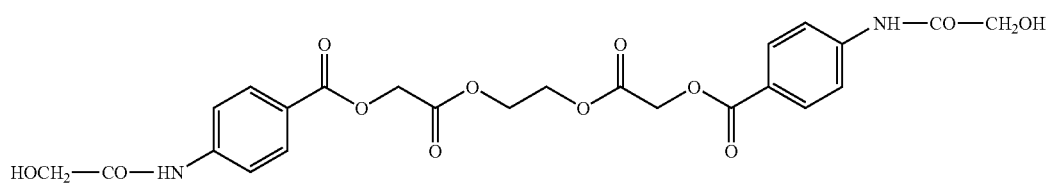
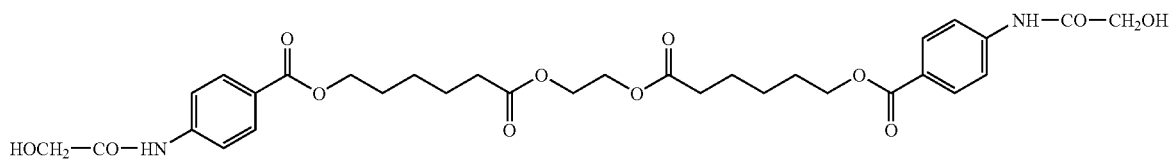
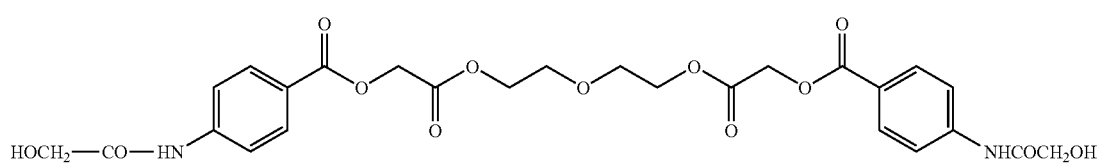
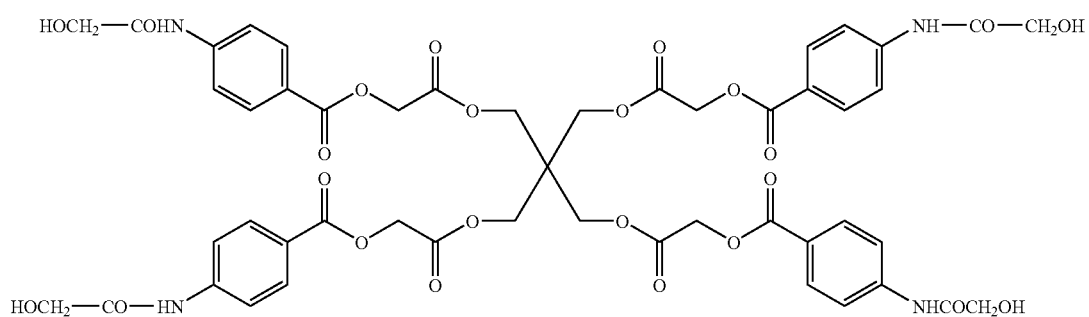
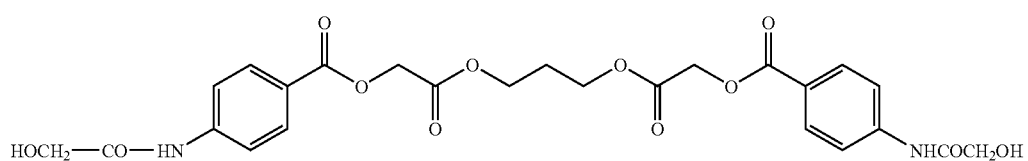
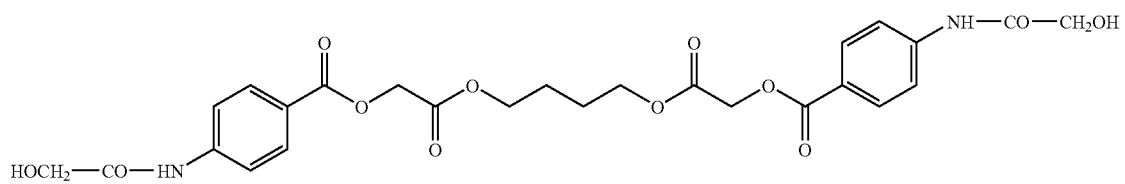

Hydrolysable Linker and Crosslinker Amide Alcohols of Formula XI of the Present Invention
A few examples of structures of hydrolysable linker and crosslinker amine acids of formula XII of the present invention are shown below.
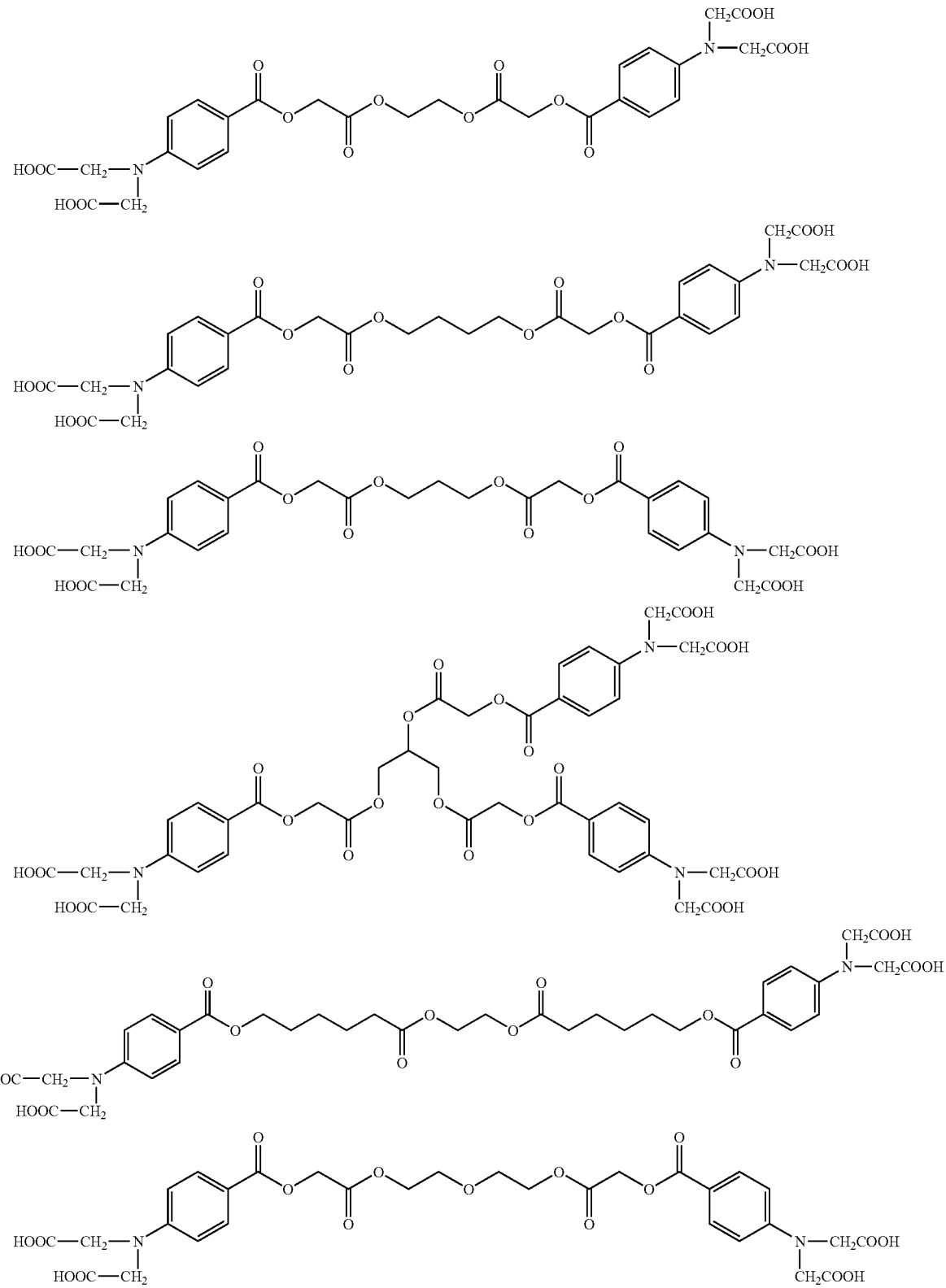

-continued

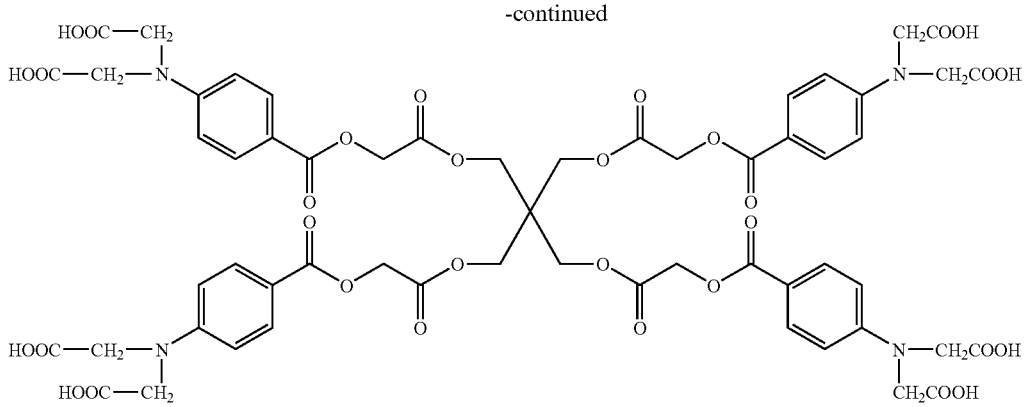

Hydrolysable Linker and Crosslinker Amine Acids of Formula XII of the Present Invention Derived from Symmetrical/Unsymmetrical Ether Diacids The present invention also provides novel linear and multiarmed hydrolysable monomeric and oligomeric linkers of formulas XIII-XVI as shown below derived from linear or branched diacid of formula C.

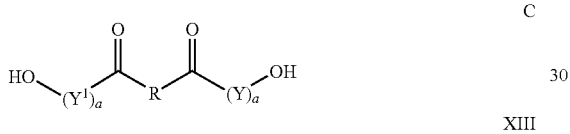

XIII

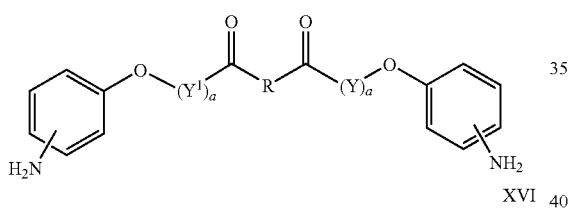

XVI

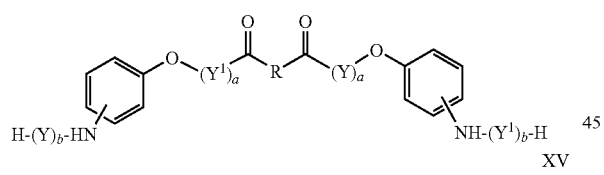

XV

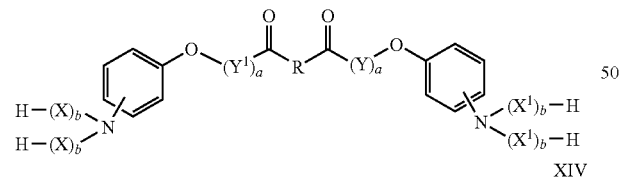

XIV

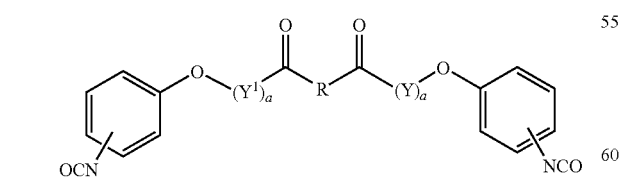

wherein:
R is a di-, tri, tetra-, penta- or hexaradical derived from $C_{1-25}$ alkyl, aryl, or aryl-$(C_{1-6}alkyl)_{1-3}$-, wherein from 1-4 of the $CH_2$ groups, preferably from 1-3 of the $CH_2$ groups, within the alkyl chain are optionally independently replaced by O or S atoms, preferably by O atoms, such that each of said O or S atoms is attached only to carbon atoms in the alkyl chain, with the proviso that the O or S atoms are separated from the di-, tri, tetra-, penta- or hexaradical chain ends by at least one carbon atom and that multiple O or S atoms in the di-, tri, tetra-, penta- or hexaradical chain must be separated from each other by at least two carbon atoms each a is independently an integer from about 0 to about 6;
each b is independently an integer from about 1 to about 6;
each X is independently:
—OC(═O)$CH_2$— (inverse glycolic acid moiety), —OC(═O)CH($CH_3$)— (inverse lactic acid moiety), —OC(═O)$CH_2OCH_2CH_2$— (inverse dioxanone acid moiety), —OC(═O)$CH_2CH_2CH_2CH_2CH_2$— (inverse caprolactone acid moiety), —OC(═O)$(CH_2)_y$—, or —OC(═O)$CH_2(OCH_2CH_2)_n$—; preferably —OC(═O)$CH_2$—, —OC(═O)CH($CH_3$)—, —OC(═O)$CH_2OCH_2CH_2$—, or —OC(═O)$CH_2CH_2CH_2CH_2CH_2$—; more preferably —OC(═O)$CH_2$— or —OC(═O)CH($CH_3$)—;
each $X^1$ is independently:
—$CH_2$C(═O)O— (glycolic acid moiety), —CH($CH_3$)C(═O)O— (lactic acid moiety), —$CH_2CH_2OCH_2$C(═O)O— (dioxanone acid moiety), —$CH_2CH_2CH_2CH_2CH_2$C(═O)O— (caprolactone acid moiety), —$(CH_2)_y$C(═O)O—, or —$(CH_2CH_2O)_nCH_2$C(═O)O—; preferably —$CH_2$C(═O)O—, —CH($CH_3$)C(═O)O—, —$CH_2CH_2OCH_2$C(═O)O—, or —$CH_2CH_2CH_2CH_2CH_2$C(═O)O—, more preferably —$CH_2$C(═O)O— or —CH($CH_3$)C(═O)O—;
each Y is independently:
—$OCH_2$C(═O)— (inverse glycolic ester moiety), —OCH($CH_3$)C(═O)— (inverse lactic ester moiety), —$OCH_2CH_2OCH_2$C(═O)— (inverse dioxanone ester moiety), —$OCH_2CH_2CH_2CH_2CH_2$C(═O)— (inverse caprolactone ester moiety), —O$(CH_2)_m$C(═O)—, or —O$(CH_2CH_2O)_nOCH_2$C(═O)—; preferably —$OCH_2$C(═O)—, —OCH($CH_3$)C(═O)—, —$OCH_2CH_2OCH_2$C(═O)—, or —$OCH_2CH_2CH_2CH_2CH_2$C(═O)—, more preferably —$OCH_2$C(═O)— or —OCH($CH_3$)C(═O)—;
each $Y^1$ is independently:
—C(═O)$CH_2$O— (glycolic ester moiety), —C(═O)CH($CH_3$)O— (lactic ester moiety), —C(═O)$CH_2OCH_2CH_2$O— (dioxanone ester moiety), —C(═O)$CH_2CH_2CH_2CH_2CH_2$O— (caprolactone ester moiety), —C(═O)$(CH_2)_m$O—, or —C(═O)

$CH_2$—O—$(CH_2CH_2O)_n$—; preferably —C(=O)$CH_2O$—, —C(=O)CH($CH_3$)O—, —C(=O)$CH_2OCH_2CH_2O$—, or —C(=O)$CH_2CH_2CH_2CH_2CH_2O$—; more preferably —C(=O)$CH_2O$— or —C(=O)CH($CH_3$)O—.

The linear or branched diacid of formula C of the present invention is derived from diacid of formula N, wherein R is as defined herein.

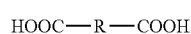

N

The linear and multiarmed hydrolysable monomeric and oligomeric linkers of the general formula XII, XIV, XV, and XVI of the present invention are derived from symmetrical or unsymmetrical diacid of formula C of the present invention as shown below in Scheme 3.

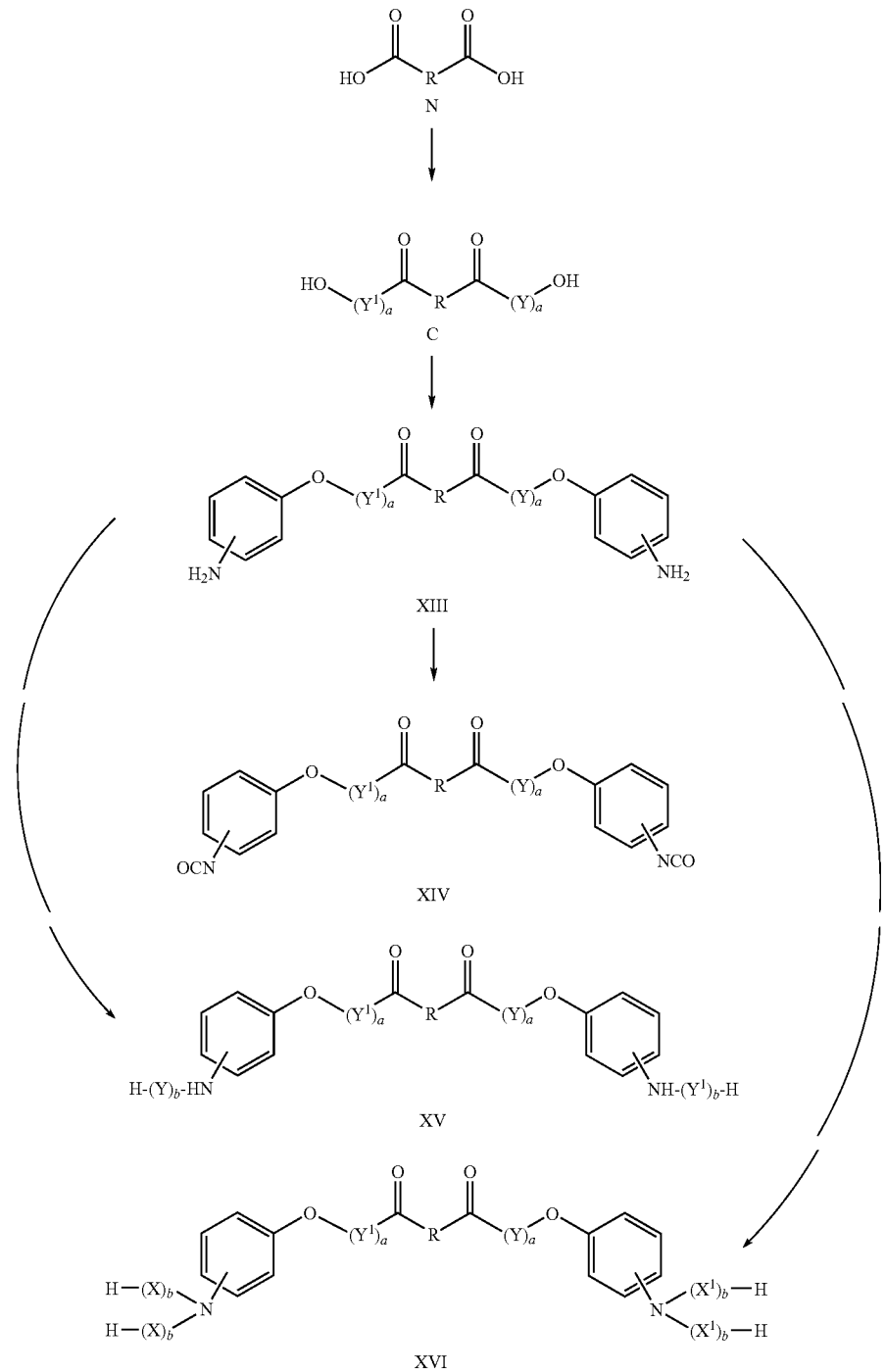

A few examples of structures of hydrolysable linker and crosslinkers representing structures XIII, XIV, XV, and XVI are shown below.

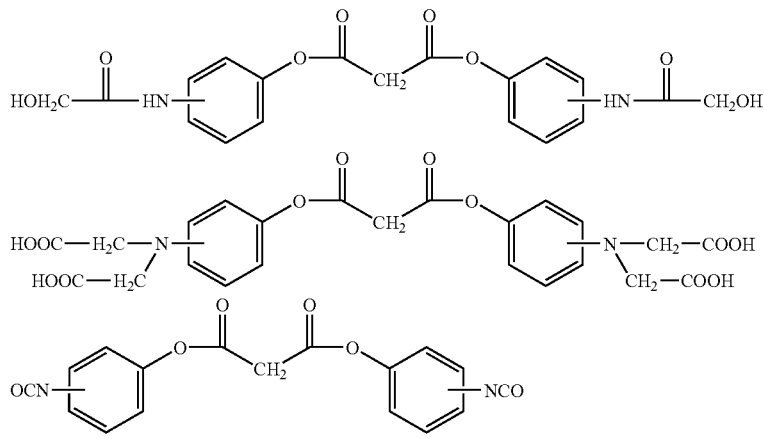

Hydrolysable Linker and Crosslinkers Representing Formula XIII, XIV, XV, and XVI In certain cases the biodegradable region may contain at least one amide functionality. The cross-linker of the present cross-linker may also include an ethylene glycol oligomer, oligo(ethylene glycol), poly(ethylene oxide), poly(vinylpyrrolidone), poly(propylene oxide), poly(ethyloxazoline), or combinations of these substances.

In yet another embodiment of the present invention, linear and multiarmed hydrolysable linker amines of the present invention have general structures as shown below derived from p-dioxanone and p-aminobenzoic acid:

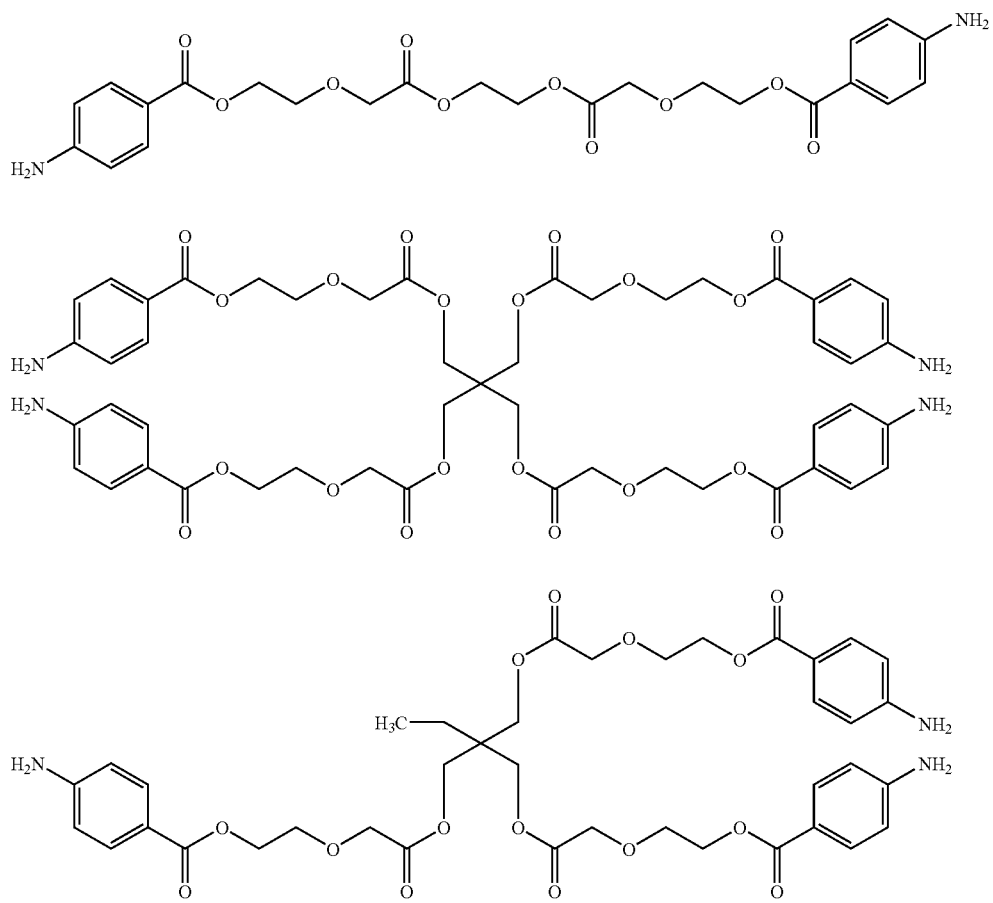

In another embodiment of the present invention, linear and multiarmed hydrolysable linker isocyanates of the present invention have general structures as shown below derived from p-dioxanone and p-aminobenzoic acid:

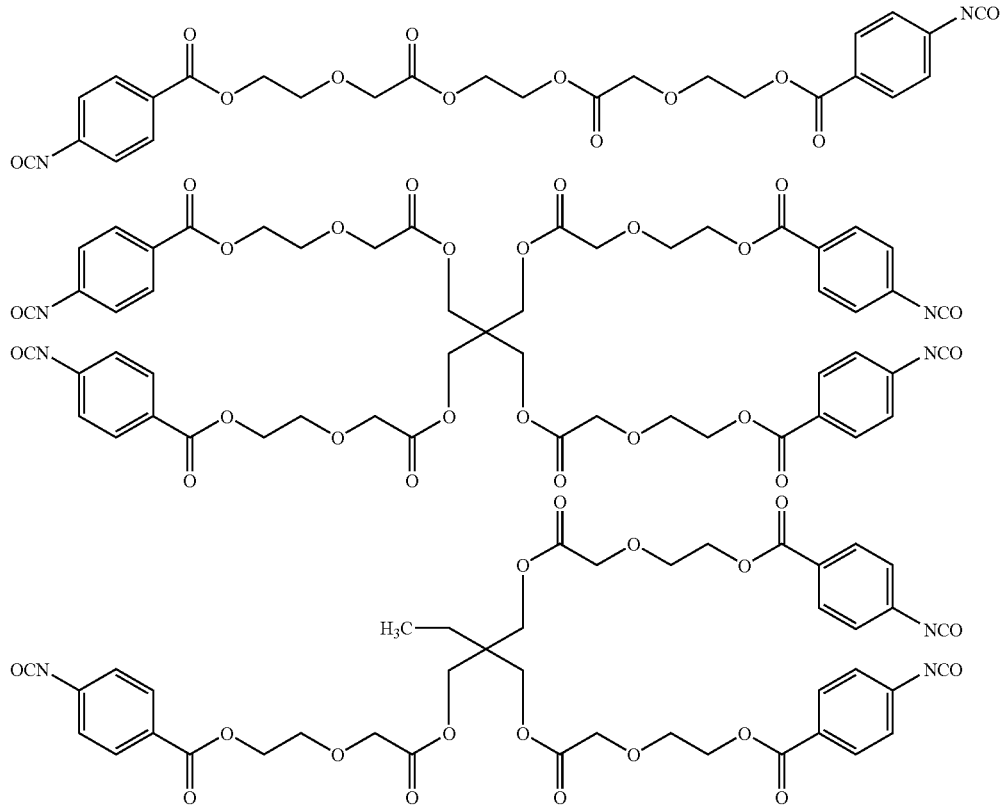

1-6). Glycolic acid based polymers should hydrolyze faster than dioxanone based, where as lactic acid and caprolactone based polymers should take much longer to hydrolyze than glycolic acid and dioxanone based polymers. The desired time range may be obtained by altering the number and type of functionalization species as well as the number of different functionalized phenolic compounds (e.g., a blend of two or more functionalized phenolics). The desired time range will also be impacted by moieties used for co-polymerization (e.g., difunctional compounds or lactone monomers).

The rate of hydrolysis of the materials of the present invention will depend upon a number of factors, including the functionalization used and the number of functionalizations present on the at least difunctionalized aromatic (e.g., from about 1 to about 6). For example, glycolic acid modified aromatics should generally hydrolyze more quickly than aromatics modified with dioxanone, whereas lactic acid and caprolactone modified aromatics should generally hydrolyze over a longer period of time as compared to glycolic acid and dioxanone modified aromatics. Furthermore, it is expected that the rate of hydrolysis will increase as the number of functional groups is increased. Thus, desired time ranges for hydrolysis may be obtained by altering the number and type of functionalization used to functionalize the aromatics.

The linkers of the present invention are typically easily incorporated in many different polymer-processing options such as polymer micro particles, nanoparticles and slab gels. Incorporation of hydrolysable links and cross-links into the backbone of polymer structure should permit control of overall degradation as well as the release rate of entrapped substances.

The present invention also contemplates the application of the hydrolysable carboxylic acids, amines, amide alcohols and isocyanates linkers and crosslinkers for preparing novel absorbable polymers with controlled degradation profile for biomedical applications.

The hydrolysable linkers and cross-linkers of the present invention can be polymerized via conventional polymerization process using diol, triols, dicarboxylic acids, tricarboxylic acids, diamines, or triamines based on the starting difunctionalized or trifunctionalized or tetrafunctionalized molecules, including those processes that synthesize polymers traditionally considered hydrolytically stable and non-biodegradable.

The present invention encompasses a variety of different polymers, some of which are copolymers. The polymers of the present invention include (a) polyesters (b) polyurethanes (c) polyamides (d) polyureas and degradable epoxy amine resin. The absorption profile of the polymers of the present invention will depend upon a number of factors, including the functionalization species used and the number of functionalization species present on the functionalized phenolic (e.g., The polymers of the present invention can be used in various medical applications described herein or can be further polymerized with lactone monomers, such as glycolide, lactide, ε-caprolactone, trimethylene carbonate, and p-dioxanone, and the resulting absorbable functionalized phenolic/lactone copolymers can be used in the various medical applications described herein.

The polymers of the present invention with at least two reactive sites can be polymerized with difunctional molecules (e.g., dicarboxylic acids, dialcohols, diisocyanates, amino-alcohols, hydroxy-carboxylic acids, and diamines) to form absorbable polymers, including but not limited to polyesters, polyester amides, polyurethanes, polyamides, polyureas, epoxy amine resins and polyanhydrides by simple polycondensation reactions. These polymers can be used in various medical applications or can be further polymerized with lactone monomers, such as glycolide, lactide, ε-caprolactone, trimethylene carbonate, and p-dioxanone, and the resulting absorbable polymers potential have the medical applications described above.

In another example of the present invention, functionalized dihalogen linkers of the present invention can be used in the preparation of polyesters by reacting with dicarboxylic acid compounds. Dicarboxylic acid compounds useful in the present invention have the following structure:

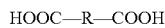

HOOC—R—COOH wherein:
R is a diradical derived from a saturated or unsaturated, substituted or unsubstituted alkyl having from about 1 to about 18 carbon atoms, substituted or unsubstituted aryl having from about 6 to about 18 carbon atoms, or substituted or unsubstituted alkylaryl group having from about 7 to about 18 carbon atoms, wherein one or more, preferably from one to about three $CH_2$ groups within the alkyl chain are optionally independently replaced by O or S atoms, preferably O atoms, such that each of said O or S atoms is attached only to carbon atoms in the alkyl chain, with the proviso that the O or S atoms are separated from the diradical chain ends by at least one carbon atom and that multiple O or S atoms in the diradical chain must be separated from each other by at least two carbon atoms.

In another example of the present invention, functionalized dicarboxylic acid linker compounds of the present invention can be used in the preparation of polyesters by reacting with dialcohol (i.e., diol) compounds. Dialcohol compounds useful in the present invention have the following structure:

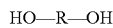

HO—R—OH wherein:
R is a diradical derived from a saturated or unsaturated, substituted or unsubstituted alkyl having from about 1 to about 18 carbon atoms, substituted or unsubstituted aryl having from about 6 to about 18 carbon atoms, or substituted or unsubstituted alkylaryl group having from about 7 to about 18 carbon atoms, wherein one or more, preferably from one to about three $CH_2$ groups within the alkyl chain are optionally independently replaced by O or S atoms, such that each of said O or S atoms is attached only to carbon atoms in the alkyl chain, with the proviso that the O or S atoms are separated from the diradical chain ends by at least one carbon atom and that multiple O or S atoms in the diradical chain must be separated from each other by at least two carbon atoms.

Alternatively, polyalkylene oxides have weight average molecular weights from about 500-5,000 can be used as a diol (i.e., a polydiol). Suitable diols or polydiols for use in the present invention are diol or diol repeating units with up to 8 carbon atoms.

Examples of suitable diols include 1,2-ethanediol (ethylene glycol); 1,2-propanediol (propylene glycol); 1,3-propanediol; 1,4-butanediol; 1,5-pentanediol; 1,3-cyclopentanediol; 1,6-hexanediol; 1,4-cyclohexanediol; 1,8-octanediol; and, combinations thereof. Examples of polydiols include polyethylene glycol and polypropylene glycol with weight average molecular weights of 500-5000.

In another example of the present invention, functionalized dihydroxy linker amide diol compounds of the present invention can be used in the preparation of polyurethanes by reacting with diisocyanate compounds. Examples of diisocyanates include hexamethylene diisocyanate, lysine diisocyanate, methylene diphenyl diisocyanate (e.g., MDI), hydrogenated MDI (e.g., methylene dicyclohexyl diisocyanate), and isophorone diisocyanate, as well as any of the isocyanates of the present invention.

In another example of the present invention, functionalized dicarboxylic acid linker compounds of the present invention can be used in the preparation of polyesteramides by reacting with amino-alcohol compounds. Amino-alcohols compounds useful in the present invention have the following structure:

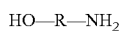

HO—R—$NH_2$ wherein:
R is a diradical derived from a saturated or unsaturated, substituted or unsubstituted alkyl having from about 1 to about 18 carbon atoms, substituted or unsubstituted aryl having from about 6 to about 18 carbon atoms, or substituted or unsubstituted alkylaryl group having from about 7 to about 18 carbon atoms, wherein one or more, preferably from one to about three $CH_2$ groups within the alkyl chain are optionally independently replaced by O or S atoms, such that each of said O or S atoms is attached only to carbon atoms in the alkyl chain, with the proviso that the O or S atoms are separated from the diradical chain ends by at least one carbon atom and that multiple O or S atoms in the diradical chain must be separated from each other by at least two carbon atoms.

In another example of the present invention, functionalized dicarboxylic acid linker compounds of the present invention can be used in the preparation of polyamides by reacting with diamine compounds. Diamine compounds useful in the present invention have the following structure:

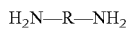

$H_2N$—R—$NH_2$ wherein:
R is a diradical derived from a saturated or unsaturated, substituted or unsubstituted alkyl having from about 1 to about 18 carbon atoms, substituted or unsubstituted aryl having from about 6 to about 18 carbon atoms, or substituted or unsubstituted alkylaryl group having from about 7 to about 18 carbon atoms, wherein one or more, preferably from about one to about four, more preferably from one to about three $CH_2$ groups within the alkyl chain are optionally independently replaced by O or S atoms, such that each of said O or S atoms is attached only to carbon atoms in the alkyl chain, with the proviso that the O or S atoms are separated from the diradical chain ends by at least one carbon atom and that multiple O or S atoms in the diradical chain must be separated from each other by at least two carbon atoms.

Linker and crosslinker amines of the present invention can also be reacted with epoxides to form degradable epoxyamine resins. The examples of the epoxides that can be used in the present invention include but not limited to diglycidyl ether, polyethyethyleneglucol polyglycidyl ether and epoxides prepared from naturally occurring fatty acids, glycidyl methacrylate and glycidyl acrylate.

In another example of the present invention, functionalized dicarboxylic acid compounds of the present invention can be used in the preparation of polyanhydrides by reacting with the dicarboxylic acid compounds described above.

The functionalized linker compounds of the present invention having more than two reactive groups (e.g., 3) are expected to be useful in the preparation of cross linked hydrogels and are prepared Examples of polymers of the present invention have weight-average molecular weights above about 20,000 daltons or above about 100,000 daltons, calculated from gel permeation chromatography (GPC) relative to polystyrene standards in tetrahydrofuran (THF) without further correction.

The polymers of the present invention should be able to be processed by known methods commonly employed in the field of synthetic polymers to provide a variety of useful articles with valuable physical and chemical properties. The useful articles can be shaped by conventional polymer-forming techniques such as extrusion, compression molding, injection molding, solvent casting, and wet spinning. Shaped articles prepared from the polymers are expected to be useful as degradable devices for medical implant applications.

The present invention also relates to a composition, comprising: at least two (e.g., 2, 3, 4, or 5) functional phenolic compounds of the present invention.

The present invention also relates to a composition, comprising: at least two functionalized linker compounds, wherein the composition is suitable for use as at least one of the following: (a) a solvent for drugs; (b) a nutritional compound; (c) a cosmetic: and, (d) a pharmaceutical. Each of the compositions may further comprise an additional component suitable for such composition. For example, when the composition is suitable for use as a cosmetic it may further comprise: one or more cosmetic ingredients. Also, when the composition is suitable for use as a pharmaceutical it may further comprise: one or more pharmaceutically acceptable excipients. In addition, each of the compositions may comprise a functionalized phenolic derived from a phenolic having a property useful to that type of composition. For example, the starting phenolic may be (a) a nutritional supplement or a food intermediary; (b) an anticancer agent; (c) an antimicrobial agent; (d) an anti-inflammatory agent; (e) a pain-reducer; and, (f) an antioxidant agent. Also, the compositions may further comprise one of agents (a)-(f).

The compositions of the present invention may be suitable for administration via a route selected from oral, enteral, parenteral, topical, transdermal, ocular, vitreal, rectal, nasal, pulmonary, and vaginal.

The implantable medical devices of the present invention, comprise: at least one absorbable polymer of the present invention. For example, a polymer of the present invention can be combined with a quantity of a biologically or pharmaceutically active compound sufficient to be therapeutically effective as a site-specific or systemic drug delivery system (see Gutowska et al., J. Biomater. Res., 29, 811-21 (1995) and Hoffman, J. Controlled Release, 6, 297-305 (1987)). Another example of the present invention is a method for site-specific or systemic drug delivery by implanting in the body of a patient in need thereof an implantable drug delivery device comprising a therapeutically effective amount of a biologically or a physiologically active compound in combination with at least one absorbable polymer of the present invention.

In another example, at least one polymer of the present invention is formed into a porous device (see Mikos et al., Biomaterials, 14, 323-329 (1993) or Schugens et al., J. Biomed. Mater. Res., 30, 449-462 (1996)) to allow for the attachment and growth of cells (see Bulletin of the Material Research Society, Special Issue on Tissue Engineering (Guest Editor: Joachim Kohn), 21(11), 22-26 (1996)). Thus, the present invention provides a tissue scaffold comprising a porous structure for the attachment and proliferation of cells either in vitro or in vivo formed from at least one absorbable polymer of the present invention The present invention also relates to an article (e.g., an implantable medical device), comprising: a metal or polymeric substrate having thereon a coating, wherein the coating, comprises: at least one polymer of the present invention.

The present invention also relates to a molded article prepared from at least one polymer of the present invention.

The present invention also relates to a controlled drug delivery system, comprising: at least one polymer of the present invention physically admixed with a biologically or pharmacologically active agent. For example, the controlled drug delivery system may comprise: a biologically or pharmacologically active agent coated with at least one polymer of the present invention.

The present invention also relates to a controlled drug delivery system, comprising: a biologically or pharmacologically active agent physically embedded or dispersed into a polymeric matrix formed from at least one polymer of the present invention.

The present invention also relates to a tissue scaffold having a porous structure for the attachment and proliferation of cells, either in vitro or in vivo, formed from one least one polymer of the present invention.

The present invention also relates to a composition, comprising: at least one polymer of the present invention, which has been further polymerized with at least one lactone monomer selected from: glycolide, lactide, p-dioxanone, trimethylene carbonate, and caprolactone.

The present invention also relates to an implantable biomedical device, comprising: at least one polymer that has been further polymerized with at least one lactone monomer.

The present invention also relates to a biodegradable chewing gum composition, comprising: an effective amount of at least one polymer that has been further polymerized with at least on lactone monomer.

The present invention also relates to an article (e.g., an implantable medical device), comprising: a metal or polymeric substrate and having thereon a coating, wherein said coating comprises at least one polymer that has been further polymerized with at least one lactone monomer.

The present invention also relates to a molded article prepared from at least one polymer that has been further polymerized with at least one lactone monomer.

The present invention also relates to a monofilament or multifilament prepared from at least one polymer that has been further polymerized with at least one lactone monomer.

The present invention also relates to a controlled drug delivery system, comprising: at least one polymer that has been further polymerized with at least one lactone monomer, which has been physically admixed with a biologically or pharmacologically active agent.

The present invention also relates to a controlled drug delivery system, comprising: a biologically or pharmacologically active agent physically embedded or dispersed into a polymeric matrix formed from at least one polymer that has been further polymerized with at least one lactone monomer.

The present invention also relates to a tissue scaffold having a porous structure for the attachment and proliferation of cells, either in vitro or in vivo, formed from at least one polymer that has been further polymerized with at least one lactone monomer.

The present invention also relates to low molecular weight polymers or oligomers of the functionalized phenolic compounds of the present invention that are further reacted to form reactive end groups (e.g., isocyanates, expoxides, and acrylates). Low-molecular weight polymers or oligomers as used herein means a polymer having a number average molecular weight of about 500-20,000 or 500-10,000. For example, some of the functionalized phenolic compounds behave chemically like diols. They can be reacted with dicarboxylic acids to form polyesters, which are usually hydroxyterminated. These hydroxyterminated oligomers can be further reacted to form isocyanates, epoxides and acrylates. Similarly the functionalized phenolic compounds can be reacted with isocyanates to make urethanes. Thus, the present invention also includes a composition, comprising: at least one polymer of the present invention, which has been further reacted to form reactive end groups.

The present invention also relates to polymers made from functionalized linker and cross-linker compounds that have been sterilized by cobalt-60 radiation, electron beam radiation, and/or ethylene oxide.

"Bioabsorbable" or "absorbable" as used herein means that the material readily reacts or enzymatically degrades upon exposure to bodily tissue for a relatively short period of time, thereby experiencing a significant weight loss in that short period of time. Complete bioabsorption/absorption should take place within twelve months, although it may be complete within nine months or within six months. In this manner, the polymers of the present invention can be fabricated into medical and surgical devices, which are useful for a vast array of applications requiring complete absorption within a relatively short time period.

The biological properties of the bioabsorbable polymers of the present invention used to form a device or part thereof, as measured by its absorption rate and its breaking strength retention in vivo (BSR), can be varied to suit the needs of the particular application for which the fabricated medical device or component is intended. This can be conveniently accomplished by varying the ratio of components of the polymer chosen.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, p 1445, the disclosure of which is hereby incorporated by reference.

"Therapeutically effective amount" includes an amount of a compound of the present invention that is effective when administered alone or in combination to treat the desired indication.

"Alkyl" includes both branched and straight-chain saturated aliphatic hydrocarbon groups having the specified number of carbon atoms. $C_{1-6}$ alkyl, for example, includes $C_1$, $C_2$, $C_3$, $C_4$, $C_5$, and $C_6$ alkyl groups. Examples of alkyl include methyl, ethyl, n-propyl, i-propyl, n-butyl, s-butyl, t-butyl, n-pentyl, s-pentyl, and n-hexyl.

"Aryl" refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl.

Polymers of the present invention may be made in the form of random copolymers or block copolymers. A coupling agent may also be added to the polymers of the present invention. A coupling agent is a reagent that has a least two functional groups that are capable of covalently bonding to two different monomers. Examples of coupling agents include trifunctional or tetrafunctional polyols, oxycarboxylic acids, and polybasic carboxylic acids (or acid anhydrides thereof). Other coupling agents include the difunctional groups (e.g., diols, diacids, diamines, and hydroxy-acids) previously discussed. The addition of the coupling agents causes the branching of long chains, which can impart desirable properties in the molten state to the pre-polymer. Examples of polyfunctional coupling agents include trimethylol propane, glycerin, pentaerythritol, malic acid, citric acid, tartaric acid, trimesic acid, propane tricarboxylic acid, cyclopentane tetracarboxylic anhydride, and combinations thereof.

A "pre-polymer" is a low-molecular weight polymer, as previously defined, that have reactive endgroups (e.g., hydroxy groups) that can be further reactive with, for example, the lactone monomers.

The amount of coupling agent to be added before gelation occurs is a function of the type of coupling agent used and the polymerization conditions of the polymer or molecular weight of the pre-polymer to which it is added. Generally in the range of from about 0.1 to about 10 mole percent of a trifunctional or a tetrafunctional coupling agent may be added based on the moles of polymers present or anticipated from the synthesis.

The polymerization of a polyester of the present invention can be performed under melt polycondensation conditions in the presence of an organometallic catalyst at elevated temperatures. The organometallic catalyst can be a tin-based catalyst (e.g., stannous octanoate or dibutyl tin oxide). The catalyst can be present in the mixture at a mole ratio of diol, dicarboxylic acid, and optionally lactone monomer to catalyst will be in the range of from about 15,000/1 to 80,000/1. The reaction can be performed at a temperature not less than about 120° C. under reduced pressure. Higher polymerization temperatures may lead to further increases in the molecular weight of the copolymer, which may be desirable for numerous applications. The exact reaction conditions chosen will depend on numerous factors, including the properties of the polymer desired, the viscosity of the reaction mixture, and the glass transition temperature and softening temperature of the polymer. Desired reaction conditions of temperature, time and pressure can be readily determined by assessing these and other factors. Generally, the reaction mixture will be maintained at about 220° C. The polymerization reaction can be allowed to proceed at this temperature until the desired molecular weight and percent conversion is achieved for the copolymer, which will typically take about 15 minutes to 24 hours. Increasing the reaction temperature generally decreases the reaction time needed to achieve a particular molecular weight.

Polymerization conditions for the preparation of polyesters from dihalogen compounds with dicarboxylic acids are described in the literature. Polymerization conditions for the preparation of other types of polymers of the present invention (e.g., polyamides and polyurethanes) are described in the literature. Those skilled in the art will recognize that the polymers described herein can be made from known procedures.

Copolymers of the absorbable polymers of the present invention can be prepared by preparing a pre-polymer under melt polycondensation conditions, then adding at least one lactone monomer or lactone pre-polymer. The mixture could then be subjected to the desired conditions of temperature and time to copolymerize the pre-polymer with the lactone monomers.

A lactone pre-polymer is a pre-polymer formed by ring opening polymerization with a known initiator (e.g., ethylene glycol, diethylene glycol, glycerol, or other diols or triols).

The molecular weight of the pre-polymer as well as its composition can be varied depending on the desired characteristic, which the pre-polymer is to impart to the copolymer. For example, the pre-polymers of the present invention, from which the copolymer is prepared, generally have a molecular weight that provides an inherent viscosity between about 0.2 to about 2.0 deciliters per gram (dl/g) as measured in a 0.1 g/dl solution of hexafluoroisopropanol at 25° C. Those skilled in the art will recognize that the pre-polymers described herein can also be made from mixtures of more than one diol or dicarboxylic acid.

One of the beneficial properties of the polyesters of the present invention is that the ester linkages are hydrolytically unstable, and therefore the polymer is bioabsorbable because it readily breaks down into small segments when exposed to moist bodily tissue. In this regard, while it is envisioned that co-reactants could be incorporated into the reaction mixture of the dicarboxylic acid and the diol for the formation of the polyester pre-polymer, it is preferable that the reaction mixture does not contain a concentration of any co-reactant which would render the subsequently prepared polymer nonabsorbable. The reaction mixture can be substantially free of any such co-reactants if the presence thereof results in a nonabsorbable polymer.

The polymers of the present invention can be melt processed by numerous methods to prepare a vast array of useful devices. These polymers can be injection or compression molded to make implantable medical and surgical devices, especially wound closure devices.

Alternatively, the polymers can be extruded to prepare fibers. The filaments thus produced may be fabricated into sutures or ligatures, attached to surgical needles, packaged, and sterilized by known techniques. The polymers of the present invention may be spun as multifilament yarn and woven or knitted to form sponges or gauze, (or non-woven sheets may be prepared) or used in conjunction with other molded compressive structures as prosthetic devices within the body of a human or animal where it is desirable that the structure have high tensile strength and desirable levels of compliance and/or ductility. Examples include tubes, including branched tubes, for artery, vein, or intestinal repair, nerve splicing, tendon splicing, sheets for typing up and supporting damaged surface abrasions, particularly major abrasions, or areas where the skin and underlying tissues are damaged or surgically removed.

Additionally, the polymers can be molded to form films which, when sterilized, are useful as adhesion prevention barriers. Another alternative processing technique for the polymers of the present invention includes solvent casting, particularly for those applications where a drug delivery matrix is desired.

The polymers of the present invention can be used to coat a surface of a surgical article to enhance the lubricity of the coated surface. The polymer may be applied as a coating using conventional techniques. For example, the polymer may be solubilized in a dilute solution of a volatile organic solvent (e.g. acetone, methanol, ethyl acetate, or toluene), and then the article can be immersed in the solution to coat its surface. Once the surface is coated, the surgical article can be removed from the solution where it can be dried at an elevated temperature until the solvent and any residual reactants are removed.

For coating applications, the polymer should exhibit an inherent viscosity, as measured in a 0.1 gram per deciliter (g/dl) of hexafluoroisopropanol (HFIP), between about 0.05-2.0 dl/g or about 0.10-0.80 dl/g. If the inherent viscosity were less than about 0.05 dl/g, then the polymer may not have the integrity necessary for the preparation of films or coatings for the surfaces of various surgical and medical articles. On the other hand, it is possible to use polymers with an inherent viscosity greater than about 2.0 dl/g, though it may be difficult to do so.

Although numerous surgical articles (including but not limited to endoscopic instruments) can be coated with the polymer of the present invention to improve the surface properties of the article, specific surgical articles include surgical sutures, stents, and needles. For example the surgical article can be a suture, which can be attached to a needle. The suture can be a synthetic absorbable suture. These sutures are derived, for example, from homopolymers and copolymers of lactone monomers such as glycolide, lactide, ε-caprolactone, 1,4-dioxanone, and trimethylene carbonate. The suture can be a braided multifilament suture composed of polyglycolide or poly(glycolide-co-lactide).

The amount of coating polymer to be applied on the surface of a braided suture can be readily determined empirically, and will depend on the particular copolymer and suture chosen. Ideally, the amount of coating copolymer applied to the surface of the suture may range from about 0.5-30 percent of the weight of the coated suture or from about 1.0-20 weight percent, or from 1-5 percent by weight. If the amount of coating on the suture were greater than about 30 weight percent, then it may increase the risk that the coating may flake off when the suture is passed through tissue Sutures coated with the polymers of the present invention are desirable because they have a more slippery feel, thus making it easier for the surgeon to slide a knot down the suture to the site of surgical trauma. In addition, the suture is more pliable, and therefore is easier for the surgeon to manipulate during use. These advantages are exhibited in comparison to sutures which do not have their surfaces coated with the polymer of the present invention.

When the article of the present invention is a metal stent, the amount of coating applied to the surface of the article is an amount which creates a layer with a thickness ranging, for example, between about 2-20 microns on the stent or about 4-8 microns. If the amount of coating on the stent were such that the thickness of the coating layer was greater than about 20 microns, or if the thickness was less than about 2 microns, then the desired performance of the stent as it is passed through tissue may not be achieved.

When the article of the present invention is a surgical needle, the amount of coating applied to the surface of the article is an amount which creates a layer with a thickness ranging, for example, between about 2-20 microns on the needle or about 4-8 microns. If the amount of coating on the needle were such that the thickness of the coating layer was greater than about 20 microns, or if the thickness was less than about 2 microns, then the desired performance of the needle as it is passed through tissue may not be achieved.

The polymers of the present invention can also be used as a pharmaceutical carrier in a drug delivery matrix. To form this matrix the polymer can be mixed with a therapeutic agent to form the matrix. There are a variety of different therapeutic agents, which can be used in conjunction with the polymers of the invention. In general, therapeutic agents which may be administered via the pharmaceutical compositions of the invention include, antiinfectives such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

The drug delivery matrix may be administered in any suitable dosage form including orally, parenterally, subcutaneously as an implant, vaginally, or as a suppository. Matrix formulations containing the polymers of the present invention may be formulated by mixing one or more therapeutic agents with the polymer. The therapeutic agent, may be present as a liquid, a finely divided solid, or any other appropriate physical form. Typically, but optionally, the matrix will include one or more additives, e.g., nontoxic auxiliary substances such as diluents, carriers, excipients, or stabilizers. Other suitable additives may be formulated with the polymers of the present invention and pharmaceutically active agent. If water is to be used, then it can be useful to add it just before administration.

The amount of therapeutic agent will be dependent upon the particular drug employed and medical condition being treated. Typically, the amount of drug represents about 0.001%-70%, 0.001%-50%, or 0.001%-20% by weight of the matrix.

The quantity and type of polymer incorporated into a composition (e.g., parenterally delivered composition) will vary depending on the release profile desired and the amount of drug employed. The product may contain blends of polymers of the present invention to provide the desired release profile or consistency to a given formulation.

The polymers of the present invention, upon contact with body fluids including blood or the like, undergoes gradual degradation (mainly through hydrolysis) with concomitant release of the dispersed drug for a sustained or extended period (as compared to the release from an isotonic saline solution). This can result in prolonged delivery (e.g., over 1-2,000 hours or 2-800 hours) of effective amounts (e.g., 0.0001 mg/kg/hour to 10 mg/kg/hour) of the drug. This dosage form can be administered as is necessary depending on the subject being treated, the severity of the affliction, and the judgment of the prescribing physician.

Individual formulations of drugs and polymers of the present invention may be tested in appropriate in vitro and in vivo models to achieve the desired drug release profiles. For example, a drug could be formulated with a polymer of the present invention and orally administered to an animal. The drug release profile could then be monitored by appropriate means such as, by taking blood samples at specific times and assaying the samples for drug concentration. Following this or similar procedures, those skilled in the art will be able to formulate a variety of formulations.

EXAMPLES

The present invention will now be illustrated by reference to the following specific, non-limiting examples. Those skilled in the art of organic synthesis may be aware of still other synthetic routes to the invention compounds. The reagents and intermediates used herein are commercially available or may be prepared according to standard literature procedures.

Example 1

Synthesis of Chloro-Acetic Acid 2-(2-Chloro-Acetoxy)-Ethyl Ester

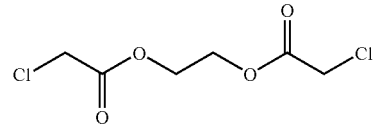

A solution of ethylene glycol (100 grams, 1.611 moles), chloro acetic acid (385 grams, 4.031 moles) and para-toluenesulphonic acid (1 gram) in toluene (750 ml) in a 2 lit 4 neck round bottom flask equipped with a mechanical stirrer and dean-stark apparatus was refluxed for 8 hours, cooled to room temperature. The toluene layer was washed with water (2×300 ml), 5% sodium bicarbonate solution (3×500 ml), water (2×300 ml), dried over sodium sulphate and distilled to get crude 1, which was purified by high vacuum distillation to get pure 1 (242 grams, 69.8%), which slowly crystallized to white crystals with a melting point of 44° C. The pure product 1 was also characterized using $^1$H NMR spectroscopy in CDCl$_3$: δ 4.16 (s, 2H, CH$_2$), 4.85 (s, 2H, CH$_2$).

Example 2

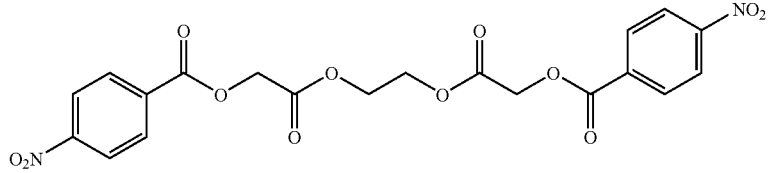

To a solution of 4-nitrobenzoic acid (155 grams, 927 mmoles), triethyl amine (101.6 grams, 1.004 moles) in dimethylformamide (250 ml) was added 1 (60 grams, 279 mmoles) in small portions and stirred at 50° C. for 6 hours. The solids were filtered off, the dimethylformamide solution was added onto 5% sodium bicarbonate solution (1 lit), filtered crude 2, recrystallised in chloroform:methanol (1:1) to get pure 2 (87 grams, 65.5%) as a off-white powder with a melting point of 116.5-118° C. The pure product 2 was also characterized using $^1$H NMR spectroscopy in CDCl$_3$: δ 4.46 (s, 2H, CH$_2$), 4.88 (s, 2H, CH$_2$), 8.30 (dd, 4H, Ar).

Example 3

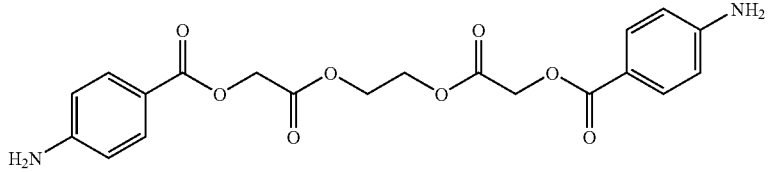

The compound from Example 2 (76 grams, 159.66 mmoles) was dissolved in dimethylformamide (150 ml) in a pressure vessel, Raney-Nickel (30 grams) added and the mixture stirred under an atmosphere of hydrogen (4 Kg) for 24 hours. The catalyst was removed by filtration, and 3 was precipitated by adding methanol, filtered, dried to get pure 3 (54 grams, 81.3%) as a off-white powder with a melting point of 183-185° C. The pure product 3 was also characterized using $^1$H NMR spectroscopy in DMSO-d$_6$: δ4.32 (s, 2H, CH$_2$), 4.78 (s, 2H, CH$_2$), 6.10 (s, 2H, NH$_2$), 6.60 (d, 2H, Ar), 7.78 (d, 2H, Ar).

Hydrolysis
Example-3—0.5 grams
Aldrich pH9 buffer—50 ml
Temperature—100° C.
Hydrolyzed in 5 hours Example 4

Chloro-Acetic Acid 2-(2-Chloro-Acetoxy)-Ethyl Ester

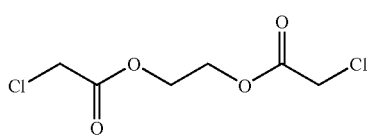

A solution ethylene glycol (100 grams, 1.611 moles), chloroacetic acid (385 grams, 4.031 moles) and para-toluenesulphonic acid (1 gram) in toluene (750 ml) in a 2 lit, 4 neck round bottom flask equipped with a mechanical stirrer and a dean-stark apparatus was refluxed for 8 hours and cooled to room temperature. The toluene layer was washed with water (2×300 ml), 5% sodium bicarbonate solution (3×500 ml), water (2×300 ml), dried over sodium sulphate and distilled to get crude 4, which was purified by high vacuum distillation to get pure 4 (242 grams, 69.8%), which slowly crystallized to white crystals. m.p: 44° C. The pure product 4 was also characterized using $^1$HNMR spectroscopy in CDCl$_3$: δ 4.16 (s, 2H, CH$_2$).

Example 5

(4-Nitro-phenoxy)-acetic acid-2-[2-(4-nitro-phenoxy)-acetoxy]-ethyl ester

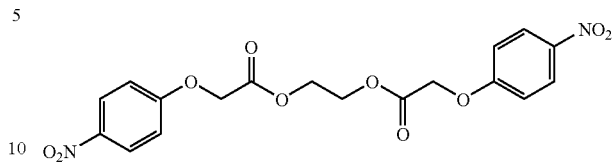

To a mixture of 4-nitrophenol (50 grams, 359.42 mmoles), potassium carbonate (248 grams, 1.794 moles), sodium iodide (5 grams) in acetone (250 ml) was added 4 (25 grams, 116.25 mmoles) in small portions and stirred at reflux for 24 hours. Acetone was distilled and water (1000 ml) was added. Crude 5 was filtered, dried and purified by column chromatography on silica gel using hexane:ethyl acetate (95:5) to get pure 5 (30 grams, 61.4%) as a white powder. m.p: 138-139° C. The pure product 5 was also characterized using $^1$H NMR spectroscopy in CDCl$_3$: δ 4.49 (s, 2H, CH$_2$), 4.74 (s, 2H, CH$_2$), 6.98 (d, 2H, Ar), 8.24 (d, 2H, Ar).

Example 6

(4-Amino-phenoxy)-acetic acid-2-[2-(4-amino-phenoxy)-acetoxy]-ethyl ester

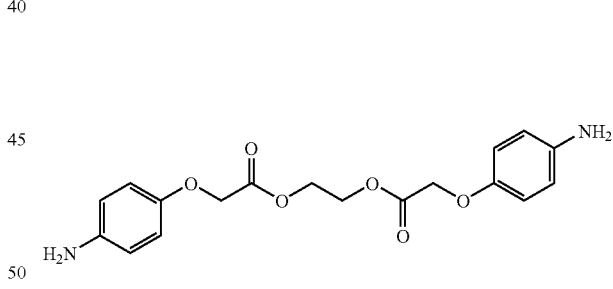

(4-Nitro-phenoxy)-acetic acid-2-[2-(4-nitro-phenoxy)-acetoxy]-ethyl ester 5 (100 grams, 238 mmoles) was dissolved in dry dimethylformamide (500 ml) in a pressure vessel, palladium on carbon (5%, 22 grams) added, and the mixture was stirred under hydrogen atmosphere (4 Kg) for 6 hours. The catalyst was removed by filtration and to the filtrate was added ice-cold water (2.5 lit). Crude 6 was filtered off, dried and recrystallised in a mixture of methanol:chloroform (1:1) to give pure 6 (65 grams, 78%) as a light brown shining powder. m.p: 124-125.8° C. The pure product 6 was also characterized using $^1$H NMR spectroscopy in CDCl$_3$: δ 4.40 (s, 2H, OCOCH2), 4.50 (s, 2H, OCH$_2$), 6.54 (d, 2H, Ar), 6.70 (d, 2H, Ar), 7.26 (s, 2H, NH$_2$).

Example 7

6-Bromo-hexanoic acid 2-(6-bromo-hexanoyloxy)-ethyl ester

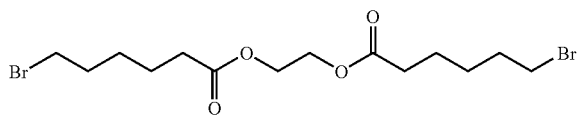

A solution of ethylene glycol (5 grams, 80.55 mmoles), 6-bromohexanoic acid (47 grams, 240.96 mmoles) and para-toluenesulphonic acid (0.5 gram) in toluene (150 ml) in a 500 ml 4 neck round bottom flask equipped with a mechanical stirrer and dean-stark apparatus was refluxed for 4 hours and cooled to room temperature. The toluene layer was washed with water (2×100 ml), 5% sodium bicarbonate solution (3×50 ml), water (2×100 ml), dried over sodium sulphate and distilled to get example 7 (30 grams, 91%) as a light yellow syrup with a melting point of 44° C. The pure product 7 was also characterized using $^1$H NMR spectroscopy in CDCl$_3$: δ 1.45 (m, 2H, CH$_2$), 1.59 (m, 2H, CH$_2$), 1.82 (m, 2H, CH$_2$), 2.26 (t, 2H, CH$_2$), 3.34 (t, 2H, CH$_2$), 4.18 (s, 2H, CH$_2$).

Example 8

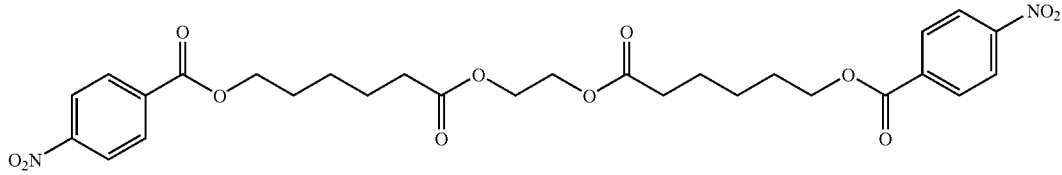

To a solution of 4-nitrobenzoic acid (12 grams, 71.80 mmoles), triethylamine (11 grams, 108.70 mmoles) in dimethylformamide (25 ml) was added 7 (10 grams, 24.02 mmoles) drop wise and stirred at room temperature for 16 hours. The solids were filtered off, the dimethylformamide solution was added onto 5% sodium bicarbonate solution (1 lit), crude 8 was extracted into chloroform, dried over sodium sulphate distilled and purified by column chromatography on silica gel using toluene as eluant to get pure 8 (9 grams, 63.8%) as a light cream powder. m.p: 71-73° C. The pure product 8 was also characterized using $^1$H NMR spectroscopy in CDCl$_3$: δ1.50 (m, 2H, CH$_2$), 1.80 (m, 4H, CH$_2$), 2.36 (t, 2H, CH$_2$), 4.26 (s 2H, CH$_2$), 4.34 (t, 2H, CH$_2$), 8.28 (dd, 4H, Ar).

Example 9

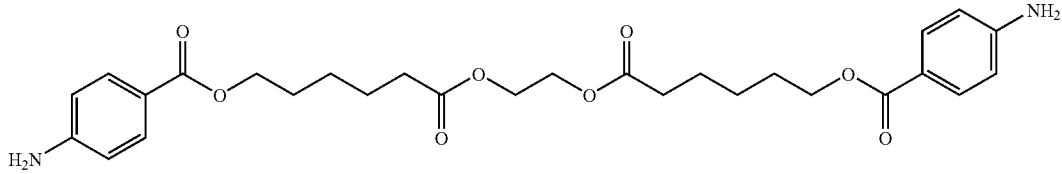

The compound from Example 8 (25 grams, 44.283 mmoles) was dissolved in DMF (200 ml) in a pressure vessel, Raney-Nickel (15 grams) added and the mixture stirred under hydrogen atmosphere (4 Kg) for 24 hours. The catalyst was removed by filtration, DMF distilled under vacuum and crude 9 was purified by column chromatography using chloroform: Ethyl acetate (9:1) as eluent to get pure 9 (15 grams, 67.2%) as a light brown powder. m.p: 70-73° C. The pure product 9 was also characterized using $^1$H NMR spectroscopy in CDCl$_3$: δ1.46 (m, 2H, CH$_2$), 1.70 (m, 4H, CH$_2$), 2.32 (t, 2H, CH$_2$), 4.14 (bs, 2H, NH$_2$), 4.20 (s &t, 4H, CH$_2$), 6.56 (d, 2H, Ar), 7.80 (d, 2H, Ar).

Hydrolysis
Example-2—0.5 grams
Aldrich pH9 buffer—50 ml
Temperature—100° C.
Hydrolyzed in 15 hours (By TLC 90% hydrolyzed)

Example 10

Chloro-Acetic Acid 3-(2-Chloro-Acetoxy)-Propyl Ester

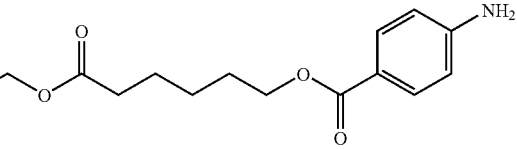

A solution of 1,3-propanediol (25 grams, 328.55 mmoles), chloroacetic acid (94 grams, 984.39 mmoles) and para-toluenesulphonic acid (1 gram) in toluene (250 ml) in a 1 lit, 4 neck round bottom flask equipped with a mechanical stirrer and dean-stark apparatus was refluxed for 8 hours, cooled to room temperature. The toluene layer was washed with water (2×300 ml), 5% sodium bicarbonate solution (3×300 ml), water (2×300 ml), dried over sodium sulphate and distilled to get crude 10, which was purified by high vacuum distillation to get example 10 (72 grams, 95.6%) as colorless liquid. The pure product 10 was also characterized using $^1$H NMR spectroscopy in CDCl$_3$: δ 2.10 (m, 2H, CH$_2$), 4.08 (s, 4H, CH$_2$), 4.30 (t, 4H, CH$_2$).

Example 11

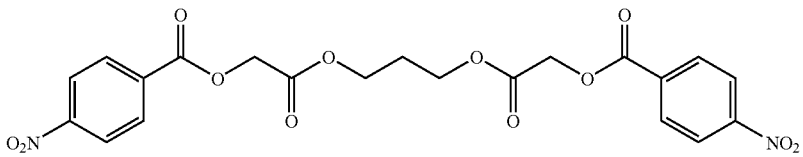

To a solution of 4-nitrobenzoic acid (32.8 grams, 196.26 mmoles), triethylamine (30 grams, 296.47 mmoles) in dimethylformamide (40 ml) was added 10 (15 grams, 65.48 mmoles) in small portions and stirred at room temperature for 6 hours. The solids were filtered off, the dimethylformamide solution was added onto 5% sodium bicarbonate solution (150 ml), filtered crude 11, recrystallised in chloroform:methanol (1:1) to get pure 11 (9 grams, 28.1%) as a light cream powder. m.p: 120-121.8° C. The pure product 11 was also characterized using $^1$H NMR spectroscopy in CDCl$_3$: δ 2.08 (m, 1H, CH), 4.30 (t, 2H, CH$_2$), 4.88 (s, 2H, CH$_2$), 8.30 (dd, 4H, Ar).

Example 12

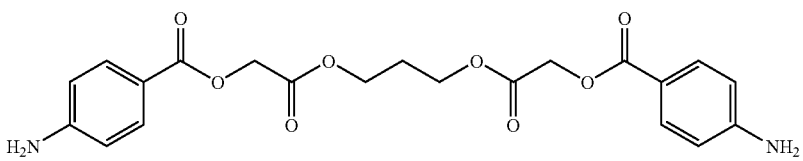

The compound from Example 11 (5 grams, 10.20 mmoles) was dissolved in dimethylformamide (100 ml) and methanol (100 ml) in a pressure vessel, Raney-Nickel (3 grams) added and the mixture stirred under hydrogen atmosphere (4 Kg) for 24 hours. The catalyst was removed by filtration, solvent distilled under vacuum, added ice water (20 ml), filtered crude 12 which was recrystallised from a mixture of dimethylformamide:methanol (1:7) to get pure 12 (3 grams, 68.49%) as a light brown powder. m.p: 130.3-132.4° C. (Corrected to 142-144° C.). The pure product 12 was also characterized using $^1$H NMR spectroscopy in DMSO-d$_6$: δ 2.00 (m, 1H, CH$_2$), 4.22 (t, 2H, CH$_2$), 4.74 (s, 2H, CH$_2$), 5.36 (bs, 2H, NH$_2$), 6.60 (d, 2H, Ar), 7.74 (d, 2H, Ar).

Hydrolysis

Example-12—0.5 grams

Aldrich pH9 buffer—50 ml

Temperature—100° C.

Hydrolyzed in 29 hours (by TLC 90% hydrolyzed)

Example 13

Synthesis of Chloro-Acetic Acid 3-(2-Chloro-Acetoxy)-2,2-Bis-(2-Chloro-Acetoxymethyl)-Propyl Ester

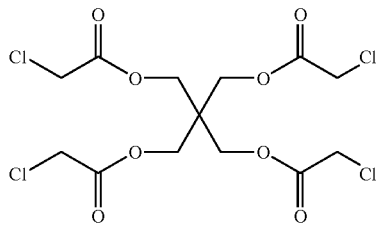

A solution pentaerythritol (25 grams, 183.62 mmoles), chloroacetic acid (105.2 grams, 1.10 moles) and para-toluenesulphonic acid (2 gram) in toluene (500 ml) in a 2 lit 4 neck round bottom flask equipped with a mechanical stirrer and dean-stark apparatus was refluxed for 8 hours, cooled to room temperature. The toluene layer was washed with water (2×300 ml), 5% sodium bicarbonate solution (3×500 ml), water (2×300 ml), dried over sodium sulphate and distilled to get crude 13, which was purified by recrystallization from chloroform:hexane (1:7) to get pure 13 (77 grams, 94.8%), as a white powder with a melting point of 94-96° C. The pure product 13 was also characterized using $^1$H NMR spectroscopy in CDCl$_3$: δ 4.16 (s, 2H, CH$_2$), 4.28 (s, 2H, CH$_2$).

Example 14

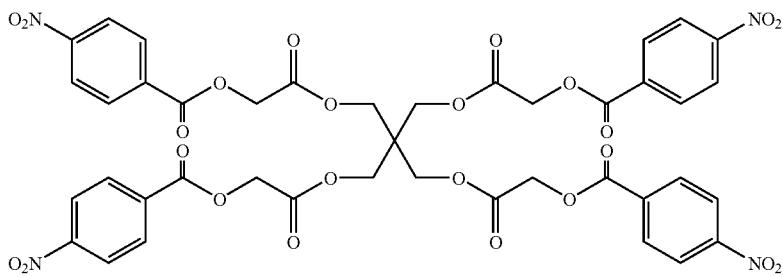

To a solution of 4-nitrobenzoic acid (11.3 grams, 67.61 mmoles), triethylamine (9.2 grams, 90.91 mmoles) in dimethylformamide (25 ml) was added chloroacetic acid 3-(2-chloro-acetoxy)-2,2-bis-(2-chloro-acetoxymethyl)-propyl ester 13 (5 grams, 11.31 mmoles) in small portions and stirred at room temperature for 5 hours. The solids were filtered off; the dimethylformamide solution was added onto 5% sodium bicarbonate solution (1 lit), filtered, washed with methanol and dried to get 14 (9 grams, 83.6%) as an off-white powder. Analytical sample was prepared by column chromatography on silica gel using chloroform as eluant. m.p: 117-121° C. The pure product 14 was also characterized using $^1$H NMR spectroscopy in CDCl$_3$: δ 4.14 (s, 2H, CH$_2$), 4.84 (s, 2H, CH$_2$), 8.25 (dd, 4H, Ar)

Example 15

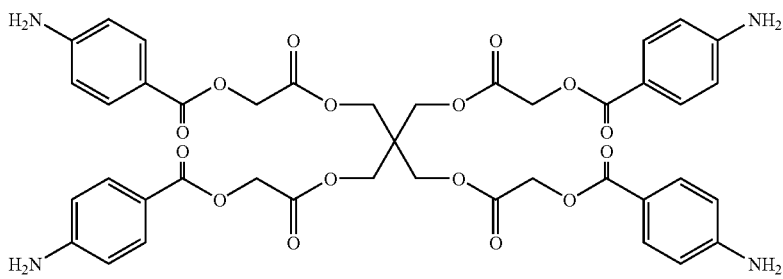

The compound from Example L4 (25 grams, 26.26 mmoles) was dissolved in dimethylformamide (100 ml) in a pressure vessel, Raney-Nickel (10 grams) added and the mixture stirred under hydrogen atmosphere (4 Kg) for 5 hours. The catalyst was removed by filtration, and 15 was precipitated by adding methanol, filtered, dried to get pure 15 (20 grams, 91.5%) as a white fluffy powder with a melting point of 192-194.4° C. The pure product 15 was also characterized using $^1$H NMR spectroscopy in DMSO-d$_6$: δ4.25 (s, 2H, CH$_2$), 4.81 (s, 2H, CH$_2$), 6.09 (bs, 2H, NH$_2$), 6.55 (d, 2H, Ar), 7.67 (d, 2H, Ar).

Hydrolysis
Example-15—0.5 grams
Aldrich pH9 buffer—50 ml
Temperature—100° C.
Hydrolyzed in 6 hours

Example 16

Synthesis of Chloro-Acetic Acid 2,3-Bis-(2-Chloro-Acetoxy)-Propyl Ester

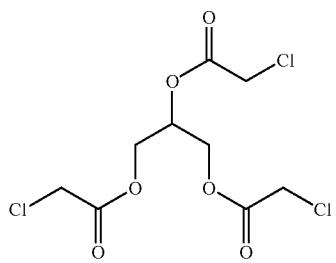

A solution of glycerol (25 grams, 271.47 mmoles), chloroacetic acid (116 grams, 1.214 moles) and para-toluenesul phonic acid (2 gram) in toluene (500 ml) in a 2 lit 4 neck round bottom flask equipped with a mechanical stirrer and dean-stark apparatus was refluxed for 6 hours, cooled to room temperature. The toluene layer was washed with water (2×300 ml), 5% sodium bicarbonate solution (3×500 ml), water (2×300 ml), dried over sodium sulphate and distilled to get crude 16 (67 grams, 76%) as a colorless liquid.

Example 17

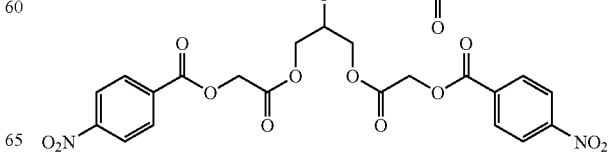

To a solution of 4-nitrobenzoic acid (23.4 grams, 140.01 mmoles), triethyl amine (18.9 grams, 186.77 mmoles) in dimethylformamide (30 ml) was added chloroacetic acid 2,3-bis-(2-chloro-acetoxy)-propyl ester 16 (10 grams, 31.09 mmoles) in small portions and stirred at room temperature for 16 hours. The solids were filtered off, the dimethylformamide solution was added onto 5% sodium bicarbonate solution (500 ml), extracted into chloroform washed with water (2×50 ml), dried over sodium sulphate, distilled to get crude 17, which was purified by column chromatography on silica gel using toluene as eluant to get pure 17 (6 grams, 27%) as a light yellow syrup. The pure product 17 was also characterized using $^1$H NMR spectroscopy in DMSO-$d_6$: δ 4.42 (m, 4H, $CH_2$), 4.92 (overlapped s, 6H, $CH_2$), 5.42 (m, 1H, CH), 8.28 (overlapped d, 12H, Ar).

Example 18

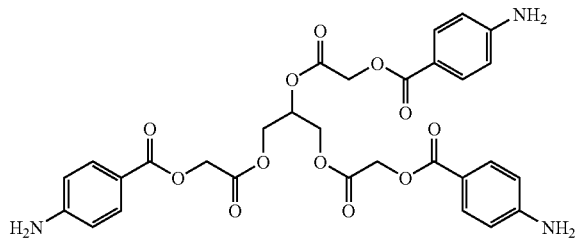

The compound from Example 17 (10 grams, 14.02 mmoles) was dissolved in dimethylformamide (150 ml) in a pressure vessel, Raney-Nickel (15 grams) added and the mixture stirred under hydrogen atmosphere (4 Kg) for 16 hours. The catalyst was removed by filtration, filtrate poured on to ice water (300 ml), extracted with ethyl acetate dried over sodium sulphate, treated with charcoal filtered and distilled off the solvent under vacuum to get pure 18 (6 grams, 68.7%) as a light yellow syrup. The pure product 18 was also characterized using $^1$H NMR spectroscopy in a mixture of $CDCl_3$ and DMSO-$d_6$: δ 4.35 (m, 4H, $CH_2$), 4.78 (over lapped s, 6H, $CH_2$), 5.30 (m, 1H, CH), 6.62 (d, 2H, Ar), 7.70 (d, 2H, Ar)

Hydrolysis
Example-18—0.5 grams
Aldrich pH9 buffer—50 ml
Temperature—100° C.
Hydrolyzed in 10 hours Example 19

Chloro-Acetic Acid 4-(2-Chloro-Acetoxy)-Butyl Ester

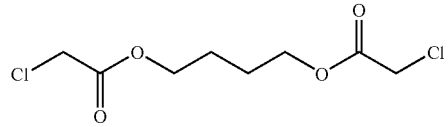

A solution 1,4-butanediol (75 grams, 832.22 mmoles), chloroacetic acid (240 grams, 2.513 moles) and para-toluene-sulphonic acid (3 grams) in toluene (750 ml) in a 2 lit 4 neck round bottom flask equipped with a mechanical stirrer and dean-stark apparatus was refluxed for 6 hours, cooled to room temperature. The toluene layer was washed with water (2×300 ml), 5% sodium bicarbonate solution (3×500 ml), water (2×300 ml), dried over sodium sulphate and distilled to get crude 19, which was purified by recrystallization in chloroform:hexane (1:7) to get pure 19 (92 grams, 69.8%) as a white fluffy powder. m.p: 74-76.5° C. The pure product 19 was also characterized using $^1$H NMR spectroscopy in $CDCl_3$: δ 1.78 (t, 2H, $CH_2$), 4.05 (s, 2H, $CH_2$), 4.25 (t, 2H, $CH_2$).

Example 20

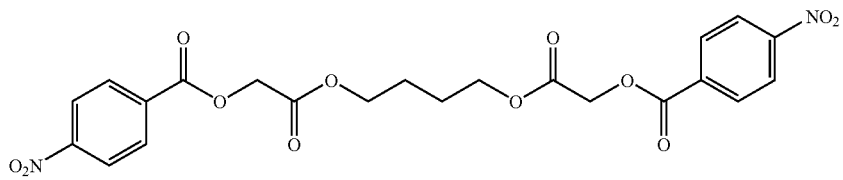

To a solution of 4-nitrobenzoic acid (10.3 grams, 61.63 mmoles), triethylamine (10.4 grams, 102.77 mmoles) in dimethylformamide (25 ml) was added chloroacetic acid 4-(2-chloro-acetoxy)-butyl ester 19 (5 grams, 20.56 mmoles) in small portions and stirred at room temperature for 16 hours. The solids were filtered off, the dimethylformamide solution was added onto 5% sodium bicarbonate solution (250 ml), filtered, crude 25, recrystallized in chloroform:hexane (1:7) to get pure 20 (4.8 grams, 46.3%) as a white powder. m.p: 122.5-125° C. The pure product 20 was also characterized using $^1$H NMR spectroscopy in $CDCl_3$: δ 1.78 (t, 2H, $CH_2$), 4.24 (t, 2H, $CH_2$), 4.86 (s, 2H, $CH_2$) 8.32 (dd, 4H, Ar).

Example 21

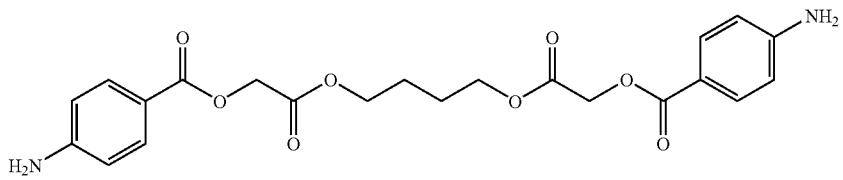

The compound from Example 20 (25 grams, 49.60 mmoles) was dissolved in dimethylformamide (200 ml) in a pressure vessel, Raney-Nickel (15 grams) added and the mixture stirred under hydrogen atmosphere (4 Kg) for 18 hours. The catalyst was removed by filtration and to the filtrate was added ice water (500 ml), filtered, dried and washed with hot ethyl acetate to get pure 21 (14 grams, 63.5%) as a white powder. m.p: 192.7-195.4. The pure product 21 was also characterized using $^1$H NMR spectroscopy in (DMSO-$d_6$) δ 1.75 (t, 2H, $CH_2$), 4.17 (t, 2H, $CH_2$), 4.85 (s, 2H, $CH_2$), 6.15 (s, 2H, $NH_2$), 6.67 (d, 2H, Ar), 7.80 (d, 2H, Ar).
Hydrolysis
Example-21—0.5 grams
Aldrich pH 9 buffer—50 ml
Temperature—100° C.
Hydrolyzed in 24 hours (By TLC 95% hydrolyzed)

Example 22

Chloro-acetic acid 2-[2-(2-chloro-acetoxy)-ethoxy]-ethyl ester

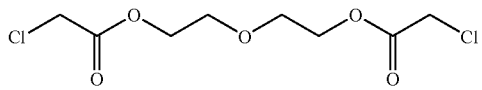

A solution diethyleneglycol (25 grams, 231.20 mmoles), chloroacetic acid (66 grams, 691.17 mmoles) and para-toluenesulphonic acid (1 gram) in toluene (350 ml) in a 1 lit 4 neck round bottom flask equipped with a mechanical stirrer and dean-stark apparatus was refluxed for 6 hours, cooled to room temperature. The toluene layer was washed with water (2×300 ml), 5% sodium bicarbonate solution (3×500 ml), water (2×300 ml), dried over sodium sulphate and distilled to get 22 (56 grams, 93.4%) as light yellow syrup. The pure product 22 was also characterized using $^1$H NMR spectroscopy in $CDCl_3$: δ 3.75 (t, 2H, $CH_2$), 4.12 (s, 2H, $CH_2$), 4.36 (t, 2H, $CH_2$)

Example 23

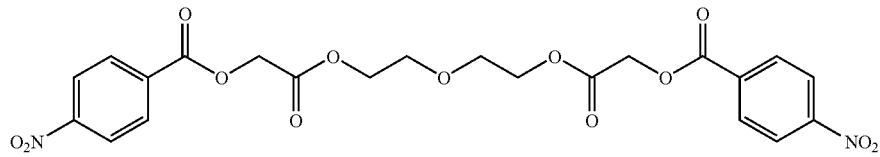

To a solution of 4-nitro benzoic acid (29 grams, 173.52 mmoles), triethylamine (29 grams, 286.58 mmoles) in dimethylformamide (75 ml) was added 22 (15 grams, 57.89 mmoles) drop wise and stirred at room temperature for 18 hours. The solids were filtered off, dimethylformamide solution was added on to ice water (300 ml), extracted with chloroform, washed with 5% sodium bicarbonate solution (3×50 ml), water (100 ml), dried over sodium sulphate, distilled to get crude 23 which was purified by column chromatography on silica gel using benzene as eluant to get pure 23 (10 grams, 33.22%) as light cream powder. m.p: 62-64° C. The pure product 23 was also characterized using $^1$H NMR spectroscopy in $CDCl_3$: $^1$H NMR ($CDCl_3$) δ 3.72 (t, 2H, $CH_2$), 4.34 (t, 2H, $CH_2$), 4.92 (s, 2H, $CH_2$), 8.30 (overlapped d, 4H, Ar).

Example 24

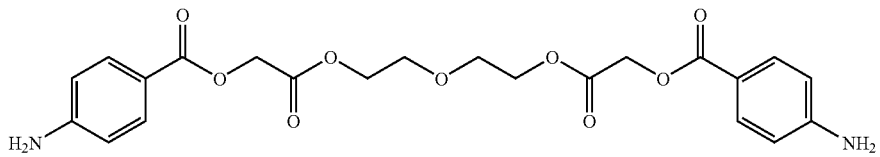

The compound from Example 23 (80 grams, 173.91 mmoles) was dissolved in dimethylformamide (300 ml) in a pressure vessel, Raney-Nickel (40 grams) added and the mixture stirred under an atmosphere of hydrogen (4 Kg) for 16 hours. The catalyst was removed by filtration and to the filtrate was added ice water (700 ml), filtered, dried and washed with hot methanol to get pure 24 (56.6 grams, 80%) as a white powder. m.p: 136-137° C. The pure product 24 was also characterized using H NMR spectroscopy in a mixture of $CDCl_3$ and $DMSO-d_6$: δ 3.62 (t, 2H, $CH_2$), 4.20 (t, 2H, $CH_2$), 4.81 (s, 2H, $CH_2$), 6.08 (s, 2H, $NH_2$), 6.58 (d, 2H, Ar), 7.78 (d, 2H, Ar).
Hydrolysis
Example-24—0.5 grams
Aldrich pH9 buffer—50 ml
Temperature—100° C.
Hydrolyzed in 3 hours

Example-25

Chlorocarbonylmethoxy-Acetyl Chloride

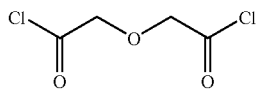

A solution of diglycolic acid (100 grams, 745.76 mmol) and thionyl chloride (125 ml, 1.713 mol) was refluxed for 5 hours. Excess thionyl chloride was distilled off and the acid chloride was purified by high vacuum distillation to get pure product 25 (110 grams, 86.2%) as a light yellow liquid. bp: 84-87° C./2 mm Hg.

Example-26

(4-Nitro-Phenoxycarbonylmethoxy)-Acetic Acid 4-Nitro-Phenyl Ester

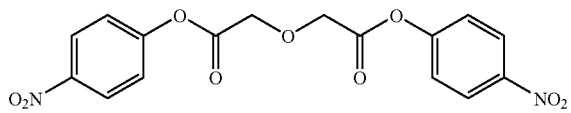

To a solution of 4-nitrophenol (81.35 grams, 584.78 mmol) and pyridine (47.3 ml, 584.82 mmol) in chloroform at 0° C. under $N_2$ atmosphere was added diglycolyl chloride 25 (50 grams, 292.43 mmol) drop wise. Further stirred at 0° C. for 8 hours, filtered the separated solid, and discarded the chloroform layer which continued unreacted 4-Nitrophenol along with some product. The filtered solid was taken into water (2000 ml), extracted with ethyl acetate (3×300 ml), the combined ethyl acetate layer washed with 5% sodium bicarbonate (3×300 ml), water (1×300 ml), dried over sodium sulphate, distilled off 80% ethyl acetate and to the residue added hexane (250 ml), filtered the precipitated product to get dinitro compound 26 (60 grams) as white powder. mp: 161.8-163.6° C., Mass: M+Na=399. The pure product 26 was also characterized using $^1$H NMR spectroscopy in $DMSO-d_6$: δ 4.64 (s, 2H, $CH_2$), 7.42 (d, 2H, Ar), 8.36 (d, 4H, Ar).
HPLC Conditions
Column: Inertsil C-18, 250×4.6 mm 5.0 μm
Flow: 1.000 ml/min
Mobile Phase: A (20% Water): B (80% ACN)
Purity: 99.035%

Example-27

(4-Amino-Phenoxycarbonylmethoxy)-Acetic Acid 4-Amino-Phenyl Ester

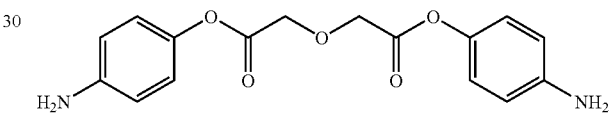

(4-nitro-phenoxycarbonylmethoxy)-acetic acid 4-nitrophenyl ester 26 (10 grams, 26.59 mmoles) was dissolved in dimethylformamide (100 ml) in a pressure vessel, 10% palladium carbon (3 grams, 50% wet) added and the mixture stirred under an atmosphere of hydrogen (3 Kg) for 4 hours. The catalyst was removed by filtration, and diamine was precipitated by adding water, filtered, dried and recrystallised from ethyl acetate to get pure diamine 27 (4 grams, 47.6%) as off-white powder. m.p: 122-123° C. The pure product 27 was also characterized using $^1$H NMR spectroscopy in $DMSO-d_6$: δ 4.47 (s, 2H, $CH_2$), 5.04 (s, 2H, $NH_2$), 6.54 (d, 2H, Ar), 6.79 (d, 2H, Ar).
HPLC Conditions
Column: Inertsil C-18, 250×4.6 mm 5.0 μm
Flow: 0.600 ml/min
Mobile Phase: D (50% Water): A (50% ACN)
Purity: 99.037%

Example-28

(4-Isocyanato-Phenoxycarbonylmethoxy)-Acetic Acid 4-Isocyanato-Phenyl Ester

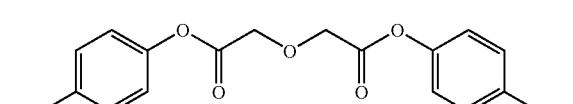

To a solution of (4-amino-phenoxycarbonylmethoxy)-acetic acid 4-amino-phenyl ester (27) (2 grams, 6.32 mmoles) in dry 1,4-dioxane (32 ml) under nitrogen atmosphere was cooled to 10° C. and added a solution of diphosgene (4 grams, 13.47 mmoles) in 1,4-dioxane (8 ml) in one lot and heated to a temperature of 100° C. for 2 hours. The condenser was then arranged for distillation and solvent removed by distillation at atmospheric pressure until the volume of the reaction mixture was reduced to approximately one third. Fresh dry dioxane (10 ml) was added and distilled off the solvents under vacuum. The residue was re-evaporated two times from dry dioxane (2×10 ml) to give crude 28 (4-Isocyanato-phenoxy-carbonylmethoxy)-acetic acid 4-isocyanato-phenyl ester, which was recrystallized from toluene as a white powder with a melting point of 150.5-152.4° C., IR: 2316.1 cm$^{-1}$, 2274.3 cm$^{-1}$. The pure product 28 was also characterized using $^1$H NMR spectroscopy in CDCl$_3$: δ 4.56 (s, 2H, CH$_2$), 7.10 (s, 4H, Ar).

Example 29

Synthesis of (2-Bromo-Ethoxy)-Acetic Acid

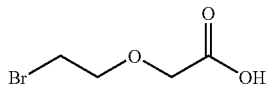

To 48% hydrobromic acid (372 ml) at 0° C. was added drop wise concentrated sulphuric acid (84.1 ml) and stirred for 10 minutes. At this temperature was added para dioxanone (70 grams, 685.6 mmol) followed by further stirring at room temperature for 1 hour. The reaction mixture was then was heated at 100° C. for 2 hours 30 minutes, followed by overnight cooling at room temperature. The reaction mixture was taken in to ice water, extracted with ethyl acetate (4×250 ml), dried over sodium sulphate, distilled to get crude acid 29 (98 grams) with a GC purity of 78.1%, which was fractionated under high vacuum two times to get 50 grams of acid 29 as a light yellow liquid with a purity of 90% as determined by gas chromatography (GC). The pure product 29 was also characterized using $^1$H NMR spectroscopy in CDCl$_3$: δ 3.49 (t, 2H, CH$_2$), 3.89 (t, 2H, CH$_2$), 4.20 (s, 2H, CH$_2$), 8.56 (bs, 1H, COOH).

Example 30

Synthesis of (2-Bromo-ethoxy)-acetic acid 2-[2-(2-bromo-ethoxy)-acetoxy]-ethyl ester

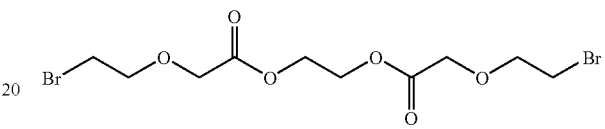

A solution ethylene glycol (7.5 grams, 120.83 mmoles), (2-Bromo-ethoxy)-acetic acid 29 (48.6 grams, 265.57 mmoles) and para-toluenesulphonic acid (0.3 grams) in toluene (400 ml) in a 1 lit 4 neck round bottom flask equipped with a mechanical stirrer and dean-stark apparatus was refluxed for 8 hours followed by cooling to room temperature. The toluene layer was washed with water (2×50 ml), 5% sodium bicarbonate solution (2×50 ml), water (2×50 ml) and dried over sodium sulphate and distilled to get crude 30 (33 grams, 69.7%) as light yellow liquid. GC purity: 86.4%. The pure product 30 was also characterized using $^1$H NMR spectroscopy in CDCl$_3$: δ 3.48 (t, 2H, CH$_2$), 3.88 (t, 2H, CH$_2$), 4.14 (s, 2H, CH$_2$), 4.38 (s, 2H, CH$_2$).

Example 31

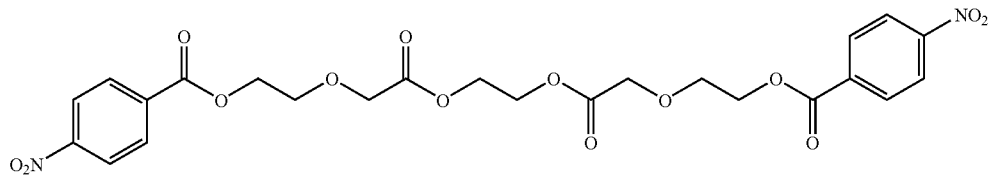

To a solution of 4-nitro benzoic acid (40.3 grams, 241.02 mmoles) and 30 (2-Bromo-ethoxy)-acetic acid 2-[2-(2-bromo-ethoxy)-acetoxy]-ethyl ester (16.6 grams, 42.33 mmoles) in dimethylformamide (80 ml) was added a solution of triethylamine (21.4 grams, 211.48 mmoles) in dimethylformamide (20 ml) drop wise and stirred at 50° C.-60° C. for 24 hours. The solids were filtered off, the dimethylformamide solution was added onto water (125 ml), extracted with ethyl acetate, washed with 5% sodium bicarbonate solution (2×25 ml), water (2×25 ml), dried over sodium sulphate and distilled to get crude dinitro PDO 31 which was purified by column chromatography on silica gel using chloroform as eluant to get dinitro PDO as light yellow syrup (7 grams) which over a period of 3 days crystallized to a solid which was slurried in hexane to get pure 31 dinitro (5 grams) as off white powder with a melting point of 75.5-78° C., The pure product 31 was also characterized using $^1$H NMR spectroscopy in CDCl$_3$: δ3.90 (t, 2H, CH$_2$), 4.15 (s, 2H, CH$_2$), 4.37 (s, 2H, CH$_2$), 4.55 (t, 2H, CH$_2$), 8.26 (dd, 4H, Ar)

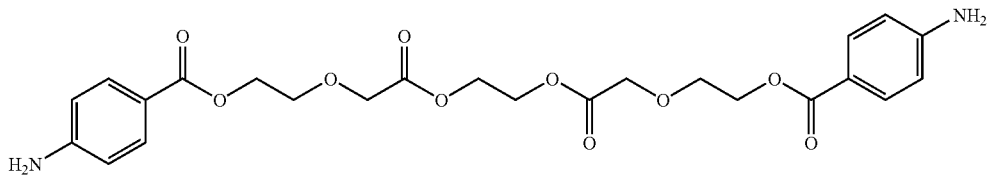

Dinitro PDO 31 (2 grams, 3.54 mmoles) was dissolved in ethyl acetate (50 ml) in a pressure vessel, palladium carbon (10%, 50% wet, 1 gram) added and the mixture stirred under hydrogen atmosphere (3 Kg) for 2 hours. The catalyst was removed by filtration, ethyl acetate dried over sodium sulphate and distilled to get crude diamine 32 (1.4 grams, 78.6%) as light yellow syrup. The crude product 32 was also characterized using $^1$H NMR spectroscopy in a mixture of $CDCl_3$ and $DMSO\text{-}d_6$: δ 3.84 (t, 2H, $CH_2$), 4.15 (s, 2H, $CH_2$), 4.30 (s, 2H, $CH_2$), 4.36 (t, 2H, $CH_2$), 5.15 (bs, 2H, $NH_2$), 6.56 (d, 2H, Ar), 7.72 (d, 2H, Ar).

Example 33

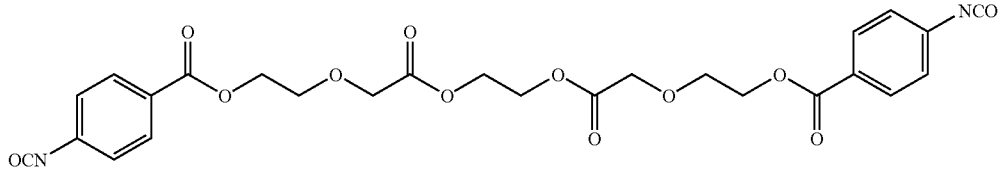

This monomer is prepared from diamine 32 using the procedures described in Example 28 of the present patent application.

Example 34

Synthesis of Diglycolic Acid Diacid

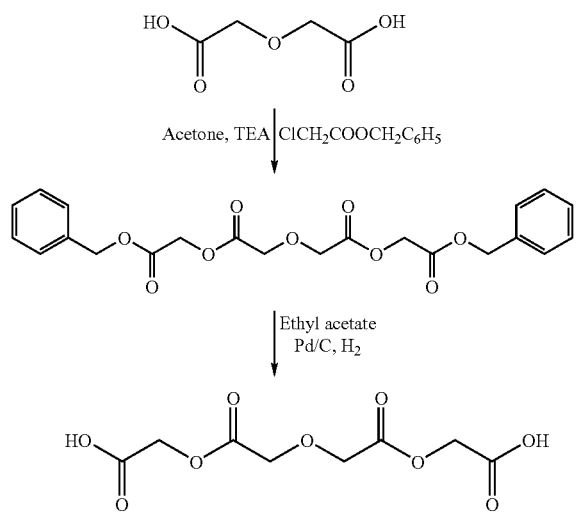

Step 1. Synthesis of benzylated diglycolic acid diglycolate: Into a clean and dry 2 liter, 4 necked round bottom flask equipped with a desiccant tube was added 100 grams of diglycolic acid and 500 ml of Acetone. The flask was placed in an oil bath maintained at room temperature and placed on a magnetic stirrer. To this stirring solution of diglycolic acid and acetone was added 311.8 ml of triethylamine followed by stirring at room temperature for 10 minutes. 302 grams of benzyl chloroacetate was added dropwise to the stirring solution using dropping funnel. The resulting solution was left for stirring at room temperature overnight. The progress of the reaction was monitored using thin layer chromatography. Once the reaction was complete, it was filtered and washed with acetone. The filtrate was precipitated in 2 liters of cold water and extracted three times each with 300 ml of ethyl acetate. The ethyl acetate fraction was dried using sodium sulfate. Ethyl acetate was distilled off and the crude compound was precipitated with 300 ml of hexane. The precipitated crude product was filtered to yield 280 grams of white powder. The crude product was finally recrystallized using a mixture of hexane and ethyl acetate to yield 260 grams of pure benzylated diglycolic acid diglycolate with a melting point of 56-58° C. Benzylated diglycolic acid diglycolate was also characterized using $^1$H NMR spectroscopy in $CDCl_3$, δ 3.32 (s, 2H, $CH_2$), 4.67 (s, 2H, $CH_2$), 5.18 (s, 2H, $CH_2$), 7.32 (s, 5H, Ar). Benzylated diglycolic acid diglycolate undergoes 90% hydrolysis to diglycolic acid in 23 hours at pH 7.0 and 100° C.

Step 2. Debenzylation of benzylated diglycolic acid diacid: Into a hydrogenation apparatus was added 100 grams of benzylated diglycolic acid diglycolate dissolved in 250 ml of ethyl acetate. 2 grams of 10% palladium on carbon was added to the solution and the resulting reaction mixture in the pressure vessel was purged with hydrogen maintained at a pressure of 3 kg and stirred for 6 hours. The completion of reaction was determined by disappearance of starting material using thin layer chromatography. The reaction mixture after completion was filtered using the high flow bed and washed with ethyl acetate. Ethyl acetate was distilled off to yield 55 grams of crude diglycolic acid diacid with a melting point of 90-96° C. The resulting crude product was purified via crystallization using a mixture of ethyl acetate and hexane to yield 40 grams of pure diglycolic acid diacid with a melting point of 96-99° C. Pure diglycolic acid diacid was also characterized using $^1$H NMR ($CDCl_3$) δ 4.35 (s, 2H, $CH_2$), 4.46 (bs, 1H, COOH), 4.62 (s, 2H, $CH_2$). Diglycolic acid diacid undergoes 100% hydrolysis to diglycolic acid in 6 hours at pH 7.0 and 100° C.

Example 35

Synthesis of Caprolactone Functionalized Diglycolic Acid

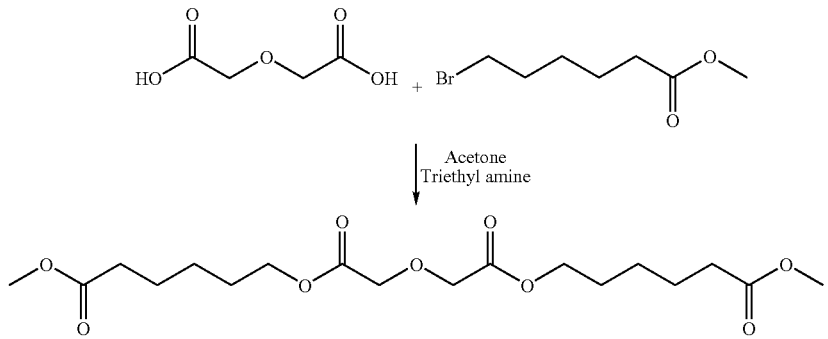

Into a clean and dry 1 liter, 4 necked round bottom flask equipped with a desiccant tube was added 30 grams of diglycolic acid and 150 ml of dimethylformamide (DMF). The flask was placed in an oil bath maintained at room temperature and placed on a magnetic stirrer. To this stirring solution of diglycolic acid and DMF was added 26 ml of triethylamine followed by stirring at room temperature for 10 minutes. 31.7 grams of 6-bromohexanoate was added dropwise to the stirring solution using dropping funnel. The resulting solution was left for stirring at room temperature overnight. The progress of the reaction was monitored using thin layer chromatography. Once the reaction was complete, it was filtered and washed with acetone. The filtrate was precipitated in 250 ml of cold water and extracted three times each with 50 ml of ethyl acetate. The ethyl acetate fraction was washed four times each with 50 ml of 10% solution of sodium bicarbonate followed by washing with 100 ml of water. The ethyl acetate layer was dried using sodium sulfate. Ethyl acetate was distilled off to yield 24 grams of crude product. The crude product was washed with 75 ml of hexane and dried using high vacuum to yield 13.5 grams of light yellow colored caprolactone functionalized diglycolic acid. Pure caprolactone functionalized diglycolic acid was also characterized using $^1$H NMR spectroscopy in CDCl$_3$, δ 1.4 (m, 2H, CH$_2$), 1.70 (m, 4H, CH$_2$×2), 2.32 (t, 2H, CH$_2$), 3.68 (s, 3H, COOCH$_3$), 4.18 (t, 2H, CH$_2$), 4.22 (s, 2H, CH$_2$). Caprolactone functionalized diglycolic acid undergoes 60% hydrolysis to diglycolic acid in 22 hours at pH 7.0 and

Example 36

Synthesis of Caprolactone Functionalized Diglycolic Acid Diacid

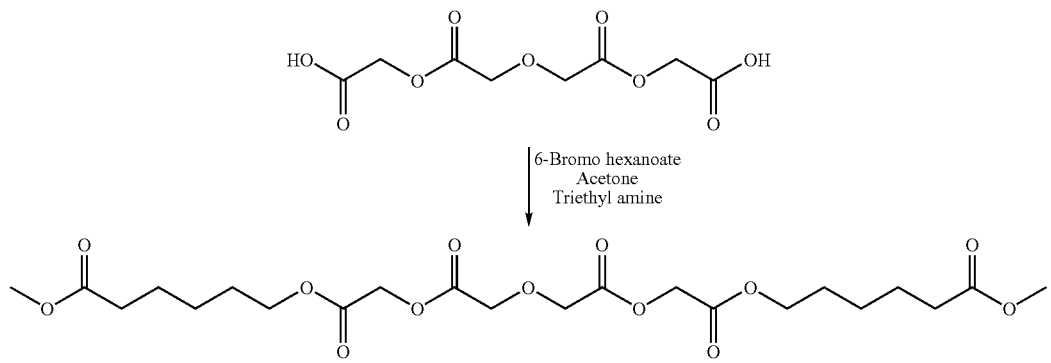

Into a clean and dry 1 liter, 4 necked round bottom flask equipped with a desiccant tube was added 25 grams of diglycolic diacid and 250 ml of dimethylformamide (DMF). The flask was placed in an oil bath maintained at room temperature and placed on a magnetic stirrer. To this stirring solution of diglycolic acid and DMF was added 35 ml of triethylamine followed by stirring at room temperature for 10 minutes. 43.5 grams of 6-bromohexanoate was added dropwise to the stirring solution using dropping funnel. The resulting solution was left for stirring at 70° C. for 32 hours. The progress of the reaction was monitored using thin layer chromatography.

Once the reaction was complete, it was precipitated in 250 ml of cold water and extracted four times each with 250 ml of methyl t-butyl ether (MTBE). The MTBE layer was washed four times each with 5% solution of sodium bicarbonate followed by washing with 200 ml of water. The MTBE layer was dried using sodium sulfate. MTBE was distilled off to yield 35 grams of crude product. The crude product was purified via column chromatography to yield 24 grams of light yellow colored caprolactone functionalized diglycolic acid diacid. Pure caprolactone functionalized diglycolic acid diacid was also characterized using $^1$H NMR spectroscopy in CDCl$_3$, δ 1.36 (m, 2H, CH$_2$), 1.63 (m, 4H, CH$_2$×2), 2.24 (t, 2H, CH$_2$), 3.6 (s, 3H, COOCH$_3$), 4.1 (t, 2H, CH$_2$), 4.2 (s, 2H, CH$_2$), 4.6 (s, 2H, CH$_2$).

Example 37

Synthesis of Polyester from Diglycolic Acid Diacid

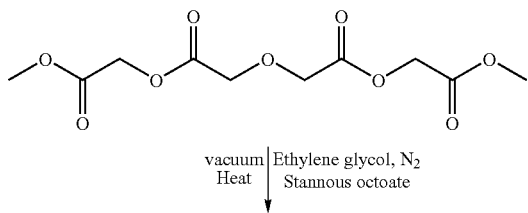

vacuum | Ethylene glycol, N$_2$
Heat | Stannous octoate

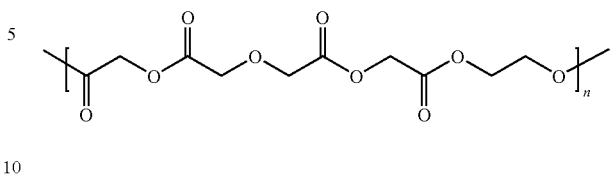

Into a clean and dry 100 ml, 3 necked round bottom flask equipped with a nitrogen inlet was added 10 grams of diglycolic diacid, 6.32 grams of ethylene glycol and 2 drops of stannous octanoate solution as a catalyst. The flask was placed in an oil bath maintained at 140° C. and placed on a magnetic stirrer. The temperature of the reaction mixture was increased to 180° C. after 2.5 hours. The reaction mixture was left for stirring at 190° C. for 6 hours following which the reaction temperature was reduced to 120° C. and a high vacuum was applied. The reaction was left for stirring at 120° C. under high vacuum for 28 hours. 11 grams of light brown colored syrupy polyester was isolated. Polyester undergoes 100% hydrolysis to diglycolic acid in 8 hours at pH 7.0 and 100° C.

Example 38

Synthesis of Polyester from Diglycolic Acid Dicaprolactone

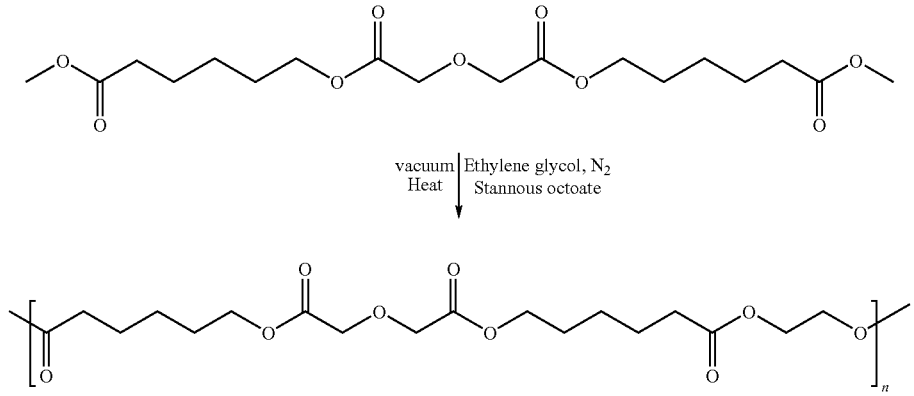

Into a clean and dry 100 ml, 3 necked round bottom flask equipped with a nitrogen inlet was added 10 grams of diglycolic dicaprolactone, 4.76 grams of ethylene glycol and 2 drops of stannous octanoate solution as a catalyst. The flask was placed in an oil bath maintained at 140° C. and placed on a magnetic stirrer for overnight. The temperature of the reaction mixture was increased to 160° C. after 18 hours. The reaction mixture was left for stirring at 160° C. for another 24 hours following which the reaction temperature was reduced to 100° C. and a high vacuum was applied for another 18 hours. The reaction was further increased to 120° C. under high vacuum for 8 hours followed by further increase to 140° C. for another 8 hours. 10 grams of light yellow colored syrupy polyester was isolated.

Example 39

Synthesis of Polyester from Diglycolic Acid Diacid Dicaprolactone

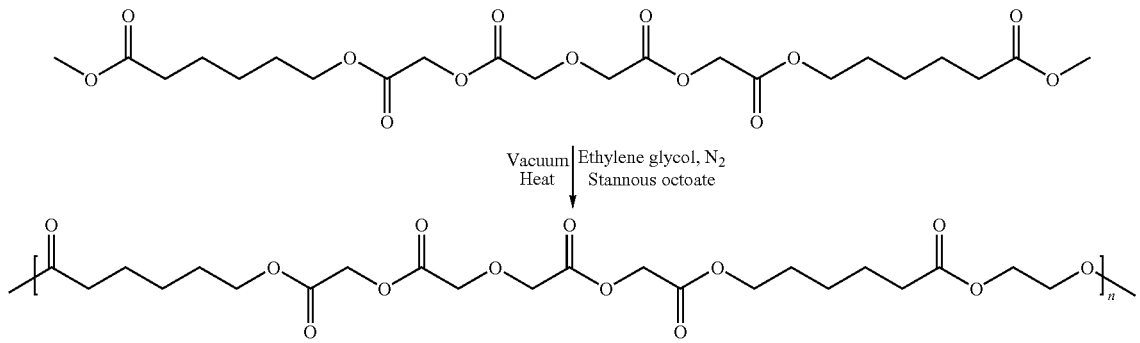

Into a clean and dry 100 ml, 3 necked round bottom flask equipped with a nitrogen inlet was added 10 grams of diglycolic dicaid dicaprolactone, 3.6 grams of ethylene glycol and 2 drops of stannous octanoate solution as a catalyst. The flask was placed in an oil bath maintained at 140° C. and placed on a magnetic stirrer for overnight. The temperature of the reaction mixture was increased to 160° C. after 18 hours. The reaction temperature was reduced to 100° C. and a high vacuum was applied for another 18 hours. The reaction was further increased to 140° C. under high vacuum for 8 hours followed by further increase to 140° C. for another 8 hours. 9.5 grams of light brown colored syrupy polyester was isolated. Polyester undergoes 100% hydrolysis to diglycolic acid in 15 hours at pH 7.0 and 100° C.

Hexanedioic acid
bis-(5-carboxypentyloxycarbonylmethyl) ester
(Adipic acid diglycolate dicaproic acid)

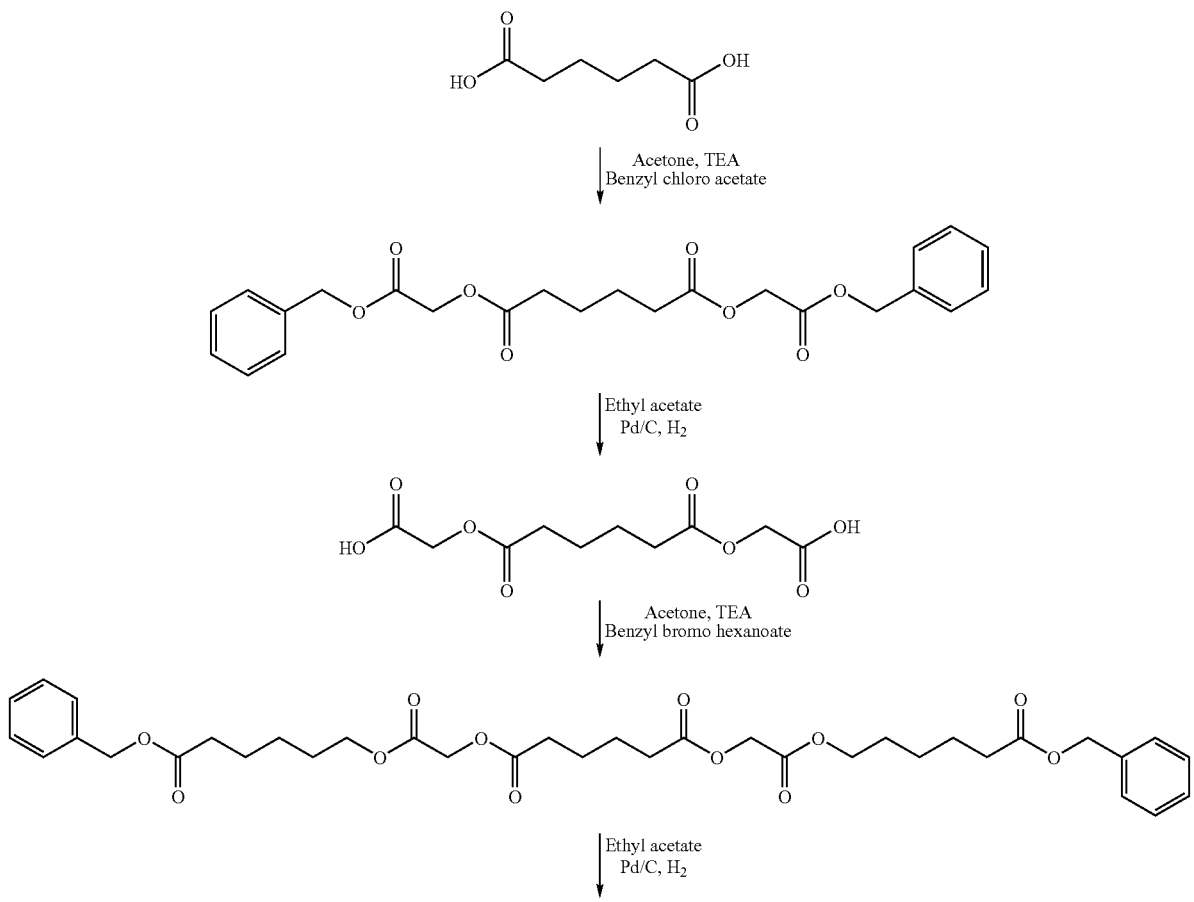

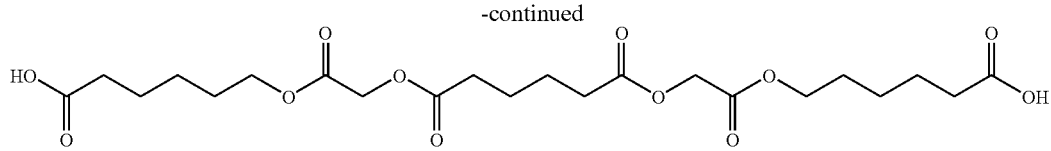

Example-40

Hexanedioic Acid Dibenzyloxycarbonylmethyl Ester (Adipic Acid with Benzyl Chloro Acetate)

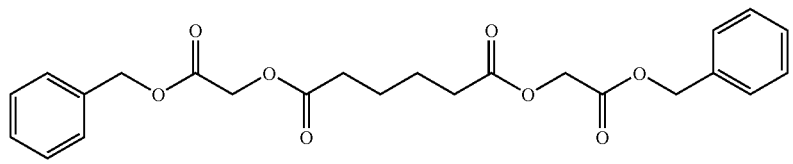

To a mixture of adipic acid (50 grams, 342.13 mmol), triethylamine (104 grams, 1.026 mol) in acetone (500 ml) in a 1 liter round bottom flask was added benzyl chloro acetate (145 grams, 785.4 mmol) drop wise. The reaction mixture was stirred at room temperature overnight. The reaction mixture was then poured onto cold water to yield crude 40 which was filtered, dried and purified by recrystallising from ethyl acetate to give pure 40 (97 grams, 69.7%) as a white powder with 97.9% purity as determined by HPLC, m.p: 73-75° C., The pure product 40 was also characterized using $^1$H NMR spectroscopy in CDCl$_3$: δ 1.72 (t, 2H, CH$_2$), 2.42 (t, 2H, CH$_2$), 4.65 (s, 2H, OCH2), 5.20 (s, 2H, OCH2), 7.38 (m, 5H, Ar).

Example-41

Hexanedioic Acid Dicarbonylmethyl Ester (Adipic Acid Diacid)

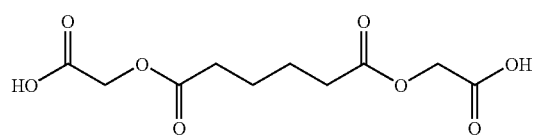

Hexanedioic acid dibenzyloxycarbonylmethyl ester 40 (97 grams, 219.46 mmol) was dissolved in ethyl acetate (400 ml) in a pressure vessel, 50% wet Palladium on carbon (5%, 20 grams) added and the mixture was left for stirring under an atmosphere of hydrogen (4 Kg) for 4 hours and 15 minutes. The catalyst was removed by filtration and the ethyl acetate was distilled off under vacuum and precipitated to yield crude 41 by addition of hexane. The crude was filtered off, dried and purified by recrystallisation in ethyl acetate to get pure 41 (30.8 grams) as a white powder with a melting point of 108-110° C., Mass: M−1=261.1. The pure product 41 was also characterized using $^1$H NMR spectroscopy in DMSO-d$_6$: δ 1.72 (t, 2H, CH$_2$), 2.42 (t, 2H, CH$_2$), 4.65 (s, 2H, OCH2), 5.20 (s, 2H, OCH2), 7.38 (m, 5H, Ar).

Example-42

Hexanedioic Acid Bis-(5-Benzyloxycarbonylpentyloxycarbonyl Methyl) Ester (Benzyl Adipic Diglycolate Dicaproate)

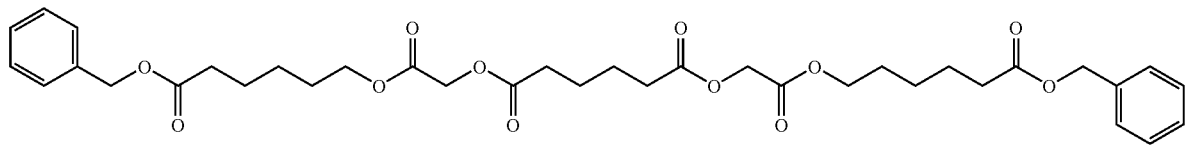

To a mixture of hexanedioic acid dicarbonylmethyl ester 41 (30 grams, 205.28 mmol), triethylamine (48 ml, 344.38 mmol) in acetone (300 ml) in a 1 liter round bottom flask was added benzyl 6-bromo hexanoate (72 grams, 252.63 mmol) drop wise. The reaction mixture was stirred at room temperature overnight and poured onto cold water to yield crude 42. Crude 42 was then extracted into ethyl acetate and dried over sodium sulphate. The ethyl acetate was distilled off under reduced pressure and purified by column chromatography on silica gel using chloroform: ethyl acetate as eluant to give pure 42 (35 grams) as light yellow syrup. Mass: M+1=671, The pure product 42 was also characterized using $^1$H NMR spectroscopy in CDCl$_3$: δ1.24 (t, 2H, CH$_2$), 1.36 (m, 2H, CH$_2$), 1.70 (m, 4H, CH$_2$), 2.34 (t, 2H, CH$_2$) 2.40 (t, 2H, CH$_2$), 4.12 (t, 2H, OCH2), 4.55 (s, 2H, OCH2), 5.08 (s, 2H, OCH2), 7.32 (m, 5H, Ar).

Example-43

Synthesis of Hexanedioic Acid Bis-(5-Carboxy-Pentyloxycarbonyl Methyl) Ester (Adipic Acid Diglycolate Dicaproic Acid)

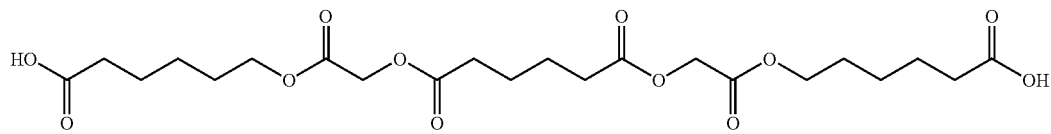

Hexanedioic acid bis-(5-benzyloxycarbonyl-pentyloxycarbonylmethyl) ester 42 (33 grams, 49.25 mmol) was dissolved in ethyl acetate (200 ml) in a pressure vessel, 50% wet Palladium on carbon (5%, 8 grams) added and the mixture stirred under an atmosphere of hydrogen (4 Kg) for 19 hours. The catalyst was removed by filtration and distilled off the ethyl acetate under vacuum and precipitated the crude by adding hexane, filtered and dried to get pure 43 (20 grams) as a white powder with a melting point of 96-99° C., Mass: M+Na=512. The pure product 43 was also characterized using $^1$H NMR spectroscopy in CDCl$_3$: δ 1.24 (t, 2H, CH$_2$), 1.36 (m, 2H, CH$_2$), 1.70 (m, 4H, CH$_2$), 2.34 (t, 2H, CH$_2$) 2.40 (t, 2H, CH$_2$), 4.12 (t, 2H, OCH2), 4.55 (s, 2H, OCH2), 5.08 (s, 2H, OCH2), 7.32 (m, 5H, Ar).

Adipic Tetraglycolic Acid

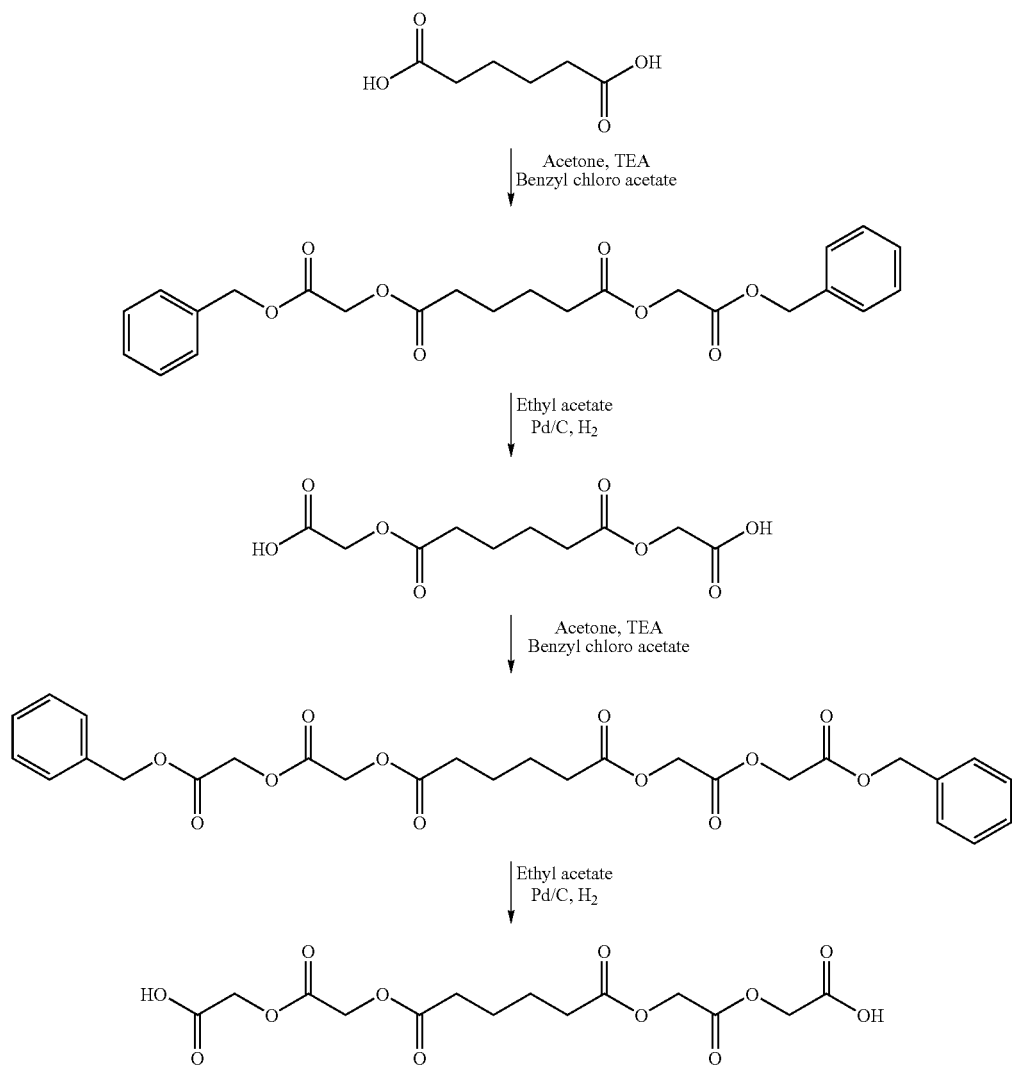

Example-44

Synthesis of Hexanedioic Acid Dibenzyloxycarbonylmethoxycarbonylmethyl Ester (Benzyl Adipic Tetraglycolate)

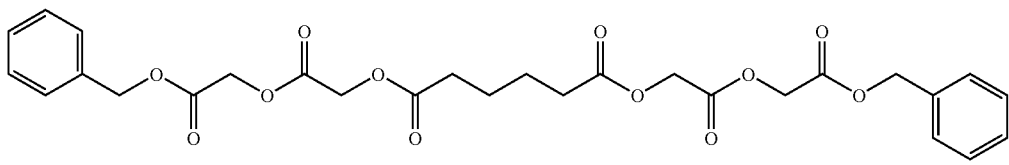

To a mixture of hexanedioic acid dicarbonylmethyl ester 41 (30 grams, 205.28 mmol), triethylamine (35 grams, 334.8 mmol) in acetone (300 ml) was added benzyl chloro acetate (46.5 grams, 251.87 mmol) dropwise and stirred at room temperature overnight. The reaction mixture was poured onto cold water and crude 44 was extracted into ethyl acetate, dried over sodium sulphate, distilled under reduced pressure and purified by column chromatography on silica gel using chloroform: ethyl acetate as eluant to give pure 44 (53 grams as a light yellow syrup. Mass: M+=558.9. The pure product 44 was also characterized using $^1$H NMR spectroscopy in $CDCl_3$: δ 1.68 (t, 2H, $CH_2$), 2.36 (t, 2H, $CH_2$), 4.64 (s, 4H, OCH2), 5.12 (s, 2H, OCH2), 7.26 (m, 5H, Ar)

Example-45

Synthesis Of Hexanedioic Acid Dicarbonylmethoxy Carbonylmethyl Ester (Adipic Tetra Glycolic Acid)

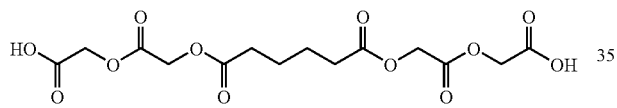

Into a solution of hexanedioic acid dibenzyloxycarbonylmethoxycarbonylmethyl ester 44 (116 grams, 262.44 mmol) in ethyl acetate (600 ml) in a pressure vessel was added 50% wet palladium on carbon (5%, 20 grams) and the mixture was left for stirring under an atmosphere of hydrogen (4 Kg) for 19 hours. The catalyst was removed by filtration and ethyl acetate was distilled off under vacuum followed by precipitation in hexane to yield crude 45, which was filtered and dried to get pure 45 (29 grams) as a white powder with a melting point of 111-115° C., Mass: M+1=379, The pure product 45 was also characterized using $^1$H NMR spectroscopy in a mixture of $CDCl_3$ and DMSO-$d_6$: δ 1.68 (t, 2H, $CH_2$), 2.36 (t, 2H, $CH_2$), 4.52 (s, 2H, $OCH_2$), 4.64 (s, 2H, $OCH_2$)

Caprolactone Diamine Tetraglycolic Acid

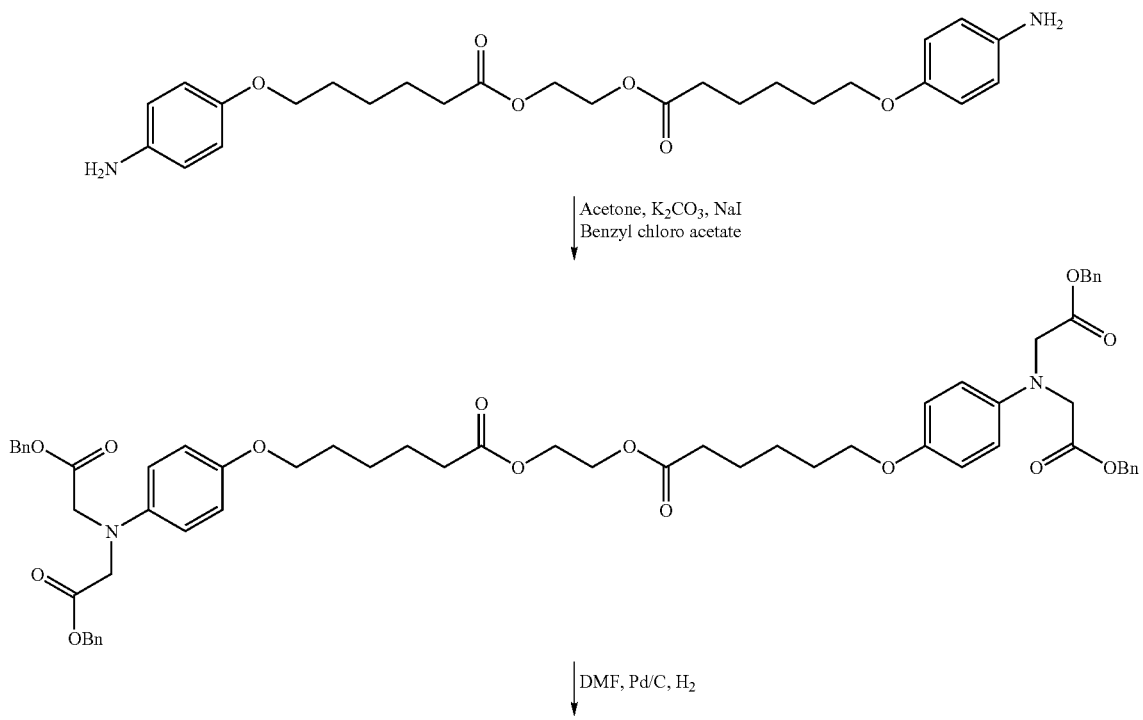

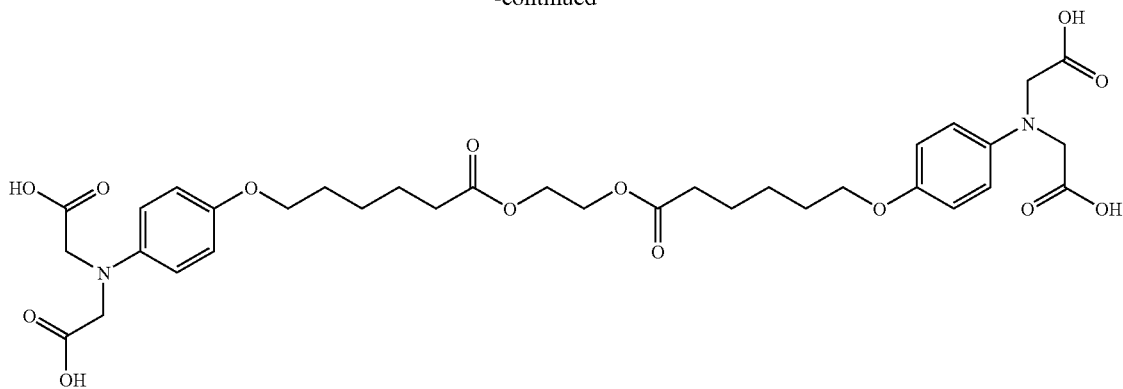

Example-46

Synthesis of Benzylated Caprolactone Diamine Tetraglycolate

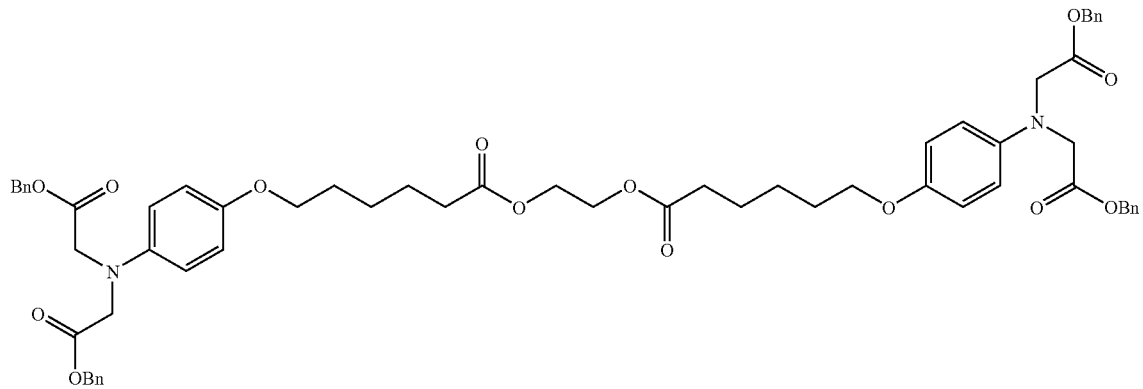

To a mixture of caprolactone diamine (50 grams, 105.80 mmol), anhydrous $K_2CO_3$ (220 grams, 1.592 mol), sodium iodide (80 grams, 533.72 mmol) in anhydrous acetone (1000 ml) in a 3 liter round bottom flask was added benzyl chloro acetate (157.5 grams, 853.66 mmol) and refluxed for 48 hours. Acetone was distilled off and water (500 ml) was added. Crude 46 was extracted into ethyl acetate, dried over anhydrous sodium sulphate, distilled of solvent under reduced pressure and the residue purified by column chromatography on silica gel using hexane:ethyl acetate to get pure 46 (84 grams) as a light yellow syrup. Mass: M+=1064.8. The pure product 46 was also characterized using $^1H$ NMR spectroscopy in $CDCl_3$: δ 1.48 (m, 2H, $CH_2$), 1.70 (m, 4H, $CH_2$), 2.34 (t, 2H, $CH_2$), 3.82 (t, 2H, $CH_2$), 4.06 (s, 4H, $CH_2$), 4.24 (s, 2H, $CH_2$), 5.08 (s, 4H, $CH_2$), 6.52 (d, 2H, Ar), 6.70 (d, 2H, Ar), 7.25 (m, 10H, Ar).

Example-47

Synthesis of Caprolactone Diamine Tetraglycolic Acid

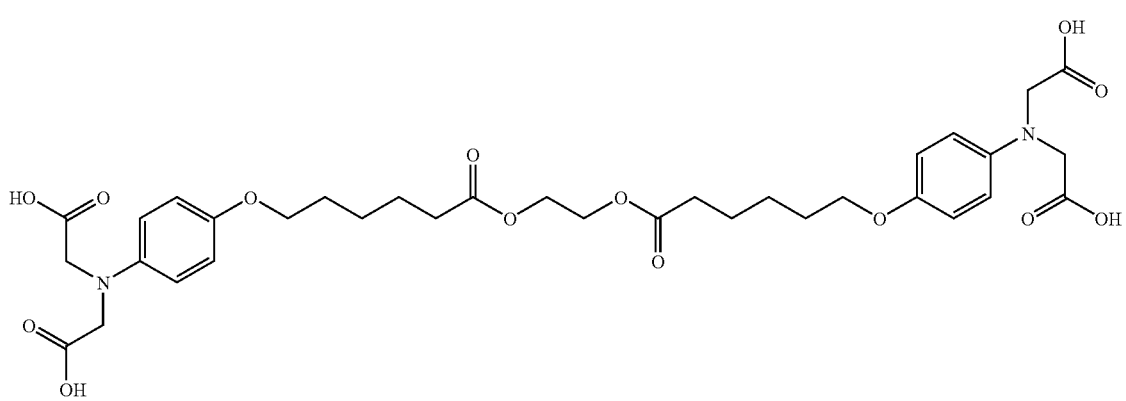

Benzylated caprolactone diamide 46 (10 grams) was dissolved in 100 ml of dry ethyl acetate in a pressure vessel. 50% wet palladium on carbon (10%, 3 grams) was added to the reaction mixture and the mixture was left for stirring under an atmosphere of hydrogen (4 Kg) overnight. The catalyst was removed by filtration and 80% of the Ethyl acetate was distilled off to get the crude 47, which was purified by suitable method to get pure 47. M.p: Mass: M+, $^1$H NMR (DMSO-$d_6$).

To a solution of ethylene glycol diglycolate diamine (50 grams, 138.74 mmol) in DMF was added triethylamine (68 ml, 487.87 mmol) cooled to 10° C. under $N_2$ atmosphere; added benzyloxy acetyl chloride (76.8 gm, 416.26 mmol) drop wise and further stirred overnight at room temperature. The TLC showed the presence of unreacted ethylene glycol diglycolate diamine, so further quantity of benzyloxy acetyl chloride (10 gm, 54.20 mmol) in DMF (50 ml) was added and stirred at room temperature over night, reaction mass poured onto cold water, precipitated solid was filtered dried and recrystallised from ethyl acetate:hexane (1:6) filtered the pure product to get pure 51 (56 gm) as white powder with a melting point of 111-112° C., Mass: M+=656. The pure product 51

Glycolate Diamide Diol

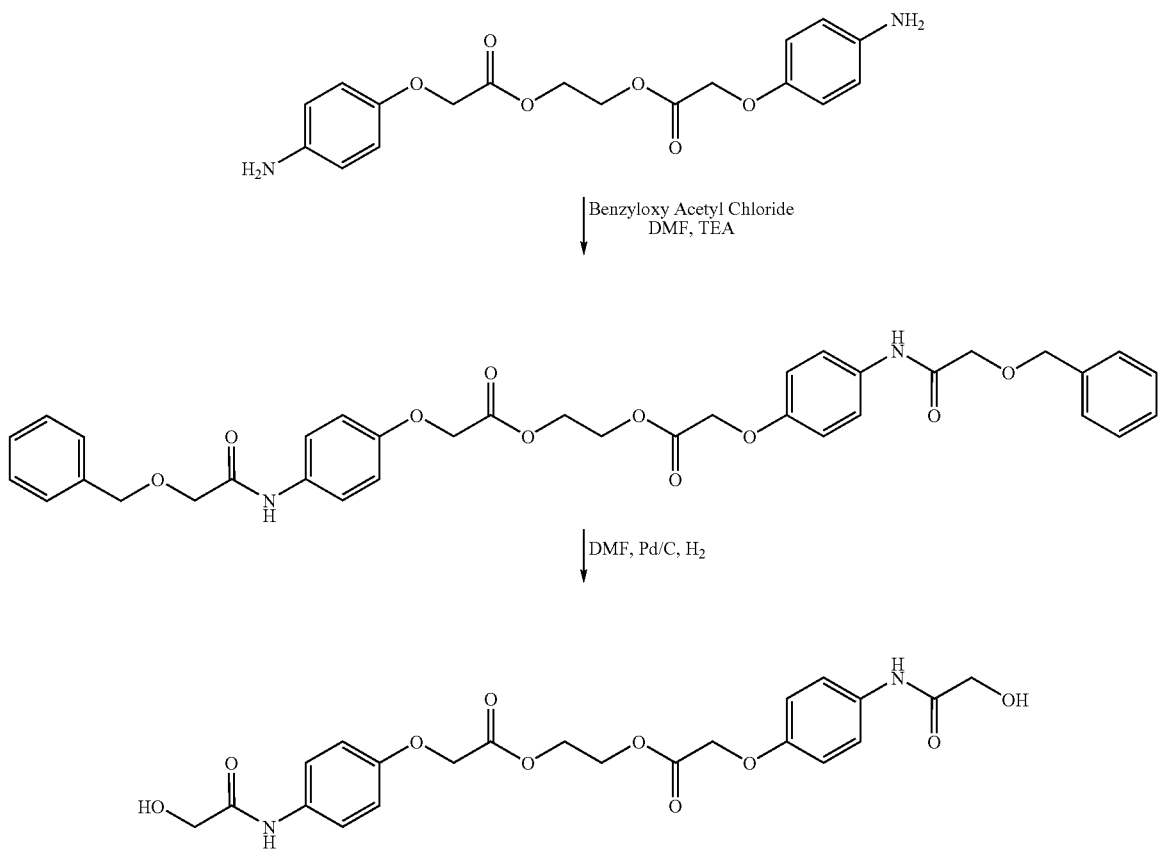

Example-51

Synthesis of Benzylated Glycolate Diamide was also characterized using $^1$H NMR spectroscopy in a mixture of $CDCl_3$ and DMSO-$d_6$: δ 4.02 (s, 2H, $CH_2$), 4.40 (s, 2H, $CH_2$), 4.64 (s, 4H, $CH_2$), 6.82 (d, 2H, Ar), 7.36 (m, 5H, Ar), 7.54 (d, 2H, Ar)

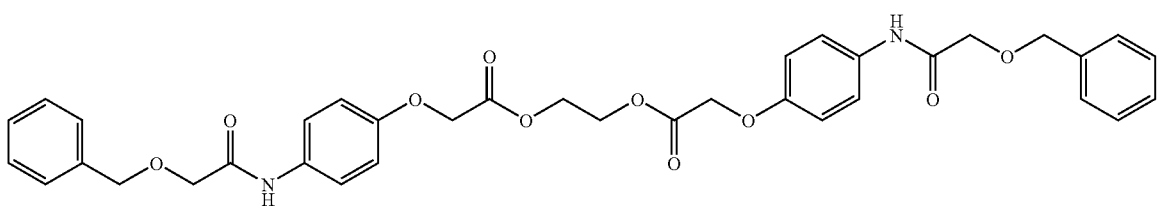

Example-52

Synthesis of Glycolate Diamide Diol

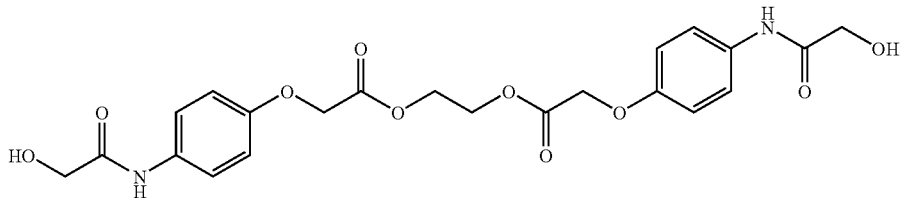

Benzylated Glycolate Diamide 51 (50 grams) was dissolved in DMF (300 ml) in a pressure vessel, 50% wet palladium on carbon (5%, 12 grams) added and the mixture stirred under an atmosphere of hydrogen (4 Kg) overnight. The catalyst was removed by filtration and distilled off 80% of the DMF and precipitated by adding to cold water, filtered and dried to get pure 52 (20 gm) as a white powder with a melting point of 180-183° C., Mass: M+=476. The pure product 52 was also characterized using $^1$H NMR spectroscopy in a mixture of $CDCl_3$ and DMSO-$d_6$: δ 3.96 (s, 2H, $CH_2$), 4.36 (s, 2H, $CH_2$), 4.72 (s, 4H, $CH_2$), 6.86 (d, 2H, Ar), 7.58 (d, 2H, Ar), 9.54 (s, 1H, NH).

When ranges are used herein for physical properties, such as molecular weight, or chemical properties, such as chemical formulae, all combinations and subcombinations of ranges and specific embodiments therein are intended to be included.

The disclosures of each patent, patent application and publication cited or described in this document are hereby incorporated herein by reference, in their entireties.

When any variable occurs more than one time in any constituent or in any formula, its definition in each occurrence is independent of its definition at every other occurrence. Combinations of substituents and/or variables are permissible only if such combinations result in stable compounds.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form or to any specific optical or geometric isomer, except where such stereochemistry is clearly defined.

Those skilled in the art will appreciate that numerous changes and modifications maybe made to the preferred embodiments of the invention and that such changes and modifications maybe made without departing from the spirit of the invention. It is, therefore, intended that the appended claims cover all such equivalent variations as fall within the true spirit and scope of the invention.

What is claimed is:

1. A polyester of the formula:

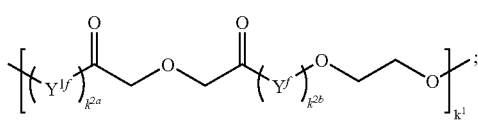

wherein:

each $Y^{1f}$ is independently $—C(=O)CH_2O—$, $—C(=O)CH(CH_3)O—$, $—C(=O)CH_2OCH_2CH_2O—$, and $—C(=O)CH_2CH_2CH_2CH_2CH_2O—$;

each $Y^f$ is independently $—OCH_2C(=O)—$, $—OCH(CH_3)C(=O)—$, $—OCH_2CH_2OCH_2C(=O)—$, and $—OCH_2CH_2CH_2CH_2CH_2C(=O)—$;

$k^1$ is an integer from about 100 to about 5000; and each $k^{2a}$ and $k^{2b}$ is independently 1 to about 5.

2. A polyester of claim 1, wherein:
$Y^{1f}$ is $—C(=O)CH_2O—$ or $—C(=O)CH(CH_3)O—$; and
$Y^f$ is $—OCH_2C(=O)—$ or $—OCH(CH_3)C(=O)—$.

3. A polyester of claim 1, wherein:
$Y^{1f}$ is $—C(=O)CH_2O—$; and
$Y^f$ is $—OCH_2C(=O)—$.

4. A polyester of claim 1, wherein:
$Y^{1f}$ is $—C(=O)CH_2O—$; and
$Y^f$ is $—OCH(CH_3)C(=O)—$.

5. A polyester of claim 1, wherein:
$Y^{1f}$ is $—C(=O)CH(CH_3)O—$; and
$Y^f$ is $—OCH_2C(=O)—$.

6. A polyester of claim 1, wherein:
$Y^{1f}$ is $—C(=O)CH(CH_3)O—$; and
$Y^f$ is $—OCH(CH_3)C(=O)—$.

7. A polyester of claim 1, wherein the polyester is of the formula:

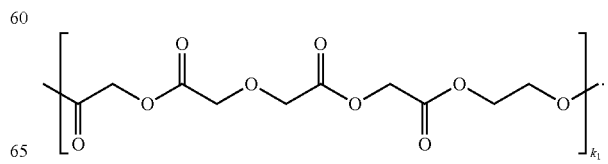

8. A polyester of claim 1, wherein the polyester is of the formula:
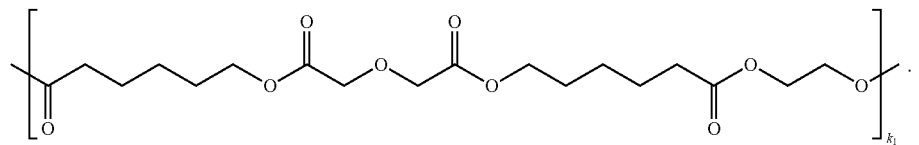
9. A polyester of claim 1, wherein the polyester is of the formula:
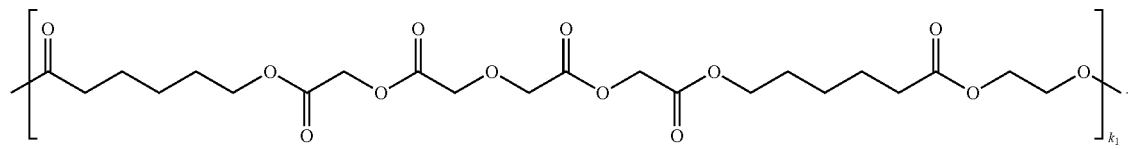
* * * * *